US008603999B2

(12) United States Patent
Drummond et al.

(10) Patent No.: US 8,603,999 B2
(45) Date of Patent: Dec. 10, 2013

(54) AMPHIPHILE PRODRUGS

(75) Inventors: Calum John Drummond, Victoria (AU); Sharon Marie Sagnella, New South Wales (AU); Minoo Jalili Moghaddam, New South Wales (AU); Xiaojuan Gong, New South Wales (AU)

(73) Assignee: Commonwealth Scientific and Industrial Research Organisation, Austrailian Capital Territory (AU)

( * ) Notice: Subject to any disclaimer, the term of this patent is extended or adjusted under 35 U.S.C. 154(b) by 105 days.

(21) Appl. No.: 13/132,880

(22) PCT Filed: Dec. 4, 2009

(86) PCT No.: PCT/AU2009/001586
§ 371 (c)(1),
(2), (4) Date: Aug. 29, 2011

(87) PCT Pub. No.: WO2010/063080
PCT Pub. Date: Jun. 10, 2010

(65) Prior Publication Data
US 2011/0301114 A1 Dec. 8, 2011

(30) Foreign Application Priority Data

Dec. 5, 2008 (AU) ................. 2008906311

(51) Int. Cl.
*A01N 43/04* (2006.01)
*A61K 31/70* (2006.01)
(52) U.S. Cl.
USPC ............. 514/49; 514/43; 536/23.1; 536/28.1; 536/28.4; 536/28.5; 536/28.51; 536/28.53; 536/28.55

(58) Field of Classification Search
None
See application file for complete search history.

(56) References Cited

U.S. PATENT DOCUMENTS

| | | | |
|---|---|---|---|
| 3,944,675 | A | 3/1976 | Symchowicz et al. |
| 4,810,697 | A | 3/1989 | Speiser et al. |
| 4,966,891 | A | 10/1990 | Fujiu et al. |
| 5,472,949 | A | 12/1995 | Arasaki et al. |
| 5,531,925 | A | 7/1996 | Landh et al. |
| 5,744,461 | A | 4/1998 | Hostetler et al. |
| 6,284,267 | B1 | 9/2001 | Aneja |
| 6,599,887 | B2 | 7/2003 | Hostetler et al. |
| 6,770,299 | B1 | 8/2004 | Muller et al. |
| 2002/0164481 | A1 | 11/2002 | Garcia et al. |
| 2003/0229006 | A1 | 12/2003 | Ekwuribe |
| 2003/0229129 | A1 | 12/2003 | Kraemer et al. |
| 2004/0208844 | A1 | 10/2004 | Ignatious |
| 2005/0163812 | A1 | 7/2005 | Hoath et al. |
| 2006/0073199 | A1 | 4/2006 | Chaubal et al. |

FOREIGN PATENT DOCUMENTS

| | | |
|---|---|---|
| AU | 619220 | 5/1989 |
| AU | 625188 | 9/1991 |
| AU | 671491 | 6/1994 |
| EP | 0 126 751 B2 | 1/1993 |
| EP | 0 602 454 | 6/1994 |
| EP | 0 316 704 B1 | 7/1995 |
| WO | WO 84/02076 | 6/1984 |
| WO | WO 89/07938 | 9/1989 |
| WO | WO 89/10348 | 11/1989 |
| WO | WO 96/22303 | 7/1996 |
| WO | WO 2004/022530 | 3/2004 |
| WO | WO 2005/021046 | 3/2005 |
| WO | WO 2005/077336 | 8/2005 |
| WO | WO 2006/002873 | 1/2006 |
| WO | WO 2006/085075 | 8/2006 |
| WO | WO 2006/090029 | 8/2006 |
| WO | WO 2009/071850 | 6/2009 |
| WO | WO 2009/077670 | 6/2009 |
| WO | WO 2009/077671 | 6/2009 |
| WO | WO 2010/063080 | 6/2010 |

OTHER PUBLICATIONS

Alexander, R.L. et al., "A Novel Phospholipid Gemcitabine Conjugate Is Able to Bypass Three Drug-Resistance Mechanisms," Cancer Chemotherapy and Pharmacology, 56(1), pp. 15-21, 2005.
Allen, T.M. et al., "Drug Delivery Systems: Entering the mainstream," Science, 303, pp. 1818-1822, 2004.
Angelov, B. et al., "Detailed Structure of Diamond-Type Cubic Nanoparticles," Journal of the American Chemical Society, 128, pp. 5813-5817, 2006.
Barauskas, J. et al.,S"elf-Assembled Lipid Superstructures: Beyond Vesicles and Lipsomes," Nano Letters, 5(8), pp. 1615-1619, 2005.
Bence, A.K. et al., "The Effect of DB-67, a Lipophilic Camptothecin Derivative, on Topoisomerase I Levels in Non-Small-Cell Lung Cancer Cells," Cancer Chemotherapy and Pharmacology, 54(4), pp. 354-360, 2004.
Brannon-Peppas, L. et al., "Nanoparticle and Targeted Systems for Cancer Therapy," Advanced Drug Delivery Reviews, 56(11), pp. 1649-1659, 2004.

(Continued)

Primary Examiner — Patrick Lewis
(74) Attorney, Agent, or Firm — Kilpatrick Townsend & Stockton LLP

(57) ABSTRACT

Amphiphilic prodrugs of general formula A-X are disclosed, wherein A is a biologically active agent or may be metabolised to a biologically active agent; and X is selected from the group consisting of R, or up to three R moieties attached to a linker, $Y_1$, $Y_2$ or $Y_3$, wherein R is selected from a group consisting of alkyl, alkenyl, alkynyl, branched alkyl, branched alkenyl, branched alkynyl, substituted alkyl, substituted alkenyl and substituted alkynyl groups and their analogues; $Y_1$ is a linker group which covalently attached to an R group at one site and is attached to A at a further independent site; $Y_2$ is a linker group which is covalently attached to two R groups at two independent sites and is attached to A at a further independent site; and $Y_3$ is a linker group which is covalently attached to three R groups at three independent sites and is attached to A at a further independent site. Self-assembly of the amphiphilic prodrugs into reverse lyotropic phases, particularly hexagonal, cubic and sponge, is disclosed. In preferred embodiments A is dopamine or a 5-fluorouracil prodrug.

10 Claims, 19 Drawing Sheets

(56) References Cited

OTHER PUBLICATIONS

Brioschi, A. et al., "Cholesterylbutyrate Solid Lipid Nanoparticles as a Butyric Acid Prodrug," Molecules, 13, pp. 230-254, 2008.
Bunjes, H. et al., "Thermotropic Liquid Crystalline Drugs," Journal of Pharmacy and Pharmacology, 57, pp. 807-816, 2005.
Calviello, G. et al., "Docosahexaenoic Acid Enhances the Susceptibility of Human Colorectal Cancer Cells to 5-Fluorouracil," Cancer Chemotherapy and Pharmacology, 55(1), pp. 12-20, 2005.
Cherezov, V. et al., "Crystallization Screens: Compatibility with the Lipidic Cubic Phase for in Meso Crystallization of Membrane Proteins," Biophysical Journal, 81, pp. 225-242, 2001.
Choi, S.K. et al., "Nucleoside-Based Phospholipids and Their Liposomes Formed in Water," ChemBioChem, 6, pp. 432-439, 2005.
Conn, C. et al., "Nanobiotechnology: From Water Treatment to Drug Delivery," BioNano Materials Australia, pp. 20-22, 2007.
Couvreur, P. et al., "Squalenoyl Nanomedicines as Potential Therapeutics," Nano Letters, 6(11), pp. 2544-2548, 2006.
Cubosomes®, product information, www.camurus.se, Mar. 17, 2008.
Deverre, J.R. et al., "Synthesis and Aqueous Organization of 1,3-Dipalmitoyl-2-(4-Aminobutyryl) Glycerol HCl: A Diglyceride Prodrug," Chemistry and Physics of Lipids, 59, pp. 75-81, 1991.
Dong, Y.D. et al., "Bulk and Dispersed Aqueous Phase Behavior of Phytantriol: Effect of Vitamin E Acetate and F127 Polymer on Liquid Crystal Nanostructure," Langmuir, 22, pp. 9512-9518, 2006.
Drummond, C.J. et al., Surfactant Self-Assembly Objects as Novel Drug Delivery Vehicles, Current Opinion in Colloid & Interface Science, 4, pp. 449-456, 2000.
Ferguson, M.J. et al., "The Role of Pro-Drug Therapy in the Treatment of Cancer," Drug Resistance Updates, 4, pp. 225-232, 2001.
Garg, G. et al., "Cubosomes: An overview," Biological Pharmaceutical Bulletin, 30(2), pp. 350-353, 2007.
Gin, D.L. et al., "Polymerized Lyotropic Liquid Crystal Assemblies for Materials Applications," Accounts of Chemical Research, 34, pp. 973-980, 2001.
Gong et al., "Nanostructured Self-Assembly Materials From Neat and Aqueous Solutions of C18 Lipid Pro-Drug Analogues of Capecitabine—A Chemotherapy Agent. Focus on Nanoparticulate Cubosomes™ of the Oleyl Analogue," Soft Matter, 7, pp. 5764-5776, 2011.
Gong et al., "Lamellar Crystalline Self-Assembly Behaviour and Solid Lipid Nanoparticles of a Palmityl Prodrug Analogue of Capecitabine—A Chemotherapy Agent," Colloids and Surfaces B, vol. 85, Issue 2, pp. 349-359, Jul. 1, 2011.
Gong et al., "Lyotropic Liquid Crystalline Self-Assembly Material Behavior and Nanoparticulate Dispersions of a Phytanyl Pro-Drug Analogue of Capecitabine—A Chemotherapy Agent," ACS Applied Materials Interfaces, 3, pp. 1552-1561, 2011.
Gulati, M. et al., "Lipophilic Drug Derivatives in Liposomes," International Journal of Pharmaceutics, 165, pp. 129-168, 1998.
Högestätt, E.D. et al., "Conversion of Acetaminophen to the Bioactive N-Acylphenolamine AM404 Via Fatty Acid Amide Hydrolase-Dependent Arachidonic Acid Conjugation in the Nervous System," The Journal of Biological Chemistry, 280(36), pp. 31405-31412, 2005.
Jin, Y. et al., "Langmuir Monolayers of the Long-Chain Alkyl Derivatives of a Nucleoside Analogue and the Formation of Self-Assembled Nanoparticles," Colloids and Surfaces B: Biointerfaces, 42, pp. 45-51, 2005.
Jin, Y. et al., "Self-Assembled Drug Delivery Systems 1. Properties and In Vitro/In Vivo Behavior of Acyclovir Self-Assembled Nanoparticles (SAN)," Pharmaceutical Nanotechnology, 309, pp. 199-207, 2006.
Jin, Y. et al., "Effect of Temperature on the State of the Self-Assembled Nanoparticles Prepared From an Amphiphilic Lipid Derivative of Acyclovir," Colloids and Surfaces B: Biointerfaces, 54, pp. 124-125, 2007.
Jin, Y. et al., "Monolayers of the Lipid Derivatives of Isoniazid at the Air-Water Interface and the Formation of Self-Assembled Nanostructures in Water," Colloids and Surfaces B: Biointerfaces, 64, pp. 229-235, 2008.
Jin, Y. et al., "Self-Assembled Drug Delivery Systems 2. Cholesteryl Derivatives of Antiviral Nucleoside Analogues: Synthesis, Properties and the Vesicle Formation," Pharmaceutical Nanotechnology, 350, pp. 330-337, 2008.
Kaasgaard, T. et al., "Ordered 2D and 3D Nanostructured Amphiphile Self-Assembly Materials Stable in Excess Solvent," Physical Chemistry Chemical Physics, 8, pp. 4957-4975, 2006.
Kriwet, K. et al., "Binary Diclofenac Diethylamine Water-Systems—Micelles, Vesicles and Lyotropic Liquid-Crystals," European Journal of Pharmaceutics and Biopharmaceutics, 39(6), pp. 234-238, 1993.
Laughlin, R.G. et al., "Phase studies by Diffusive Interfacial Transport Using Near-Infrared Analysis for Water (DIT-NIR)," Journal of Physical Chemistry B, 104(31), pp. 7354-7362, 2000.
Lawson, K.A. et al., "Novel Vitamin E Analogue and 9-Nitro-Camptothecin Administered as Liposome Aerosols Decrease Syngeneic Mouse Mammary Tumor Burden and Inhibit Metastasis," Cancer Chemotherapy and Pharmacology, 54(5), pp. 421-431, 2004.
Mehnert, W. et al., "Solid Lipid Nanoparticles Production, Characterization and Applications," Advanced Drug Delivery Reviews, 47, pp. 165-196, 2001.
Miwa, M. et al., "Design of a Novel Oral Fluoropyrimidine Carbamate, Capecitabine, Which Generates 5-Fluorouracil Selectively in Tumours by Enzymes Concentrated in Human Liver and Cancer Tissue," European Journal of Cancer, 34(8), pp. 1274-1281, 1998.
Moreau, L. et al., "Vesicle Formation From a Synthetic Adenosine Based Lipid," Tetrahedron Letters, 46, pp. 1593-1596, 2005.
Müller-Goymann, C.C. et al., "Pharmacosomes—Multilamellar Vesicles Consisting of Pure-Drug," European Journal of Pharmaceutics and Biopharmaceutics, 37(2), pp. 113-117, 1991.
Niethammer, A et al., "Synthesis and Preclinical Characterization of a Paclitaxel Prodrug with Improved Antitumor Activity and Water Solubility," Bioconjugate Chemistry, 12(3), pp. 414-420, 2001.
Nikanjam, M. et al., "Synthetic Nano-LDL With Paclitaxel Oleate as a Targeted Drug Delivery Vehicle for Glioblastoma Multiforme," Journal of Controlled Release, 124, pp. 163-171, 2007.
Pech, B. et al., "Tensioactivity and Supramolecular Organization of the Palmitoyl Prodrug of Timolol," Pharmaceutical Research, 14(1), pp. 37-41, 1997.
Quan, J. et al., "The Synthesis of Amphiphatic Prodrugs of 1,2-Diol Drugs With Saccharide Conjugates by High Regioselective Enzymatic Protocol," Bioorganic & Medicinal Chemistry, 15, pp. 1741-1748, 2007.
Rautio, J. et al., "Prodrugs: Design and Clinical Applications," Nature Reviews Drug Discovery, 7, pp. 255-270, 2008.
Reddy, L.H. et al., "A New Nanomedicine of Gemcitabine Displays Enhanced Anticancer Activity in Sensitive and Resistant Leukemia Types," Journal of Controlled Release, 124(1-2), pp. 20-27, 2007.
Reddy, L.H. et al., "Squalenoyl Nanomedicine of Gemcitabine Is More Potent After Oral Administration in Leukemia-Bearing Rats: Study of Mechanisms," Anti-Cancer Drugs, 19(10), pp. 999-1006, 2008.
Reddy, L.H. et al., "Oral Absorption and Tissue Distribution of a New Sqaulenoyl Anticancer Nanomedicine," J Nanopart Res, 10, pp. 887-891, 2008.
Reddy, L.H. et al., "Squalenoylation Favorably Modifies the In Vivo Pharmacokinetics and Biodistribution of Gemcitabine in Mice," Drug Metabolism and Disposition, 36(8), pp. 1570-1577, 2008.
Reddy, L.H. et al., "Preclinical Toxicology (Subacute and Acute) and Efficacy of a New Squalenoyl Gemcitabine Anticancer Nanomedicine," Journal of Pharmacology and Experimental Therapeutics, 325(2), pp. 484-490, 2008.
Reddy, L.H. et al., "Anticancer Efficacy of Squalenoyl Gemcitabine Nanomedicine on 60 Human Tumor Cell Panel and on Experimental Tumor," Molecular Pharmaceutics, 6(5), pp. 1526-1535, 2009.
Rodrigues, D.G. et al., "Improvement of Paclitaxel Therapeutic Index by Derivatization and Association to a Cholesterol-Rich Microemulsion: In Vitro and In Vivo Studies," Cancer Chemotherapy and Pharmacology, 55(6), pp. 565-576, 2005.
Rosa, M. et al., "Spontaneous Formation of Vesicles and Dispersed Cubic and Hexagonal Particles in Amino Acid-Based Catanionic Surfactant Systems," Langmuir, 22, pp. 5588-5596, 2006.

(56) References Cited

OTHER PUBLICATIONS

Sagnella et al., "Nanostructured Nanoparticles of Self-Assembled Lipid Pro-Drugs as a Route to Improved Chemotherapeutic Agents," Nanoscale, 3, pp. 919-924, 2011.
Sarpietro, M. G. et al., "Conjugation of Squalene to Acyclovir Improves the Affinity for Biomembrane Models," International Journal of Pharmaceutics, 382(1-2), pp. 73-79, 2009.
Schellens, J.H.M., "Capecitabine," The Oncologist, 12, pp. 152-155, 2007.
Schreier, S. et al., "Surface Active Drugs: Self-Association and Interaction With Membranes and Surfactants. Physicochemical and Biological Aspects," Biochimica et Biophysica Acta, 1508, pp. 210-234, 2000.
Shah, J.C. et al., "Cubic Phase Gels As Drug Delivery Systems," Advanced Drug Delivery Reviews, 47, pp. 229-250, 2001.
Shimma, N. et al.,"The Design and Synthesis of a New Tumor-Selective Fluoropyrimidine Carbamate, Capecitabine," Bioorganic & Medicinal Chemistry, 8, pp. 1697-1706, 2000.
Spicer, P.T. et al., "Novel Process for Producing Cubic Liquid Crystalline Nanoparticles (Cubosomes)," Langmuir, 17, pp. 5748-5756, 2001.
Spicer, P.T., "Progress in Liquid Crystalline Dispersions: Cubosomes," Current Opinion in Colloid & Interface Science, 10, pp. 274-279, 2005.
Stevenson, C.L. et al., Pharmaceutical Liquid Crystals: The Relevance of Partially Ordered Systems, Journal of Pharmaceutical Sciences, 94(9), pp. 1861-1880, 2005.
Thierry, B. et al., "Delivery Platform for Hydrophobic Drugs: Prodrug Approach Combined With Self-Assemble Multilayers," Journal of the American Chemical Society, 127(6), pp. 626-627, 2005.
Vaizoglu, O. et al., "Pharmacosomes—A Novel Drug Delivery System," Acta Pharmaceutica Suecica, 23(3), pp. 163-172, 1986.
Vaizoglu, O. et al., "The Pharmacosome Drug Delivery Approach," European Journal of Pharmaceutics and Biopharmaceutics, 38(1), pp. 1-6, 1992.
Vodovozova, E.L. et al., Synthesis of a Lipid Derivative of the Antitumor Agent Methotrexate, Russian Journal of Bioorganic Chemistry, 30(6), pp. 663-665, 2004.
Vyas, S.P. et al., "Synthesis and Characterisation of Palymitoyl Propanolol Hydrochloride Auto-Lymphotrophs for Oral Administration," International Journal of Pharmaceutics, 186, pp. 177-189, 1999.
Wells, D. et al., "Nonionic Urea Surfactants: Influence of Hydrocarbon Chain Length and Positional Isomerism on the Thermotropic and Lyotropic Phase Behavior," Journal of Physical Chemistry B, 110, pp. 5112-5119, 2006.
Wissing, S.A. et al., "Solid Lipid Nanoparticles for Parenteral Drug Delivery," Advanced Drug Delivery Reviews, 56, pp. 1257-1272, 2004.
XELODA® (capecitabine) product information, Sep. 19, 2007, Roche.
Yang, S.C. et al., "Body Distribution in Mice of Intravenously Injected Camptothecin Solid Lipid Nanoparticles and Targeting Effect on Brain," Journal of Controlled Release, 59(3), pp. 299-307, 1999.
Yu, B.T. et al., "Enhanced Liver Targeting by Synthesis of N-1-Stearyl-5-Fu and Incorporation Into Solid Lipid Nanoparticles," Archives of Pharmacal Research, 26(12), pp. 1096-1101, 2003.
Zamboni, W.C., Concept and Clinical Evaluation of Carrier-Mediated Anticancer Agents, The Oncologist, 13, pp. 248-260, 2008.
Zhang, J.X. et al., "Temperature-Triggered Nanosphere Formation Through Self-Assembly of Amphiphilic Polyphosphazene," Macromolecular Chemistry and Physics, 207(14), pp. 1289-1296, 2006.
Commonwealth Scientific and Industrial Research Organisation et al., International Search Report dated Mar. 8, 2010 from PCT/AU2009/001586, filed Dec. 4, 2009.
Commonwealth Scientific and Industrial Research Organisation et al., International Preliminary Report on Patentability dated Mar. 25, 2011 from PCT/AU2009/001586, filed Dec. 4, 2009.
Commonwealth Scientific and Industrial Research Organisation et al., Written Opinion dated Nov. 5, 2010 from PCT/AU2009/001586, filed Dec. 4, 2009.
Fieser et al., "Reagents for Organic Synthesis," vol. 6, John Wiley and Sons, New York, N.Y., pp. 638-641, 1977.
Larock, "Comprehensive Organic Transformations," 2nd Ed.; John Wiley and Sons, New York, N.Y., pp. 20-21, 1999.
Laughlin "The Aqeuous Phase Behaviour of Surfactants," Chapter 8, The Structures and Properties of Surfactant Phases, pp. 181-237 and Chapter 12, pp. 406-416, Academic Press, San Diego, CA, 1994.
March, "Advanced Organic Chemistry," Fourth Edition, John Wiley and Sons, New York, N.Y., pp. 392-393, 1992.
Remington: The Science and Practice of Pharmacy, Chapter 21, pp. 304-318, 21st Ed, University of the Sciences in Philadelphia (eds), Lippincott Williams & Wilkins, Philadelphia, PA, 2005.
Small, "Handbook of Lipid Research, The Physical Chemistry of Lipids" Plenum Press, New York: Chapter 4, pp. 89-96, 1986.
Wuts et al., "Greene's Protective Groups in Organic Synthesis,"pp. 222-223, 272-275, 306-318, John Wiley & Sons, Inc., Fourth Edition, Hoboken, N.J., 2007.

AMPHIPHILE PRODRUGS

FIELD OF THE INVENTION

This invention relates to improved prodrugs, and compositions thereof. In particular, it relates to amphiphilic prodrugs.

BACKGROUND OF THE INVENTION

It is important that the dosage of any drug fall within a therapeutic window. The therapeutic window is defined at its lower boundary by the minimum concentration required to exert a therapeutic effect, and at its upper boundary by the concentration at which unacceptable toxicity effects are observed. A difficulty with some therapeutic agents, including chemotherapeutic agents such as 5-fluorouracil, is that they possess high toxicity and/or a fast clearance rate. This results in difficulties dosing within the therapeutic window. The dosing method generally employed for drugs that possess these properties often results in administration of a supra-optimal dose that rapidly falls to a sub-optimal level between administrations.

Several divergent approaches have been employed in an attempt to improve dosage regimes of therapeutic agents.

One approach is to chemically modify the active therapeutic agent and generate a prodrug. In vivo the prodrug is converted, for example, by hydrolytic, oxidative, reductive or enzymatic cleavage to the biologically active agent.

One such drug that has been successful converted into a prodrug is the 5-fluorouracil (5-FU) prodrug, such as Capecitabine or its analogues. Compounds of this nature are disclosed in a general sense in U.S. Pat. No. 4,966,891 and equivalent application EP 0316704 (F. Hoffmann-La Roche AG). Capecitabine undergoes three chemical conversions in vivo to generate 5-fluorouracil, namely: carboxylesterase-catalysed hydrolysis to generate 5'-deoxy-5-fluorocytidine; conversion of 5'-deoxy-5-fluorocytidine to 5'-deoxy-5-fluorouridine catalysed by cytidine deaminase, followed by conversion of 5'-deoxy-5-fluorouridine to active 5-FU preferentially at tumour sites catalysed by the angiogenic factor thymidine phosphorylase. In spite of being less toxic than 5-FU, Capecitabine and its analogues still possess substantial drawbacks; namely, they still possess an undesirable rapid clearance rate.

Another approach to prolong clearance is to encapsulate or otherwise non-covalently incorporate the biologically active drug or prodrug into a drug delivery vehicle or matrix. One investigated material is a biologically inert amphiphilic matrix. Amphiphiles are compounds that possess a hydrophilic portion and a hydrophobic portion. Under certain conditions, amphiphiles spontaneously aggregate, or self-assemble, into structures that possess at least some degree of internal order. The self-assembly behaviour of amphiphiles in solvent arises because of the preferential interaction between the solvent and either the hydrophilic or hydrophobic portion of the amphiphilic molecule. When an amphiphile is exposed to a polar solvent, the hydrophilic portion of the amphiphile tends to preferentially interact with the polar solvent, resulting in the formation of hydrophilic domains ('solvent domain'). The hydrophobic portion of the amphiphile molecules tend to be excluded from this domain, resulting in the de facto formation of a hydrophobic domain ('amphiphile domain'). Such self-generated aggregates are referred to throughout the specification as self-assembled structures. When being used as a drug delivery vehicle, the amphiphile self-assembled structure acts as an inert carrier of the biologically active agent. Amphiphile self-assembled structures represent promising drug-delivery vehicles, because the presence of both hydrophilic and hydrophobic domains potentially allows for the incorporation of both polar and non-polar active agents into the structure.

As self-assembled structures may exhibit a variety of orientational orders, these will be discussed here for clarity. If long-range orientational order is observed within the self-assembled structure at equilibrium, the self-assembled structure is termed a 'mesophase', a 'lyotropic liquid crystalline phase', a 'lyotropic phase' or, as used herein, simply a 'phase' of 'bulk phase'. Note that as well as the lyotropic liquid crystalline phase, there is another principal type of liquid crystalline phase, namely, the: thermotropic liquid crystalline phase. Thermotropic liquid crystals can be formed by heating a crystalline solid or by cooling an isotropic melt of an appropriate solute. Lyotropic liquid crystals may be formed by addition of a solvent to an appropriate solid or liquid amphiphile. The manipulation of parameters such as amphiphile concentration and chemical structure, solvent composition, temperature and pressure may result in the amphiphile-solvent mixture adopting lyotropic phases with distinctive characteristics.

Lyotropic phases may be classified in terms of the curvature of the interface between the hydrophilic and hydrophobic domains. The curvature between these domains is dependent upon several factors, including the concentration and molecular structure of the amphiphile. When the interface displays net curvature towards the hydrophobic domain, the phase is termed 'normal'. When the interface displays net curvature towards the hydrophilic domain, the phase is termed 'reverse' or 'inverse' (used interchangeably herein). If the net curvature of the system approaches zero, then the resulting phase may possess a lamellar-type structure that consists of planar amphiphile bilayers separated by solvent domains. Alternatively, the net curvature may approach zero if each point on the surface is as convex in one dimension as it is concave in another dimension; such phases are referred to as 'minimal surface' phases. Examples of particular phases that can be formed by self-assembled structures include but are not limited to: micellar (normal and reversed), hexagonal (normal and reversed), lamellar, cubic (normal, reversed and bicontinuous), and other intermediate phases such as reverse micellar cubic, the ribbon, mesh, or non-cubic 'sponge' bicontinuous phases.

Also, as well as the bulk phases described above, amphiphile self-assembled structure may be dispersed to form colloidal particles (so-called 'colloidosomes') that retain the internal structure of the non-dispersed bulk phase. When these particles possess the internal structure of a reversed bicontinuous cubic phase, the particles are colloquially referred to as cubosomes. Similarly, when the particles possess the internal structure of a reversed hexagonal phase, they are referred to as hexosomes. When the particles possess the internal structure of a lamellar phase, they are referred to as liposomes. Colloidal particles may also be formed from 'sponge' phases.

Another form of amphiphile self-assembled structure that has been utilised for drug delivery applications are solid lipid particles. Solid lipid particles are comprised of a solid lipid core stabilised by a surfactant surface layer, such as polysorbate 80.

As mentioned above, certain of these amphiphile self-assembled structures comprising biologically inert amphiphiles have been investigated for drug-delivery applications. These self-assembled structures are intended to act as an inert matrix or carrier into which biologically active molecules may be non-covalently incorporated. For instance, EP 0 126 751 B2 discloses the use of bulk cubic and reversed hexagonal phases for drug delivery applications. Certain of the colloidal particles have also been investigated for their application as drug delivery vehicles. For instance, U.S. Pat. No. 5,531,925 discloses colloidal particles comprising an interior of an amphiphilic-based phase, surrounded by a surface phase anchored to the bi- or mono-layer of the interior phase. The interior phase of the particles of U.S. Pat. No. 5,531,925 may be selected from reversed cubic, hexagonal or intermediate, or $L_3$ ('sponge') phases, or mixtures thereof. Certain solid lipid particles have been used as carriers for hydrophobic drugs. For example Campothecin, an anticancer agent which was mixed with an amphiphile, stabilised by poloxamer and then dispersed by homogenisation into solid lipid particles demonstrated increased drug levels in the brain tissues (Yang 1999).

Unfortunately, the self-assembled structures/drug delivery vehicles described above possess properties that make them unsuitable for their intended application, the undesirable properties including (i) toxicity, (ii) inappropriate absorption, distribution, metabolism and excretion profiles, and (iii) inappropriate biodegradability properties. Moreover, it is often difficult to achieve sufficient drug loadings into the structure such that a therapeutic effect is observed when the drug delivery vehicle is administered.

In an effort to increase drug loadings, the "pharmacosome" approach has been employed. This approach involves generating a prodrug that is capable of assembling into a micelle or liposome. Jin et al. identify some lipid-nucleoside analogues that can form normal lamellar vesicles (Jin 2005, Zhang 2006). However, micelles and liposomes also possess substantial drawbacks as phases suitable for drug delivery. For instance, micellar systems can disintegrate under dilution and below the critical micelle concentration (CMC). Additionally, oral application of liposomes is limited due to the fast uptake of the liposomes by phagocytes of the immune systems in stomach and duodenum.

All of the above-described approaches suffer from substantial drawbacks. Accordingly, there remains a need to generate better methods of drug delivery.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The current invention seeks to provide prodrugs capable of self-assembly into higher order hexagonal, cubic and/or sponge phase. Two forms of self-assembled structures have been indentified as being particularly suitable to act as drug delivery vehicles, namely lyotropic liquid crystals and solid lipid particles. The invention also provides pharmaceutical compositions thereof. These higher order phases provide a modified release profile for the drug when compared with the lower order micellar and liposomal pharmacosomes of the prior art.

Accordingly, in a first aspect of the present invention there is provided a prodrug of a general formula (I):

A-X    I wherein A is a biologically active agent or an agent capable of being metabolised to a biologically active agent; and X is selected from the group consisting of a substituent according to formula (a), a substituent according to formula (b), a substituent according to formula (c), and a substituent according to formula (d):

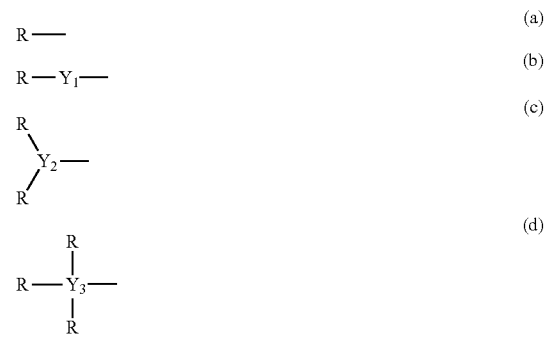

wherein

R is selected from a group consisting of alkyl, alkenyl, alkynyl, branched alkyl, branched alkenyl, branched alkynyl, substituted alkyl, substituted alkenyl and substituted alkynyl groups and their analogues;

$Y_1$ is a linker group that is covalently attached to one R group at one attachment site and to A at a second attachment site;

$Y_2$ is a linker group that is covalently attached to two R groups (which may be identical or different) at two independent attachment sites and is attached to A at a third attachment site; and $Y_3$ is a linker group that is covalently attached to three R groups (which may be identical or different) at three independent attachment sites and is attached to A at a fourth attachment site.

The biologically active agent may be a drug, in which case A-X represents a prodrug. The agent capable of being metabolised to a biologically active agent may be a prodrug, in which case A-X represents a pre-prodrug. The biologically active agent is preferably a therapeutically active agent.

Accordingly, in an embodiment of this aspect there is provided a prodrug of a general formula (I):

A-X    I wherein A is a therapeutically active agent or an agent capable of being metabolised to a therapeutically active agent;

X is selected from the group consisting of a substituent according to formula (a), a substituent according to formula (b), a substituent according to formula (c) and a substituent according to formula (d):

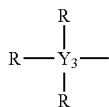

wherein $Y_1$ is a linker group that is covalently attached to the group R at one attachment site and to the therapeutically active agent A at a second attachment site;

$Y_2$ is a linker group that is covalently attached to two R groups (which may be identical or different) at two independent attachment sites and is attached to the therapeutically active agent A at a third attachment site;

$Y_3$ is a linker group that is covalently attached to three R groups (which may be identical or different) at three independent attachment sites and is attached to the therapeutically active agent A at a fourth attachment site; and R is selected from a group consisting of alkyl, alkenyl, alkynyl, branched alkyl, branched alkenyl, branched alkynyl, substituted alkyl, substituted alkenyl and substituted alkynyl groups and their analogues.

In another embodiment of this aspect there is provided a prodrug of a general formula (I):

A-X    I wherein A is a biologically active agent or an agent capable of being metabolised to a biologically active agent;

X is selected from the group consisting of a substituent according to formula (a), a substituent according to formula (b), a substituent according to formula (c) and a substituent according to formula (d):

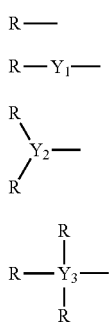

wherein

R is selected from a group consisting of alkyl, alkenyl, alkynyl, branched alkyl, branched alkenyl, branched alkynyl, substituted alkyl, substituted alkenyl and substituted alkynyl groups and their analogues;

$Y_1$ is a linker group that is covalently attached to one R group at one attachment site and to A at a second attachment site;

$Y_2$ is a linker group that is covalently attached to two R groups (which may be identical or different) at two independent attachment sites and is attached to A at a third attachment site; and $Y_3$ is a linker group that is covalently attached to three R groups (which may be identical or different) at three independent attachment sites and is attached to A at a fourth attachment site.

Optionally, R has a linear chain length equivalent to 8 to 30 carbon atoms. R is generally hydrophobic. In one embodiment, R is alpha-tocopherol. In another embodiment, R is an isoprenoid group. In other embodiments, R is an hydroxylated alkyl or hydroxylated alkenyl group. Preferred embodiments of R are: alkyl, alkenyl, branched alkyl and alkenyl (isoprenoid) and their analogues such as alpha-tocopherol, hydroxylated alkyl or alkenyl groups. In preferred embodiments, R has a chain length equivalent to 10 to 30 carbon atoms. Preferably, the chain length is equivalent to 10 to 24 carbon atoms, and more preferably equivalent to 14 to 24 carbon atoms. When X is a substituent according to formula (c) or formula (d), each R may be independently selected from the group consisting of alkyl, alkenyl, alkynyl, branched alkyl, branched alkenyl, branched alkynyl, substituted alkyl, substituted alkenyl and substituted alkynyl groups and their analogues. Alternatively, both R groups may be identical. Generally, R is intended to confer self assembling properties to A.

In some embodiments according to the current invention, $Y_1$, $Y_2$ and $Y_3$ are linker groups. A "linker" refers to a group that acts as a spacer between the biologically active agent A and the group R. Linkers are at least bifunctional in the case of $Y_1$, are at least trifunctional in the case of $Y_2$, and are at least tetrafunctional in the case of $Y_3$, containing at least one functional group (an "attachment site") to anchor the group R at one site in the molecule, and another selectively cleavable functional group at another attachment site to anchor the drug A. Examples of functional groups, including selectively cleavable functional groups, include but are not limited to: ethers, esters, amides, carbamates, imides, imines, carbonates, thioethers, thioesters, and disulfides.

For instance, $Y_1$, $Y_2$, $Y_3$ may be at least one functional group attached to at least one selectively cleavable functional group. Preferably, $Y_1$, $Y_2$, $Y_3$ includes a moiety that links at least one functional group and at least one selectively cleavable functional group. The moiety may be, for example, selected from the group consisting of heteroatoms, alkyl, alkenyl, alkyne, where these may be cyclic and/or include further heteroatoms and functional substituents (such as carbonyl, carboxylic, amide, hydroxyl, ether, amine), or a combination of any of these.

$Y_1$ includes a selectively cleavable functional group, and typically will consist of a selectively cleavable functional group. Examples of $Y_2$ include: diethanolamine, propane-1, 2,3-tricarboxylic acid, cysteine, aspartic acid, asparagine, serine, tyrosine, arginine, histidine, threonine, lysine, glutamic acid and glutamine. Examples of $Y_3$ include: citric acid and tris(hydroxymethyl)aminomethane (Tris). The examples provided for $Y_1$, $Y_2$ and $Y_3$ are not intended to be an exhaustive list and the current invention contemplates other embodiments of $Y_1$, $Y_2$ and $Y_3$.

The skilled person would understand which compounds and methods are suitable for attaching A to X.

Preferably, A is a hydrophilic biologically active agent. For example, A is a biologically active agent with a log P value of less than 0. In other embodiments, A is an agent capable of being metabolised to a biologically active agent, the biologically active agent being hydrophilic with a log P value of less than 0. In one embodiment, A is itself a prodrug that is converted, for example, by hydrolytic, oxidative, reductive or enzymatic cleavage to the biologically active agent by one or more reactions or steps. When A is itself a prodrug, the general formula (I) may be considered to describe a compound referred to as a pre-prodrug.

In one preferred embodiment, the general formula (I) represents a compound according to the formula (II):

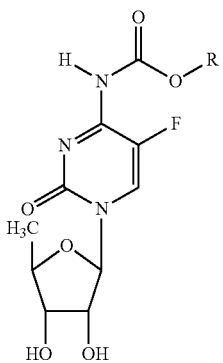
(II)

where R is as defined as in Formula (I), and is a functional group capable of conferring self-assembly properties to the compound.

The compound according to the formula (II) can be made as described in Scheme 1 below.

Particularly preferred embodiments of the self-assembled structures of the present invention comprise at least one compound selected from the following group: 5'-deoxy-5-fluoro-$N^4$-(3,7,11,15-tetramethyl-hexadecyloxycarbonyl)cytidine, 5'-deoxy-5-fluoro-$N^4$-(hexadecyloxycarbonyl)cytidine, 5'-deoxy-5-fluoro-$N^4$-(cis-9-octadecenyloxycarbonyl)cytidine, 5'-deoxy-5-fluoro-$N^4$-(octadecyl-1-oxycarbonyl)cytidine, and 5'-deoxy-5-fluoro-$N^4$-(cis-9,cis-12-octadecenyl-1-oxycarbonyl)cytidine. In other embodiments, the self-assembled structures of the present invention consist essentially of at least one compound selected from the following group: 5'-deoxy-5-fluoro-$N^4$-(3,7,11,15-tetramethyl-hexadecyloxycarbonyl)cytidine, 5'-deoxy-5-fluoro-$N^4$-(hexadecyloxycarbonyl)cytidine, 5'-deoxy-5-fluoro-$N^4$-(cis-9-octadecenyloxycarbonyl)cytidine, 5'-deoxy-5-fluoro-$N^4$-(octadecyl-1-oxycarbonyl)cytidine, and 5'-deoxy-5-fluoro-$N^4$-(cis-9,cis-12-octadecenyl-1-oxycarbonyl)cytidine.

In another preferred embodiment, A is dopamine.

Preferably, a prodrug of a general formula (I) is capable of forming a self-assembled structure having a lyotropic phase that displays lamellar, hexagonal, cubic or sponge morphologies. More preferably, the phase is a cubic, hexagonal, or sponge phase. More preferably still, the phase is an inverse phase.

In a second aspect of the invention there is provided self-assembled structures of the prodrugs of the general formula (I) of the above aspect.

Preferably, the self-assembled structure is a lyotropic phase that displays lamellar, hexagonal, cubic or sponge morphologies. More preferably, the phase is a cubic, hexagonal, or sponge phase. More preferably still, the self-assembled structure of the prodrug displays inverse phase morphologies. Generally inverse phases are advantageous as drug delivery vehicles because of their thermodynamic stability in excess water, greater surface area and controlled channel dimensions, the latter property being particularly important for release of active embedded within a self-assembled matrix. Accordingly, there is provided prodrugs that are capable of self-assembly into inverse lamellar, inverse cubic, inverse sponge or inverse hexagonal phases. The self-assembled structure may also be a solid lipid particle. The self-assembled structure of the prodrugs according to the current invention may be a bulk phase, or may be colloidal particles derived therefrom. Particularly preferred colloidal particles may be selected from the following group: cubosomes, hexosomes and "sponge" particles. Depending on conditions, more than one phase may be present in a self-assembled structure.

In a particularly preferred embodiment the self-assembled structures are of compounds of 5-fluorouracil prodrugs of the formula (II). Preferably, the self-assembled structures are solid lipid particles. Such particles may be suitably stabilised for pharmaceutical use by a surfactant stabiliser, such as polysorbate or poloxamer.

In a third aspect of the present invention there is provided a pharmaceutical composition for the treatment of a disease state comprising as an active ingredient self-assembled structures of Formula (I) or (II). In some embodiments, the pharmaceutical composition for the treatment of a disease state consists essentially of an active ingredient that is a self-assembled structures of Formula (I) or (II). In some embodiments, the self-assembled structures display a hexagonal, cubic or sponge phase. Preferably, the active ingredient is self-assembled structures of Formula (II) comprising a lamellar bulk phase or liposomal colloidal particles. In other embodiments, the self-assembled structures are solid lipid particles.

In some embodiments, the disease state is that of the presence of a tumor, and the pharmaceutical composition comprises as an active ingredient solid lipid particles or self-assembled structures of Formula (II).

The self-assembled structure/active ingredient is preferably present in the pharmaceutical composition in a therapeutically effective amount.

In a fourth aspect of the present invention there is provided a method for treatment of a disease state comprising administering a therapeutically effective amount of a pharmaceutical composition for the treatment of a disease state comprising as an active ingredient self-assembled structures of Formula (I) or (II) to a patient. In some embodiments, the self-assembled structures display a hexagonal, cubic or sponge phase. Preferably, the active ingredient is self-assembled structures of Formula (II), more preferably comprising a lamellar bulk phase or being liposomal colloidal particles. In other embodiments, the self-assembled structures are solid lipid particles.

In some embodiments, the disease state is that of the presence of a tumor, and in this case it is preferable that the pharmaceutical composition comprises an active ingredient of a self-assembled structure of Formula (II). The self-assembled structure may be a solid lipid particle.

In a fifth aspect of the present invention there is provided a self-assembled structure according to the current invention for the manufacture of a medicament for the treatment of a disease state. In some embodiments, the self-assembled structures display a hexagonal, cubic or sponge phase. Preferably, the prodrug or pre-prodrug forming the self-assembled structure is of Formula (II), in which case it is more that the self-assembled structure comprises a lamellar bulk phase or liposomal colloidal particles. In other embodiments, the self-assembled structures are solid lipid particles.

In some embodiments, the disease state is that of the presence of a tumor, and the self-assembled structure is of Formula (II). The self-assembled structure may be a solid lipid particle.

In a sixth aspect of the present invention there is provided a method of modulating the release of a biologically active agent or an agent capable of being metabolised to a biologically active agent, the method including covalently linking the biologically active agent or an agent capable of being metabolised to a biologically active agent to at least one tail component to form an amphiphile capable of self-assembling into a self-assembled structure stable under physiological conditions, and wherein the amphiphile is cleavable in vivo to release the biologically active agent or an agent capable of being metabolised to a biologically active agent in a biologically active form.

In one embodiment of this aspect there is provided a method of modulating the bioavailability of a biologically active agent or an agent capable of being metabolised to a biologically active agent, the method including covalently linking the biologically active agent or an agent capable of being metabolised to a biologically active agent to at least one tail component to form an amphiphile, wherein the link is cleavable in vivo to release the biologically active agent or an agent capable of being metabolised to a biologically active agent from the self-assembled structure; administering the amphiphile to a patient such that the amphiphile self-assembles into a self-assembled structure.

Preferably, the amphiphile self-assembles to form a self-assembled structure of a lyotropic phase that displays lamellar, hexagonal, cubic and/or sponge morphologies. More preferably, the amphiphile self-assembles into lamellar, inverse hexagonal or inverse cubic phases.

In one embodiment, the biologically active agent or an agent capable of being metabolised to a biologically active agent is a compound A as described for the above aspects.

In one embodiment, the tail component is an R group as described for the above aspects.

In some embodiments, the tail component is connected to the biologically active agent using a cleavable linker $Y_1$, $Y_2$ or $Y_3$ as described for the above aspects.

Preferably, the amphiphile is an enzymatic substrate for an enzyme that promotes formation of the biologically active form of the biologically active agent present in the amphiphile. That is, it is preferable that the amphiphile is predetermined to be one which may be acted upon by an enzyme present in the patient. More preferably, the enzyme acts on the cleavable linker. In embodiments where the biologically active agent is itself a prodrug, at least one further chemical modification step may then be necessary before the amphiphile is converted to the biologically active form.

A further aspect of the present invention relates to a process for preparing the bulk phase according to the current invention. There is further provided a bulk phase according to the current invention prepared by the process of this aspect.

A further aspect of the present invention relates to a process for preparing colloidal particles from a bulk phase according to the current invention. There is further provided colloidal particles prepared from a bulk phase according to the current invention by the process of this aspect.

It will be understood that the term "comprises" (or its grammatical variants) as used in this specification is equivalent to the term "includes" and should not be taken as excluding the presence of other elements or features.

DETAILED DESCRIPTION OF THE EMBODIMENTS

Figure 1:
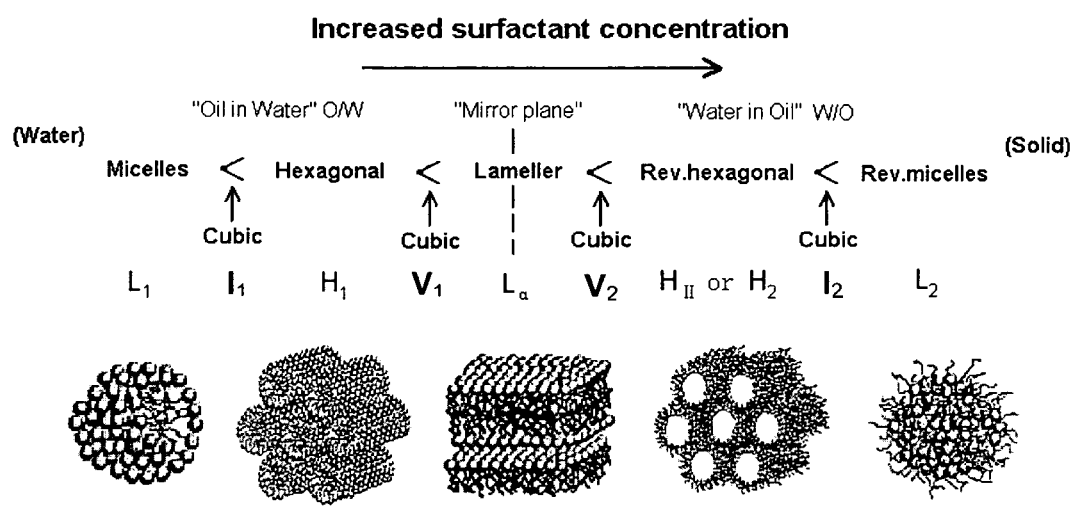
FIG. 1: Schematic picture of the different phases that can occur upon hydration of different amphiphiles. Abbreviations for different mesophases are micellar ($L_1$); micellar cubic ($I_1$), normal hexagonal ($H_1$), bicontinuous cubic ($V_1$), Lamellar ($L_a$), reversed bicontinuous cubic ($V_2$), reversed hexagonal ($H_2$), reversed micellar cubic ($I_2$), and reversed micellar ($L_2$), where subscripts 1 and 2 refer to "normal" and "reversed" phases, respectively.

It will be noted that various terms employed in the specification, examples and claims have meanings that will be understood by one of ordinary skill in the art. However, for clarity of meaning intended in this document, certain terms are defined below.

The term "prodrug" as used throughout the specification refers to a biologically active agent including structural modifications thereto, such that in vivo the prodrug is converted, for example, by hydrolytic, oxidative, reductive or enzymatic cleavage to the biologically active agent by one or more reactions or steps. It includes an agent that requires one or more chemical conversion steps or steps of metabolism to produce the active molecule—that is, this term is also understood to encompass "pre-prodrugs".

The term '5-fluorouracil prodrug' as used throughout the specification refers to a compound of the general formula (II) that is capable of being converted to 5-FU in vivo by, for instance, means of chemical and/or enzymatic modification.

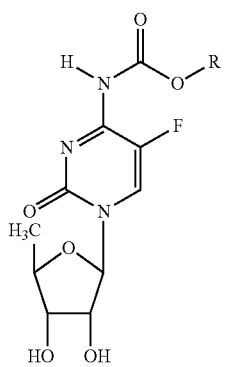

(II)

wherein R is as herein defined and $R_3$ and $R_4$ independently represent either hydrogen or easily hydrolysable radicals known to those skilled in the art. Such radicals include, but are not limited to, acetate, methyl ether, methoxymethyl ether, and silyl ethers.

The term "self-assembled structure" as used throughout the specification is meant to refer to an aggregate of amphiphiles that possess some degree of internal organisational order. The self-assembled structures may be formed by contacting the amphiphile with solvent. The self-assembled structure may refer to either a bulk lyotropic phase, a colloidal particle derived therefrom (a so-called "colloidosome"), or a solid lipid particle.

The term "bulk phase" as used throughout the specification is understood to mean a lyotropic phase that includes but is not limited to: micellar cubic ($I_1$); normal hexagonal ($H_1$); bicontinuous cubic ($V_1$); lamellar ($L_\square$); reversed bicontinuous cubic ($V_2$); reversed hexagonal ($H_2$); reversed micellar cubic ($I_2$) and sponge ($L_3$) phases.

The term "colloidal particle" as used throughout the specification is to be understood to refer to "colloidosomes" and solid lipid particles. The term "colloidosome" as used throughout the specification is to be understood to refer to a colloidal particle that possesses the same internal nanostructure of a bulk lyotropic phase. The term solid lipid particle as used throughout the specification is understood to mean a colloidal particle of the prodrug of the current invention, wherein the colloidal particle comprises a core of the neat prodrug and usually will be stabilised by a surface layer of surfactant. The neat prodrug core may be in a crystalline, microcrystalline, liquid crystalline or a non-crystalline form. It will be understood that the term "particle" refers to particles that may be nanoparticles or microparticles based on their average size. Often such particles are referred to as "solid lipid nanoparticles" although they may in fact be in a size range of microparticles. This form of self-assembled structure does not swell upon contact with excess solvent.

The term "hexagonal phase" as used throughout the specification is to be understood to mean an amphiphile phase consisting of long, rod-like micelles packed into a hexagonal array. A "normal hexagonal phase" is a hexagonal phase consisting of long, rod-like normal micelles, whilst an "inverse hexagonal phase" is a hexagonal phase consisting of long, rod-like inverse micelles. The normal hexagonal phase may be referred to as the "$H_I$ phase" and the inverse hexagonal phase may be referred to as the "$H_{II}$ phase". When a colloidosome possesses the internal structure of a bulk hexagonal phase the colloidosome may be referred to as a "hexosome".

The term "lamellar phase" as used throughout the specification is to be understood to mean a stacked bilayer arrangement, where opposing monolayers of the hydrophilic portion of amphiphile molecules are separated by a polar solvent domain, while the hydrophobic portion of the amphiphile molecule of the back-to-back layers are in intimate contact to form a hydrophobic layer. The planar lamellar phase is referred to as the "$L_\square$ phase".

The term "cubic phase" as used throughout the specification refers to two main classes of phases: micellar cubic and bicontinuous cubic. "Micellar cubic phase" refers to a phase consisting of spherical micelles arranged in a cubic array. A "normal micellar cubic phase" or "$I_I$ phase" consists of spherical normal micelles arranged in a cubic array, whilst an "inverse micellar cubic phase" or "$I_{II}$ phase" consists of spherical inverse micelles arranged in a cubic array. "Bicontinuous cubic phase" refers to a family of closely related phases that consist of a single curved lipid bilayer that forms a complex network that separates the polar solvent space into two continuous, but non-intersecting volumes. Bicontinuous cubic phases possess long range order based upon a cubic unit cell. Bicontinuous cubic phases have zero mean curvature; that is, at all points on surface of the amphiphile bilayer, the surface is as convex as it is concave. Bicontinuous cubic phases may be of the normal ("$v_I$ phase") or reverse ("$v_{II}$ phase") type. Several types of long range orientational orders have been observed for bicontinuous cubic phases; the orientational order in these phases correspond to space groups Ia3d, Pn3m, and Im3m. When a colloidosome possesses the internal structure of a bulk cubic phase the colloidosome may be referred to as a "cubosome".

The term "sponge phase" or "$L_3$ phase" as used throughout the specification refers to a phase that resembles a bicontinuous cubic phase, in that it possesses an amphiphile bilayer that separates the polar solvent space into two unconnected volumes, but it does not possess long range order. Accordingly, these phases are analogous to a "melted cubic phase".

The term "lattice parameter" as used throughout the specification means a set of lattice constants that define a unit cell of a crystalline solid or liquid crystal, and may include values such as the length of the unit cell.

The term "isoprenoid" as used throughout the specification is to mean an alkyl chain consisting of isoprene (2-methyl-1, 3-butadiene) monomers or subunits. The use of the term "isoprenoid" as used herein is intended to encompass unsaturated, partially saturated or fully saturated isoprene analogues and derivatives.

The term "pharmaceutical composition" as used throughout the specification means a composition comprising a therapeutically effective amount of at least one prodrug according to the current invention and at least one pharmaceutically acceptable carrier, excipient, diluent, additive or vehicle selected based upon the intended form of administration, and consistent with conventional pharmaceutical practices.

The terms "biologically active agent", "therapeutically active agent", "pharmaceutically active agent", "active agent" and "active ingredient" as used throughout the specification to refer to substances that are intended for, without limitation, the diagnosis, cure, mitigation, treatment, prevention and/or modification of a state in a biological system. Reference to a "biologically active agent" is broader than reference to a "therapeutically active agent". The terms "drug" and therapeutic agent are used interchangeably throughout this specification.

As used herein, "therapeutically effective amount" relates to the amount or dose of a drug such as a 5-fluorouracil prodrug or composition thereof that will lead to one or more desired effects, in particular the inhibition or cessation of tumour growth. A therapeutically effective amount of a substance will vary according to factors such as the disease state, age, sex, and weight of a subject, and the ability of the substance to elicit a desired response in the subject.

The abbreviation "5-FCPhy" as used throughout the specification refers to 5'-deoxy-5-fluoro-$N^4$-(3,7,11,15-tetramethyl-hexadecyl-1-oxycarbonyl)cytidine.

The abbreviation "5-FCPal" as used throughout the specification refers to 5'-deoxy-5-fluoro-$N^4$-(hexadecyl-1-oxycarbonyl)cytidine.

The abbreviation "5-FCOle" as used throughout the specification refers to 5'-deoxy-5-fluoro-$N^4$-(cis-9-octadecenyl-1-oxycarbonyl)cytidine.

The abbreviation "5-FCSte" as used throughout the specification refers to 5'-deoxy-5-fluoro-$N^4$-(octadecyl-1-oxycarbonyl)cytidine.

The abbreviation "5-FCLle" as used throughout the specification refers to 5'-deoxy-5-fluoro-$N^4$-(cis-9,cis-12-octadecadien-1-oxycarbonyl)cytidine.

The abbreviation "5-FCLln" as used throughout the specification refers to 5'-deoxy-5-fluoro-$N^4$-(cis-6, cis-9,cis-12-octadecatrien-1-oxycarbonyl)cytidine.

The abbreviation "5-FCSte" as used throughout the specification refers to 5'-deoxy-5-fluoro-$N^4$-(octadecyl-1-oxycarbonyl)cytidine.

The abbreviation "5-FCLeo" as used throughout the specification refers to 5'-deoxy-5-fluoro-$N^4$-(cis-9,cis-12-octadecenyl-1-oxycarbonyl)cytidine.

The abbreviation "CES" as used throughout the specification refers to an enzyme with carboxylesterase function.

It will be recognised by one skilled in the art that the formation of the desired lyotropic liquid crystalline phases of the current invention require a stringent balance between the specific hydrophilic and hydrophobic domains. Accordingly, the person of ordinary skill in the art will recognise that the selection of X in relation to A will dictate whether the prodrug of the current invention will form either the lyotropic phases and/or the solid lipid particles according to the current invention.

In general, the interplay between surfactant head group, tail and volume is very important in determining lyotropic phase behaviour. The relationship between the molecular geometry and phase behaviour can be described by the critical packing parameter (CPP). CPP is defined as CPP=$v/a_0 l_c$, where v is molecular volume, $a_0$ is the cross-sectional area of the surfactant head group, and $l_c$ corresponds to the hydrophobic tail length. Since the development of this formula, CPP has been used widely in predicting the mesophase behaviour based on the curvature of the molecule. For a molecule with a small head group and a bulky hydrophobe, the CPP value would be greater than 1, thereby inducing a mean negative interfacial curvature and potentially formation of an inverse mesophase.

The cleavable tail according to the current invention is selected based upon formation of a CPP greater than one when considered in context of the head group according to the current invention. FIG. 1 illustrates this interplay between the head and tail groups. The phases to the left of the lamellar phases have a critical packing density of less than 1 and often they happen at lower concentrations of the amphiphiles. The phases to the right of the lamellar phases have a CPP of more than 1 and usually occur at higher concentration of the amphiphiles. The CPP is not constant for an amphiphile molecule and changes with external factors such as temperature, pressure, concentration of the amphiphile and pH, as well as some additional solvents and additives. However, still this parameter can be used as a simple speculation of the phases that may occur upon hydration of the amphiphiles at room temperature or physiological temperature and at physiological pHs and pressure.

In addition to the phases shown in FIG. 1, less common phases can also occur upon hydration of amphiphiles such as sponge phase ($L_3$). This phase has a bicontinuous sponge-like structure with a lipid bilayer separating the polar solvent space into two unconnected sections similar to bicontinuous cubic phases. However, unlike cubic phases, sponge phases do not possess long range orders and their internal structure can be envisioned as a melted cubic phase.

A preferred embodiment according to the current invention is a self-assembled structure comprising the compounds according to formula (II) above.

The current invention contemplates that the biologically active agent A may itself be a prodrug instead of a drug or active. It will be recognised by the skilled addressee that in the compounds according to formula (II) above, A is a prodrug that undergoes modification in vivo to the biologically active agent, 5-fluorouracil. That is, A is a precursor to the biologically active agent formed in vivo after cleavage of the prodrug by, for instance, an enzyme.

Preferred embodiments of R include myristyl, palmityl, stearyl, oleyl, linoleyl, linolenyl, arachidonyl, phytanyl and H-farnasyl chains.

Particularly preferred embodiments of the compounds of the present invention are 5'-deoxy-5-fluoro-$N^4$-(3,7,11,15-tetramethyl-hexadecyl-1-oxycarbonyl) cytidine (5-FCPhy), 5'-deoxy-5-fluoro-$N^4$-(hexadecyl-1-oxycarbonyl)cytidine (5-FCPal), 5'-deoxy-5-fluoro-$N^4$-(cis-9-octadecenyl-1-oxycarbonyl)cytidine (5-FCOle), 5'-deoxy-5-fluoro-$N^4$-(octadecyl-1-oxycarbonyl)cytidine (5-FCSte), 5'-deoxy-5-fluoro-$N^4$-(cis-9,cis-12-octadecadien-1-oxycarbonyl)cytidine (5-FCLle), 5'-deoxy-5-fluoro-$N^4$-(cis-6, cis-9,cis-12-octadecatrien-1-oxycarbonyl)cytidine (5-FCLln), as used throughout the specification is understood to mean 5'-deoxy-5-fluoro-$N^4$-(octadecyl-1-oxycarbonyl)cytidine (5-FCSte), 5'-deoxy-5-fluoro-$N^4$-(cis-9,cis-12-octadecenyl-1-oxycarbonyl)cytidine (5-FCLeo), farnesoyl dopamine, or their pharmaceutically acceptable forms including solvates, hydrates, and salts.

The synthesis of the preferred compounds of the current invention may be carried out according to general methods known to those skilled in the art, for instance those disclosed in U.S. Pat. No. 4,966,891. In a particularly preferred embodiment, the compounds are prepared according to scheme 1:

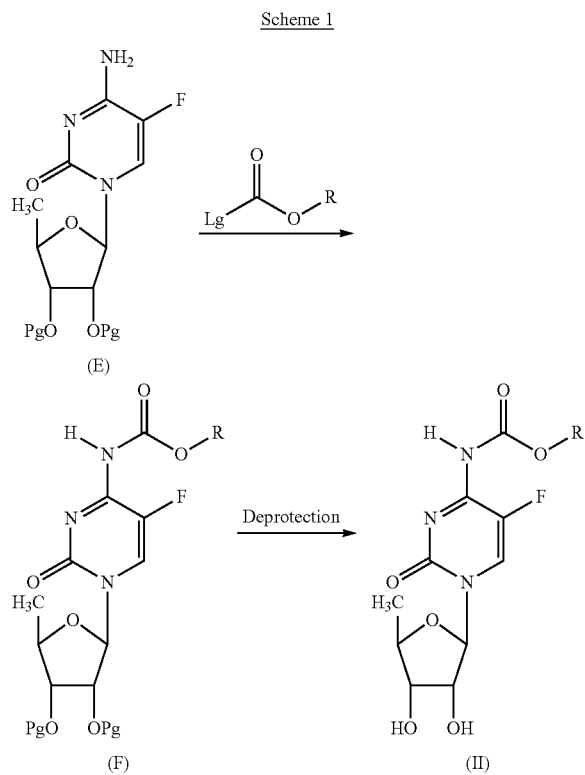

wherein R is defined as herein described; Lg is a leaving group that is preferably a halide or pseudohalide, and is most preferably chloride; and Pg is a protecting group that is preferably acetyl. The selection of the identity of the protecting group will readily be determined by one of ordinary skill in the art with a minimum amount of experimentation, and is also exemplified in the accompanying examples. The synthesis of starting material (E) is described in various publications such as, for example Shimma (Shimma 2000). Deprotection of the intermediate (F) to yield the 5-FU prodrug according to formula (II) may be carried out by methods known to those skilled in the art, following procedures described in references, such as, for example Wuts and Greene (Wuts 2007).

Reaction conditions for the synthesis of compounds according to the current invention would be readily determined by one of ordinary skill in the art with a minimum amount of experimentation, and are also exemplified in the accompanying examples.

The starting materials and reagents used to synthesise the compounds according to the current invention are either available from commercial suppliers such as, for example, the Aldrich Chemical Company (Milwaukee, Wis.), Bachem (Torrance, Calif.), Sigma Chemical Company (St. Louis, Mo.), Lancaster Synthesis (Ward Hill, Mass.), or are prepared by methods known to those of ordinary skill in the art, following procedures described in references such as Fieser and Fieser's *Reagents for Organic Synthesis* (Fieser 1991), *March's Advanced Organic Chemistry* (Smith 2001) and *Comprehensive Organic Transformations* (Larock 1999).

Another preferred embodiment according to the current invention is a self-assembled structure comprising according to formula (I), wherein A is dopamine. Accordingly, in this embodiment the structure of the compounds of the self-assembled structure may be described by formula (III):

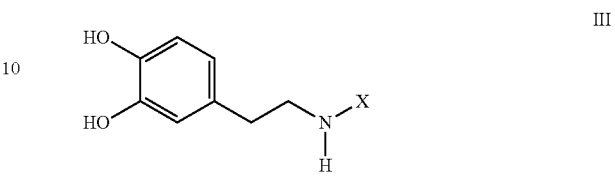

wherein X is defined for formula (I).

Preferred embodiments of R for the compounds according to formula (III) above include oleate and arachidonate.

The self-assembled structures of the current invention represent a desirable prodrug delivery system, owing to their modified release properties relative to prodrugs that do no undergo self-assembly into lamellar, inverse cubic, inverse hexagonal and sponge phases or alternatively solid lipid particles Without wishing to be bound by theory or mode of action, it is believed that the self-assembled structures of the current invention possess modified release properties firstly, due to the differences of the hydrolytic effect on the self-assembled amphiphile molecules and the complexity of access to single molecules in a self-assembly system compared with that of the isolated single molecules in non-assembled systems. Secondly, in the case of the preferred compounds it is believed that the hydrophobic tail R of the preferred prodrugs result in compounds with less favourable substrate activity for the first enzyme required to convert the prodrug, Capecitabine and its analogues to 5-FU, and thus resulting in a modified release profile for the compounds according to the current invention. Lastly, it is also believed that the hydrolysis of the compounds of the current invention releases fatty chain moieties that may, in themselves form self-assembled structures which in turn may alter the local environment of the enzymatic reaction and consequently affect enzymatic behaviour.

It is further similarly believed that the self-assembled structures according to the current invention are more desirable than prodrug self-assembled lyotropic structures that display micellar morphologies. The prodrug lyotropic hexagonal, cubic and sponge phases according to the current invention possess much greater amphiphile: solvent interface area than any of the previously disclosed prodrug self-assembled structures. Furthermore, unlike micelles, the inverse phases according to the current invention are stable in excess aqueous solvent.

In one embodiment, the self-assembled structures of the current invention comprise at least one solvent domain and at least one amphiphile domain, wherein the amphiphile domain comprises at least one of the compounds of according to formula (II), where R is defined as any functional group capable of conferring self-assembly properties to the prodrug.

The solvent domain of the current invention comprises at least one polar solvent. Examples of suitable solvents include solvents conventionally used for amphiphile self-assembly, such as, for example, but are not limited to the following: water, formamide, N-methylformamide, glycerol, ethylene glycol, propylene glycol, butylene glycol, N-methylacetamide, hydrazine and select ionic liquids such as ethylammonium nitrate; and mixtures thereof.

The solvent may also comprise other components, including e.g. salts, pH buffering agents, sugars such as glucose and sucrose. In addition to the amphiphilic prodrug the composition of the current invention may also comprise at least one other amphiphile that is capable of self-assembly behaviour. Amphiphiles capable of self-assembly behaviour are known to those skilled in the art and are described in various publications, such as, for example, Drummond and Fong (Drummond 1999) Laughlin (Laughlin 1996, 2000) the *Handbook of Lipid Research* (Small 1986). Examples of amphiphiles that are capable of self-assembly include, but are not limited to: surfactants, lipids, and block copolymers.

In another aspect according to the present invention, the self-assembled structure may include at least one other pharmaceutically active agent that is capable of being incorporated into the self-assembled structure. Pharmaceutically active agents that are capable of being incorporated into an amphiphile drug delivery vehicle are known to a person skilled in the art. See, for example, WO 2005/0210046 (DBL Australia Pty Ltd) and WO9830206. Examples of pharmaceutically or biologically active agents that may be incorporated into the vehicle include but are not limited to: globular proteins and glyoproteins, highly reactive lipids such as prostaglandins, bioactive large drug molecules such as proteins, polysaccharides, DNA and RNA and smaller drug molecules such as cyclosporine, paclitaxel, indomethacin, fenofibrate, progesterone, amphotericin B (AMB).

The self-assembled structures of the current invention may also comprise at least one other component intended to stabilise the self-assembled structure. Examples of stabilising reagents are triblock copolymers of PEG-PPO-PEG of different building blocks and more specifically poloxamer 407, as well as PEG lipid stabilising reagents such as polysorbate (for example, polysorbate 80).

Bulk Phases

In one aspect, the self-assembled structure of the current invention comprises at least one bulk lyotropic phase.

The bulk lyotropic phase of the current invention comprises at least one phase selected from the following group: lamellar, normal hexagonal, normal micellar cubic, normal bicontinuous cubic, inverse bicontinuous cubic, $L_3$ 'sponge', and inverse hexagonal. Preferably, the bulk phase comprises at least one phase selected from the group consisting of inverse hexagonal, inverse cubic phase, L3 'sponge' phase and lamellar phases. Most preferably, the bulk phase comprises inverse hexagonal and inverse cubic phase.

In a preferred embodiment, the bulk lyotropic phases according to the current invention may be readily produced at a temperature range of about room temperature to about 50° C. and be stable within this temperature range for at least several months.

A preferred embodiment according to the current invention are bulk lyotropic inverse phases. The thermodynamic stability of the lyotropic phases to dilution in excess aqueous solvent means that the bulk phase maintains its primary higher ordered structure, although the lattice parameter might be changed due to the swelling of the amphiphile in water. Most preferably, the lyotropic phase according to the current invention is an inverse bicontinuous cubic phase.

It will be recognised by one skilled in the art that the observed lyotropic phase is dependent upon temperature. The bulk phases according to the current invention are stable between room temperature and physiological temperature, are preferably stable at temperatures from about 35 to about 40° C. and are most preferably stable from about 35 to about 37° C.

Processes for preparing bulk phases according to the current invention are known to those skilled in the art. In one embodiment, bulk phases according to the present invention may be prepared by mixing each amphiphile in an appropriate buffer to the appropriate concentration. Examples of appropriate buffers include but are not limited to physiologically acceptable buffers, such as, for example, phosphate, phosphate buffered saline (PBS), tris(hydroxymethyl)aminomethane (Tris), 4-(2-hydroxyethyl)-1-piperazineethanesulfonic acid (HEPES), Tris-sucrose, Tris-glycine, and glycine buffers.

In another embodiment, the preferred inverse cubic phases according to the current invention are prepared by mechanically mixing molten lipid between room temperature and 50° C. until an optically clear and visually homogenous sample are obtained. Optionally, addition of a co-solvent such as, for example, ethanol in the range of 10-20% by weight may assist the homogenisation process.

Colloidal Particles: Colloidosomes

A further aspect of the invention relates to self-assembled structures of the current invention that comprise one or more particles that retain the internal structure of the bulk phase. Such particles are referred to as "colloidosomes".

In one embodiment, the self-assembled structures of the current invention comprise colloidosomes selected from the following group: cubosomes, hexosomes and "sponge" type particles. In a preferred embodiment, the colloidal particles are selected from the following group: cubosomes and hexosomes; most preferably, the colloidal particles are cubosomes. The invention also includes liposomes of compounds according to Formula (II).

In a particularly preferred embodiment according to the current invention, the colloidosomes are derived from an inverse phase. The thermodynamic stability of the lyotropic phases according to the present invention means that the bulk phases can progressively be diluted in excess aqueous solvent and dispersed into colloidosomes while maintaining the same liquid crystalline structures as that of bulk phases.

The colloidosomes according to the current invention may be prepared according to processes known to those skilled in the art. For example, colloidosomes may be prepared by hydration of a thin lipid film in water or saline solution (e.g., phosphate buffered saline). In addition sugars such as glucose and dextrose might be added to the media. Reverse phase colloidosomes such as inverse cubosomes and hexosomes may be hydrated in water to form gel like bulk phases that can be consequently dispersed into particles by using shear forces such as sonication and high pressure homogenisation in the presence of stabilising agents.

It will be recognised by one of ordinary skill in the art that in order to prepare stable colloidosomes it is necessary to add a stabilisation agent or fragmentation agent. Suitable fragmentation agents are known to those skilled in the art and include, for example, poloxamer or polysorbate. Poloxamer is the most widely used stabilising agents for inverse phase colloidosomes and is a block copolymer of polyethylene glycol (PEG) and polypropylene oxide (PPO). In a preferred embodiment according to the current invention, the stabilising agent are triblock copolymers of PEG-PPO-PEG of different building blocks. In a particularly preferred embodiment according to the current invention, the stabilisation agent is poloxamer 407. In another embodiment, the stabilisation agent is a non-ionic block copolymer surfactant terminated with primary hydroxyl groups, sold under the trade name Pluronic® F127 by BASF AG. This stabilisation agent is referred to simply as "F127" hereinafter.

In one embodiment, colloidal particles are prepared by dispersing a bulk phase. The bulk phases of the current invention may be dispersed by dropwise addition of an ethanolic solution of the bulk phases into water containing a stabilising reagent. Alternatively, the bulk phase may be dispersed by adding water containing at least one stabilising reagent to the bulk phases. The size of these particles can be controlled by means of vortexing, sonication, filtration, extrusion and homogenisation, techniques well known to one skilled in the art.

In a preferred embodiment, colloidosome dispersions according to the current invention are prepared by dissolving an appropriate amount of the neat amphiphile prodrug and a surfactant in a water miscible solvent. The water miscible solvent may be one or more solvents selected from the group consisting of ethanol, propanol, and butanol; is preferably ethanol and propanol and is most preferably ethanol. The prodrug-surfactant mixture is well mixed under vortex until the solvent-surfactant-prodrug mixture is homogeneous. Optionally, the mixture may be heated to facilitate dissolution of the prodrug and surfactant into the water miscible solvent in temperatures <50° C. The dissolved mixture is then added in a controlled manner to an aqueous solution. Preferably, the aqueous solution is water. Preferably, the prodrug-surfactant mixture is added dropwise to water. Preferably, the water to which the mixture is being added is agitated; most preferably, the water is being agitated by means of a vortex.

The coarse colloidosome prepared according to this embodiment may optionally be subject to one or more additional processing steps. Such processing methods are known to those skilled in the art and include, for example, sonication, probe sonication, high pressure homogenisation, and stepwise extrusion through membranes. The membranes employed for stepwise extrusion may possess pore sizes including, for example, 0.8, 0.4, 0.2, 0.1 and 0.05 µm. In one embodiment, the processing step is a size selection process.

In a preferred embodiment, the course colloidosome preparation is further processed by means of passing through a series of polycarbonate (PC) membranes. The size range of the membranes will be selected by a person skilled in the art according to the desired particle size of the final product. The equipment which may be used for this processing step are known to those skilled in the art, but may include, for example, a mini-extruder.

It will be recognised by the skilled addressee that the size of the colloidosomes of the current invention will depend upon the intended use. For example, for intravenous administration the preferred colloidosome size range is commonly between about 30 nm and about 10 µm. More preferably, the size range is between about 30 nm and about 1 µm for intravenous application.

For delivery of colloidosomes into specific organs such as liver and passive targeting to tumours, particle sizes of between about 30 nm to about 1000 nm are contemplated. More preferably particle sizes are about 30 nm to less than about 500 nm. Particularly preferred are colloidal particles of sizes between about 30 nm to about 300 nm. Without wishing to be bound by theory, it is believed that particles of the size between 30-300 nm are passively targeted to cancer cells, owing to their enhanced permeation and retention time in the leakier and chaotic neovasculature of solid tumours. See, for example Brannon-Peppas L. et al (Brannon-Peppas 2004).

Figure 3:
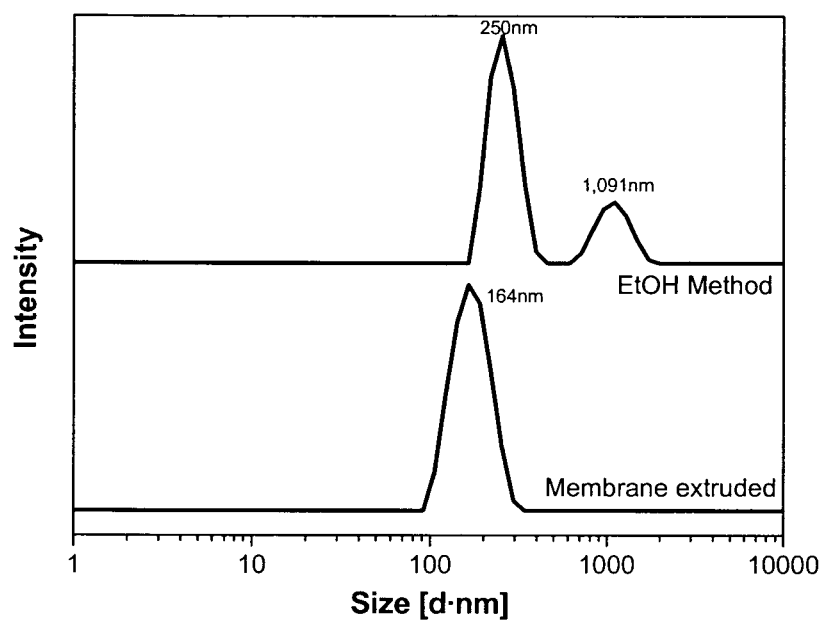
FIG. 3: Particle size distribution (diameter in nm) as determined by DLS of 5-FCPhy/F127/ethanol dispersions. Upper curve represents the coarse dispersions formed directly using ethanol method. Bottom curve is the size distribution after size controlled membrane extrusion.

In one embodiment depicted in FIG. 3, a coarse (unprocessed) dispersion of 5-FCPhy/F127/ethanol particles according to the current invention displays a bimodal average size distribution. In another embodiment depicted in FIG. 3, particles of 5-FCPhy/F127/ethanol after treatment with a controlled membrane extrusion process have the illustrated size distribution of 100-300 nm, averaging at 164 nm. In an alternative embodiment depicted in FIG. 4, a coarse dispersion of 5-FCOle/F127/ethanol particles according to the current invention have a trimodal size distribution. In another embodiment depicted in FIG. 4, particles of 5-FCOle/F127/ethanol after treatment with a controlled membrane extrusion process have a size distribution of 150-500 nm, average size of 255 nm as illustrated.

Colloidal Particles: Solid Lipid Particles

In another embodiment, the self-assembled structure according to the present invention is a solid lipid particle.

A preferred aspect of the current invention seeks to provide solid lipid particles comprised of at least one 5-fluorouracil prodrug. Solid lipid particles according to the current invention may be manufactured by processes known to those skilled in the art. See, for example, Mehnert and Mäder. (Mehnert 2001)

The appropriate process used to manufacture solid lipid particles according to the current invention may be selected according to the physicochemical properties of the prodrug of the current invention. It will be recognised by one skilled in the art that some of the typical methods to manufacture solid lipid particles, for example those methods that require the lipid to be melted whilst in an aqueous solution, are not applicable to the prodrugs according to the current invention that possess a melting point higher than 100° C.

In one embodiment, the solid lipid particles of the current invention are prepared according to mechanical methods. According to this embodiment, one or more stabilisers are added to the neat amphiphile. Examples of stabilisers include, but are not limited to: triblock polymers (for example, poloxamer 407). The amount of stabiliser added to the neat amphiphile may be between about 1-10% (w/w). Depending on the nature of the amphiphile and the stabiliser, the amount of stabiliser added may be between about 5-10% (w/w). Optionally, other additives may be added to the amphiphile. Other additives are known to those skilled in the art and may include, for example ethanol, propanol and butanol to ease the high viscosity of the bulk phases. The amphiphile mix is then melted, and water is added to the melted amphiphile mixture. To prepare the initial bulk phases, usually 20-30% of water by weight is added to the amphiphile, usually at room temperature (about 22 to about 25° C.). The amphiphile-water mixture is then sheared using methods known to those skilled in the art. In a preferred embodiment, the amphiphile-water mixture is sheared using rough homogenization. The mixture may then undergo further processing to produce particles of desirable size and polydispersity. Methods of further processing are known to those skilled in the art and may include, for example, high pressure homogenization, ultrasonication, and filtration through different membranes with known pore sizes.

The average size and size distribution of the solid lipid particles according to the current invention are similar to those described for the colloidosomes according to the current invention. In one embodiment, depicted in FIG. 2, the particles display the size distribution of 350-1100 nm as illustrated.

Pharmaceutical Compositions

A further aspect of this invention relates to pharmaceutical compositions of the current invention. In one embodiment, the pharmaceutical composition according to the present invention comprises at least one of compounds according to formula (I) or formula (II). In another embodiment, the pharmaceutical composition comprises at least one self-assembled structure according to The current invention. In a further embodiment, the composition comprises at least one of the solid lipid particles of the current invention.

In one embodiment, the pharmaceutical composition according to the current invention may be freeze-dried, spray freeze dried, lyophilised or spray-dried powder.

Pharmaceutical compositions according to the present invention may include pharmaceutically acceptable carriers, excipients, diluents, additives and vehicles selected based upon the intended form of administration, and consistent with conventional pharmaceutical practices. Suitable pharmaceutical carriers, excipients, diluents, additives and vehicles are known to those skilled in the art and are described in publications, such as, for example *Remington: The Science and Practice of Pharmacy*.

The pharmaceutical compositions according to the present invention may further include adjuvants that include, but are not limited to: preservatives, wetting agents or antimicrobial agents. Other adjuvants include but are not limited to: cryoprotectants, spray drying adjuvants, buffers, isotonically adjusting agents, and pH adjusting materials.

The amount of active ingredient that may be combined with the carrier materials to produce a single dosage form will vary depending upon the host treated and the particular mode of administration. Dosage unit forms will generally contain between from about 1 mg to about 5,000 mg of an active ingredient, preferably contain between 20 and 1,000 mg of an active ingredient, and most preferably between 100 and 750 mg of an active ingredient.

It will be understood that reference to the mass of the active ingredient refers to the mass of the prodrug, and not the mass of self-assembled structures or solid lipid particles thereof.

Methods of Treatment

Another aspect of this invention relates to use of a self-assembled structure, solid lipid particle or pharmaceutical compositions thereof according to the present invention for the inhibition of tumour growth. In yet another aspect there is provided a method comprising administering to a subject in need thereof a therapeutically effective amount of a composition including a prodrug according to formula (I), (II) or (III). In yet another aspect there is provided a use of a composition including a prodrug according to formula (I), (II) or (III) in the manufacture of a medicament for administration to a subject in need thereof in a therapeutically effective amount.

In a preferred embodiment, a pharmaceutical composition of the current invention is used to inhibit growth of solid and metastatic tumours. In a particularly preferred embodiment, a pharmaceutical composition according to the current invention is used to inhibit growth of solid or metastatic tumours associated with colon cancer, colorectal cancer or breast cancer.

It will be recognised that the intended form of administration of the self-assembled structure will be as either its bulk phase, as colloidal particles derived therefrom or as solid lipid particles.

The dosage regimen of a self-assembled structure, solid lipid particle or pharmaceutical compositions thereof according to the current invention will vary depending upon known factors such as the pharmacodynamic characteristics of the compounds, self-assembled structures, colloid particles and compositions thereof of the current invention, and their mode and route of administration; the age, sex, health, medical condition, and weight of the patient, the nature and extent of symptoms, the kind of concurrent treatment, the frequency of treatment, the renal, hepatic and cardiovascular and otherwise general health status of the patient in need of such treatment, and can readily be determined by standard clinical techniques.

It will be understood that the invention disclosed and defined in this specification extends to all alternative combinations of two or more of the individual features mentioned or evident from the text or drawings. All of these different combinations constitute various alternative aspects of the invention.

The examples that follow are intended to illustrate but in no way limit the present invention.

Example 1

Synthesis of 5-FU Prodrugs

The general scheme for the synthesis of various prodrug amphiphiles with varying hydrophobic chains used in this invention are shown in Scheme 2.

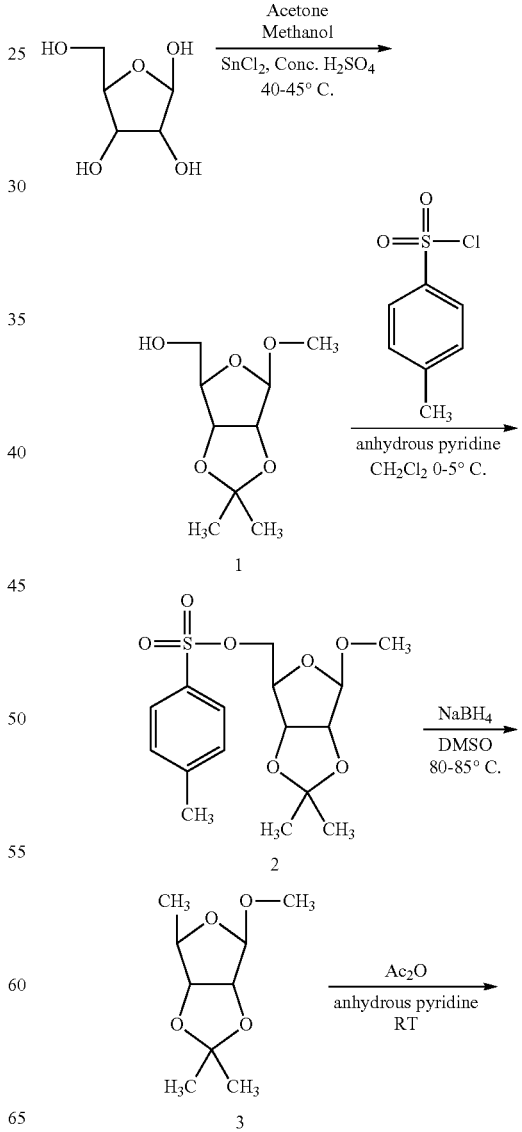

Scheme 2

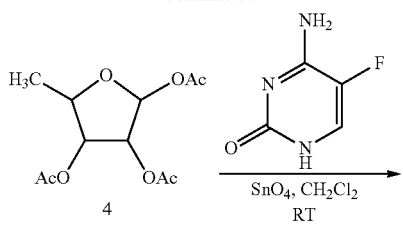

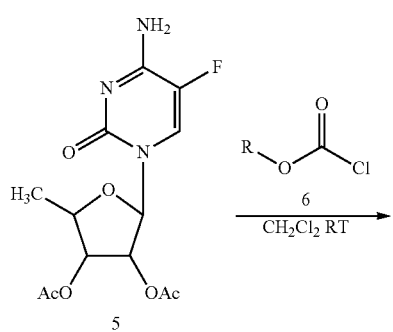

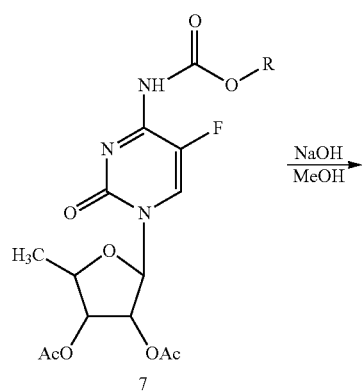

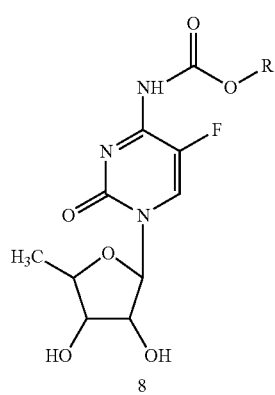

R: a) 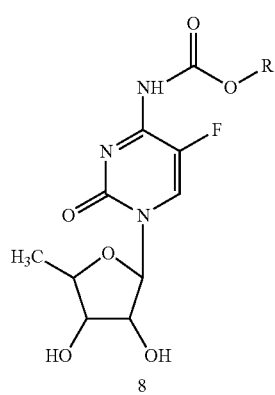

b)

c)

Materials:

Materials and solvents were supplied from Sigma-Aldrich with analytical or spectroscopic grade and used without further modification.

Nuclear Magnetic Resonance (NMR):

The $^1$H NMR spectra (200 MHz) were recorded on a Bruker AC200 spectrometer in deuterated solvent with Tetramethylsilane (($CH_3$)$_4$Si, TMS) as internal standard unless otherwise stated. Solute concentrations were approximately 10 mg/ml in standard 5 mm NMR tubes. The $^{13}$C NMR spectra (500 MHz) were obtained from Bruker AC400 in $CDCl_3$. The spectra were analysed using MestRe-C 2.3a software. The chemical shift values (δ) were expressed in ppm, coupling constants were expressed as J values, in Hertz units.

High Performance Liquid Chromatography (HPLC) and Ultra Performance Liquid Chromatography (UPLC):

Analytical HPLC was performed on Waters HPLC equipment (Waters Corporation, Milford, Mass., USA), comprising of a 600 solvent delivery system with a 600 automated gradient controller using a Phenomenex Gemini C18 column (5 μM, 4.6×150 mm) and an Altech 2000 Evaporative Light scattering Detector (ELSD). The mobile phases consisted of an isocratic 70% methanol and 30% water solvent system with 1.00 mL/min pumping rate. UPLC was carried out on Waters Acquity UPLC BEH™ equipped with a C18 column (1.7 micron) 50 mm×2.1 mm. The mobile solvent system was ethanol water with 0.4 ml/min flow rate, solvent A was water/ethanol 90/10, and solvent B was 100% ethanol. At first 2 min, the gradient run from 100% A to 100% B, then the gradient remained as 100% A. The total running time was 5 min for UPLC. The results for HPLC and UPLC were recorded on both ELSD and UV-Vis (λ=260 nm) detectors.

Flash Column Chromatography:

Flash column chromatography was used for purification of most synthesized compounds. Columns was prepacked with SiOH (40-63 μm) purchased from Buchi. The eluting fractions were tested on thin layer chromatography (TLC) aluminium plates precoated with silica gel 60 containing fluorescent indicator ($F_{254}$). Compounds on the TLC plates were visualized by dipping into 3% phosphomolybdic acid in ethanol solution, followed by charring on a hot spot. Mass spectra were recorded on Thermo Finnigan LC-MS with atmospheric pressure chemical ionization (APCI) source in the positive (+) ion mode. Samples were usually introduced dissolved in DCM. Solvents were removed using a rotary evaporator under reduced pressure with water bath temperature below 50° C.

Synthesis of
5-deoxy-1,2,3-tri-O-Acetyl-β-D-ribofuranoside (4)

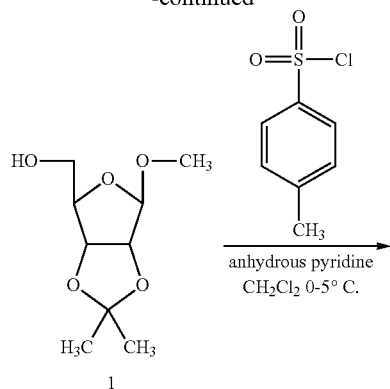

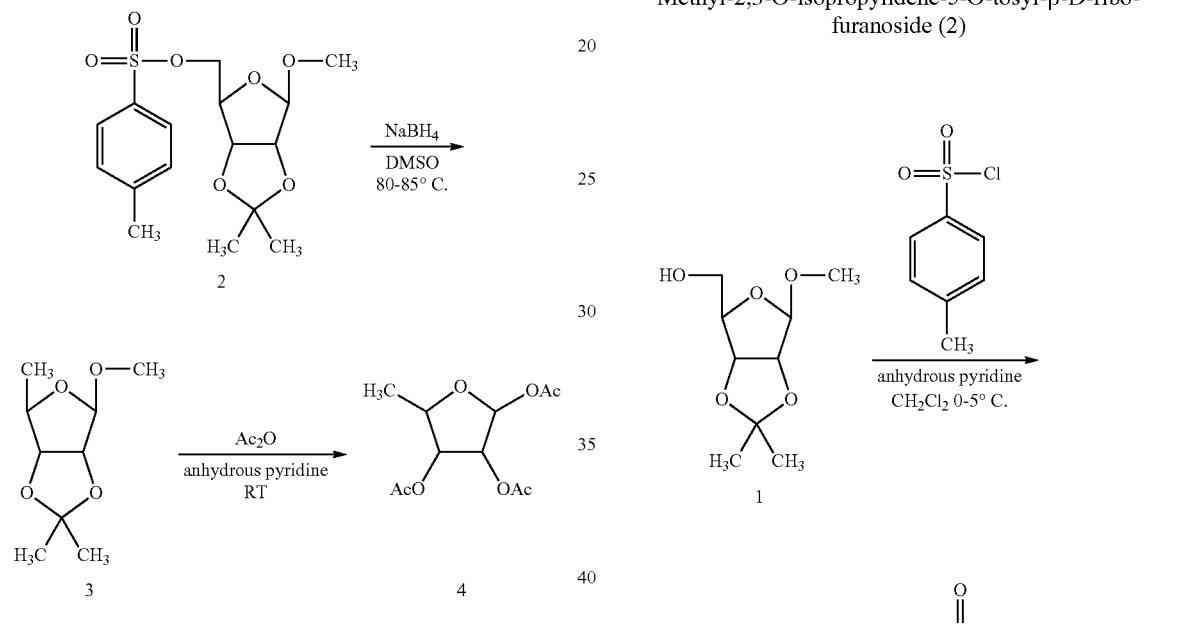

Methyl-2,3-O-isopropylidene-β-D-ribofuranoside (1)

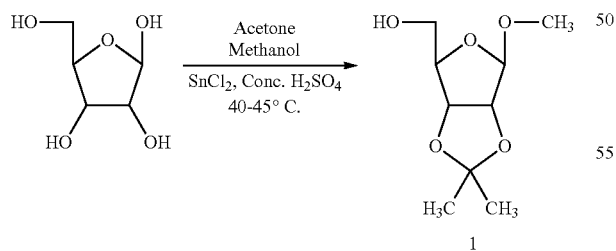

Powdered D-ribose (60 g, 400 mmol) and SnCl$_2$.2H$_2$O (90 g, 400 mmol) were suspended in a mixture of acetone (600 ml) and methanol (156 ml). A catalytic amount of concentrated H$_2$SO$_4$ (4.24 g, 2.3 ml) was added dropwise into the solution. Then the mixture was heated and stirred at 40-45° C. overnight. After the reaction completed, the resulting mixture was filtered through filter paper and the filter cake was washed with a mixture of acetone and methanol (1:1 mixture, 100 ml). Then the filtrate was neutralized (pH 6-7) with saturated NaHCO$_3$ aqueous solution. The resulting milky solution was once again filtered through filter paper. Both acetone and methanol in the filtrate were then removed under reduced pressure. The aqueous solution thus obtained was extracted with ethyl acetate (EtOAc), the combined organic layers were washed with brine (saturated NaCl solution), dried with Na$_2$SO$_4$ and evaporated in vacuo to yield methyl-2,3-O-isopropylidene-β-D-ribofuranoside as yellow oil (54.20 g, 66.4% yield). $^1$H NMR (CDCl$_3$): δ 1.31 and 1.48 (2s, each 3H, CMe$_2$), 3.25 (br s, 1H, OH), 3.44 (s, 3H, —OMe), 3.62 (dd, 1H, J=3.2 Hz, CH$_2$), 3.68 (dd, 1H, J=2.8 Hz, CH$_2$), 4.44 (t, 1H, J=2.6 Hz, H-4), 4.60 (d, 1H, J=5.7 Hz, H-2), 4.83 (d, 1H, J=5.6 Hz, H-3), 4.97 (s, 1H, H-1).

Methyl-2,3-O-isopropylidene-5-O-tosyl-β-D-ribofuranoside (2)

To a cold solution containing Methyl-2,3-O-isopropylidene-β-D-ribofuranoside (1) (108.4 g, 531 mmol) in CH$_2$Cl$_2$ (1000 ml) dropwise adding 300 ml of toluene-4-sulfonyl chloride (140 g, 734 mmol) in anhydrous pyridine solution. With vigorous stirring, the reaction was carried out at 0-5° C. for 20 h. The resulting solution was washed with NaHCO$_3$ aqueous solution, brine and evaporated to yield a syrupy mass (185 g, 97.2%), which can be further crystallized from hexane and dried under high vacuum to give pure methyl-2,3-O-isopropylidene-5-O-tosyl-β-D-ribofuranoside (138.8 g, 72.86% yield) as a white solid crystals. $^1$H NMR (CDCl$_3$): δ 1.28 and 1.45 (2s, each 3H, CMe$_2$), 2.46 (s, 3H, aromatic Me), 3.24 (s, 3H, —OMe), 4.01 (d, 2H, J=7.2 Hz, H-5), 4.31 (dt, 1H, J=7.3 Hz, H-4), 4.53 (d, 1H, J=6.0 Hz, H-2), 4.60 (dd, 1H, J=5.6 Hz, H-3), 4.93 (s, 1H, H-1), 7.36 (d, 1H, J=8.0 Hz, aromatic H), 7.81 (d, 2H, J=8.2 Hz, aromatic H).

Methyl-2,3-O-isopropylidene-5-deoxy-β-D-ribofuranoside (3)

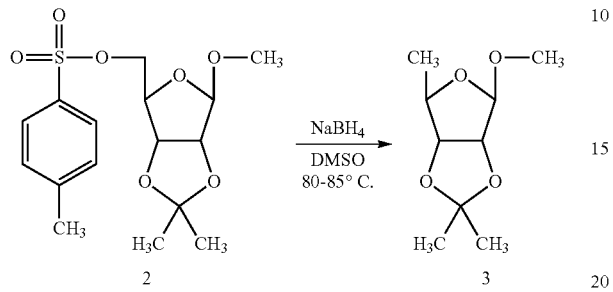

20 g of sodium borohydride (NaBH$_4$) was reacted with crude methyl-2,3-O-isopropylidene-5-O-tosyl-β-D-ribofuranoside (2) (50 g, 140 mmol) in 400 ml of dimethyl sulfoxide solution for 20 h at 80-85° C. After cooling the flask to room temperature, the reaction mixture was poured into 400 ml of 1% aqueous acetic acid solution and stirred for 30 min. The residue was extracted with chloroform and the collected organic layer was washed with sufficient amount of water. After dried with anhydrous magnesium sulfate, chloroform was removed under reduced pressure to give a crude compound with light yellow colour. The main biproduct of this reaction was methyl-2,3-O-isopropylidene-β-D-ribofuranoside (1) due to the hydrolysis of sulfonyl group. The crude compound was further purified and yielded 20.2 g of methyl-2,3-O-isopropylidene-5-deoxy-β-D-ribofuranoside (3) (71.8%) as a clear colourless liquid upon distillation. $^1$H NMR (CDCl$_3$): 1.27 and 1.48 (2s, each 3H, CMe$_2$), δ1.31 (d, 3H, J=1.5 Hz, H-5), 3.33 (s, 3H, OMe), 4.35 (q, 1H, J=7.7 Hz, H-4), 4.51 (d, 1H, J=5.4 Hz, H-2), 4.64 (d, 1H, J=5.8 Hz, H-3), 4.94 (s, 1H, H-1).

1,2,3-tri-O-acetyl-5-deoxy-β-D-ribofuranose (4)

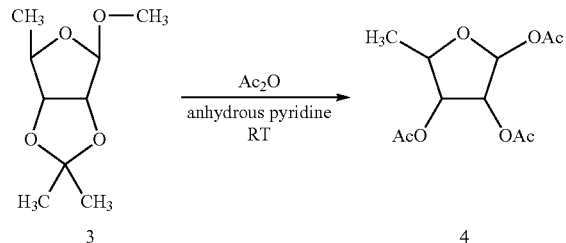

To compound 3 (30 g, 148 mmol), added sulfuric acid solution (0.04 N, 360 mL), and heated to 80-90° C. for 17 h. When the mixture was cooled to room temperature, solid Na$_2$CO$_3$ was added to neutralize the solution to pH 7.0, and then evaporated to dryness. The residue was then dissolved in anhydrous pyridine (350 ml), treated with acetic anhydride (150 ml, 1.58 mol), and stirred at room temperature for 16 h. Saturated NaHCO$_3$ (1 L) was poured into the reaction mixture and stirred at room temperature for 1 hour to remove the excess amount of acetic anhydride. Then the mixture was extracted with CH$_2$Cl$_2$ three times, and the combined organic layer was washed with water, dried over Na$_2$SO$_4$, and evaporated in vacuo to provide a mixture of the two anomers of 1,2,3-tri-O-acetyl-5-deoxy-D-ribofuranose (27.9 g, 72.4% yield) as a brown liquid. The anomeric mixture was purified by flash column chromatography on silica gel with cyclohexane-ethyl acetate (70:30), then the pure white crystals of β anomer (4.65 g, 12.1% yield) were obtained from crystallization with ethyl acetate-hexane. $^1$H NMR (CDCl$_3$) of pure 1,2,3-tri-O-acetyl-5-deoxy-β-D-ribofuranose (4): δ1.37 (d, 3H, J=6.3 Hz, H-5), 2.08, 2.10, 2.12 (3s, each 3H, OMe), 4.28 (m, 1H, J=6.5 Hz, H-4), 5.10 (dd, 1H, J=6.7 Hz, H-2), 5.34 (dd, 1H, J=4.8 Hz, H-3), 6.11 (d, 1H, J=1.0 Hz, H-1).

Synthesis of 2',3'-Di-O-acetyl-5'-deoxy-5-fluorocytidine (5)

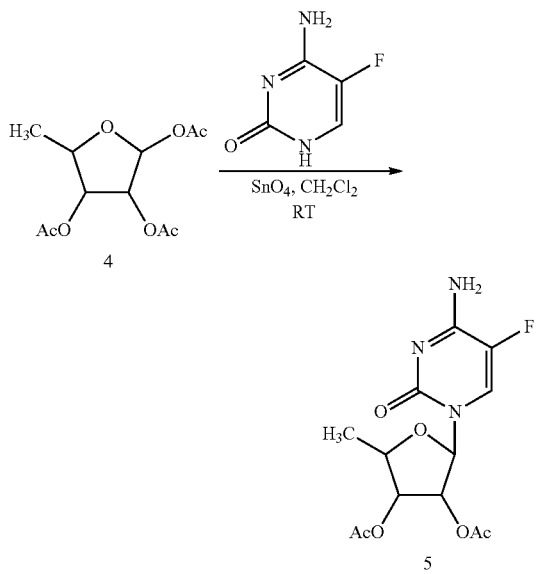

5-Fluorocytosine (2.42 g, 18.8 mmol) was suspended in toluene (10 ml) and hexyamethyl-disilazane (3.03 g, 18.8 mmol). The mixture was heated at 100° C. overnight. After concentrating the reaction mixture under reduced pressure, methylene chloride (30 ml) and 5-deoxy-1,2,3-tri-O-Acetyl-β-D-ribofuranoside (4) (5.16 g, 18.8 mmol) were added to the residue. Then, anhydrous stannic chloride (4.90 g, 18.8 mmol) was added dropwise to the ice-cooled reaction mixture over a period of 20 min. After stirring the mixture at room temperature for an additional 2 h, sodium bicarbonate (10 g) was added, followed by the dropwise addition of water (20 ml). After stirring the resulting mixture at room temperature overnight, 4% sodium bicarbonate solution was poured into the reaction mixture and stirred for additional 1 h. The mixture was then extracted with water-methylene chloride. The organic layer was collected, dried with Na$_2$SO$_4$, the solvent was removed under reduced pressure to give brown syrup. The residue was then partially purified by silica gel chromatography using CH$_2$Cl$_2$:MeOH (5:1) as an eluent to yield crude target compound (5) (4.455 g, 13.5 mmol, 72%). $^1$H NMR in DMSO-d$_6$: δ1.34 (d, 3H, J=6.4 Hz, H-5), 2.05, 2.06 (2s, each 3H, OMe), 4.14 (q, 1H, J=5.0 Hz, H-4), 5.10 (t, 1H, J=6.4 Hz, H-2), 5.43 (dd, 1H, J=6.31 Hz, H-3), 5.77 (dd, 1H, J=1.0 Hz, H-1), 7.71 (br s, 1H, N—CH═C—F), 7.97 (br s, 1H, NH), 8.02 (d, 1H, J=7.0 Hz, NH).

Synthesis and Characterisation of 5'-deoxy-5-fluoro-
$N^4$-(3,7,11,15-Tetramethyl-hexadecyloxycarbonyl)
cytidine (8a)-5FCPhy
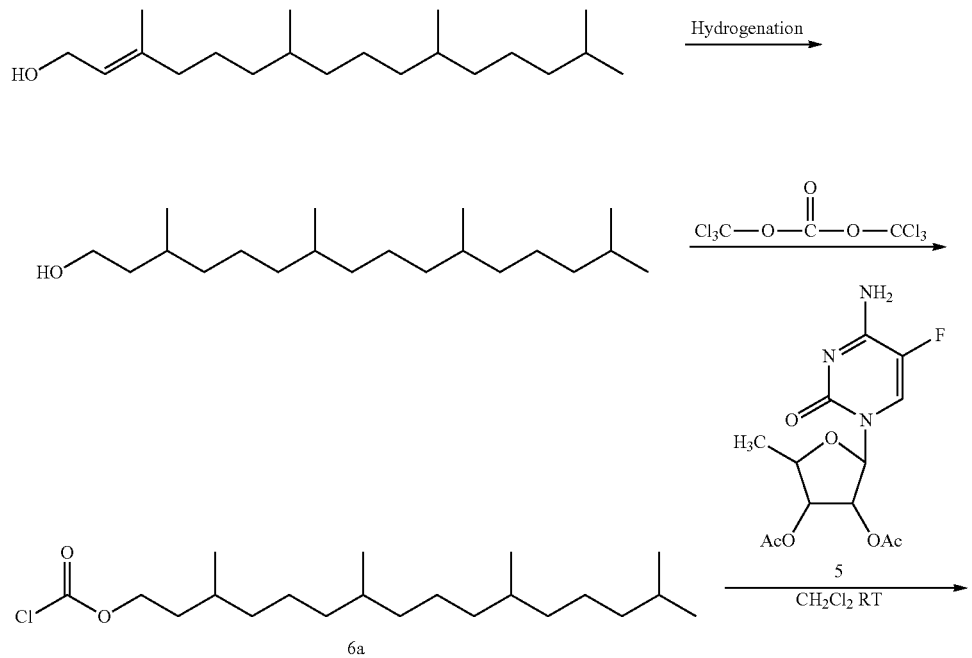
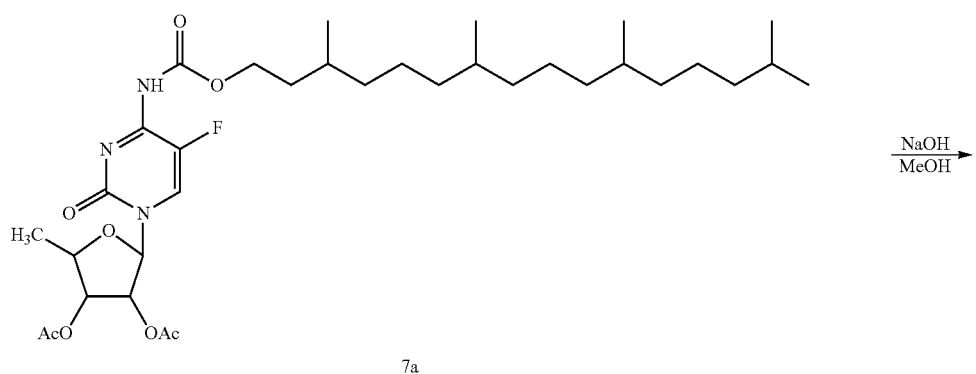
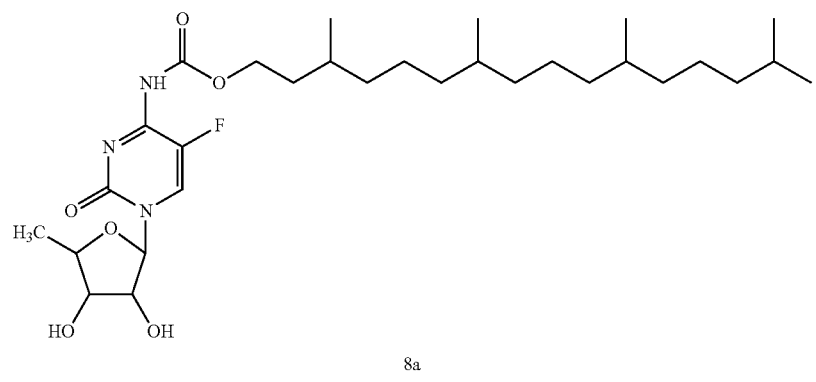

3,7,11,15-Tetramethyl-hexadecyl chloroformate (6a)

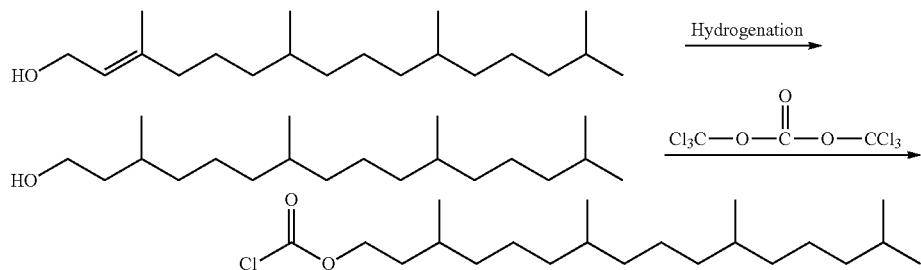

3,7,11,15-Tetramethyl-hexadecane-1-ol

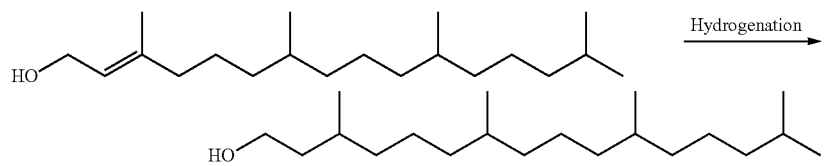

To a solution containing 50 g (169 mmol) of phytol (3,7,11,15-tetramethyl-hexadec-2-en-1-ol, 97% mixture of isomers) and 200 ml ethanol, reaction catalysis Raney nickel (5 g, 50% slurry in water) was added. After stirring the mixture under hydrogen atmosphere (15 psi) for 2 days, the catalyst was removed by vacuum filtration several times through the combination layers of silica and Celite bed on the top. The filtrate was concentrated under reduced pressure to give phytanol (48.8 g, 97.0%) as a colourless oil. $^1$H NMR in CDCl$_3$: δ0.83, 0.85, 0.86, 0.88, 0.91 (5s, each 3H, CH$_3$), 0.94-1.71 (m, 25H, 10CH$_2$+4CH+OH), 3.58-3.78 (m, 2H, CH$_2$OH).

3,7,11,15-Tetramethyl-hexadecyl chloroformate (6a)

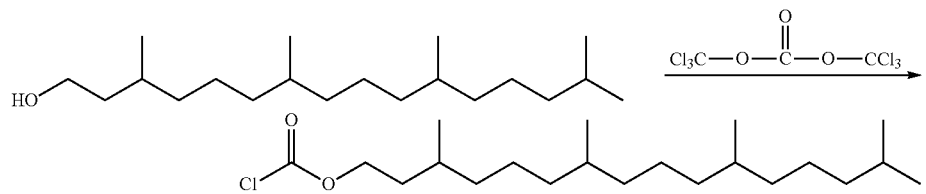

Phytanol (48.8 g, 163.5 mmol), and triphosgene (16.17 g, 54.66 mmol) were dissolve in 300 ml of dichloromethane, stirred and cooled on an ice bath. Anhydrous pyridine (12.93 g, 163.5 mmol) was added dropwise over a period of 1 hour. The reaction mixture was stirred for an additional 1 h at room temperature, and then quickly extracted with extra methylene chloride and ice water. The organic layer was pooled, dried over Na$_2$SO$_4$ and evaporated to dryness to yield 52.22 g (88.7%) of phytanyl chloroformate as yellow liquid. $^1$H NMR in CDCl$_3$: δ0.83, 0.85, 0.86, 0.88, (4s, each 3H, CH$_3$), 0.91 (d, 3H, J=6.0 Hz, CH$_3$), 0.95-1.40 (m, 20H, CH$_2$), 1.39-1.68 (m, 4H, CH), 1.68-1.88 (m, 1H, OH), 4.27-4.47 (m, 2H, CH$_2$OH).

2',3'-Di-O-acetyl-5'-deoxy-5-fluoro-N⁴-(3,7,11,15-Tetramethyl-hexadecyl oxycarbonyl)cytidine (7a)

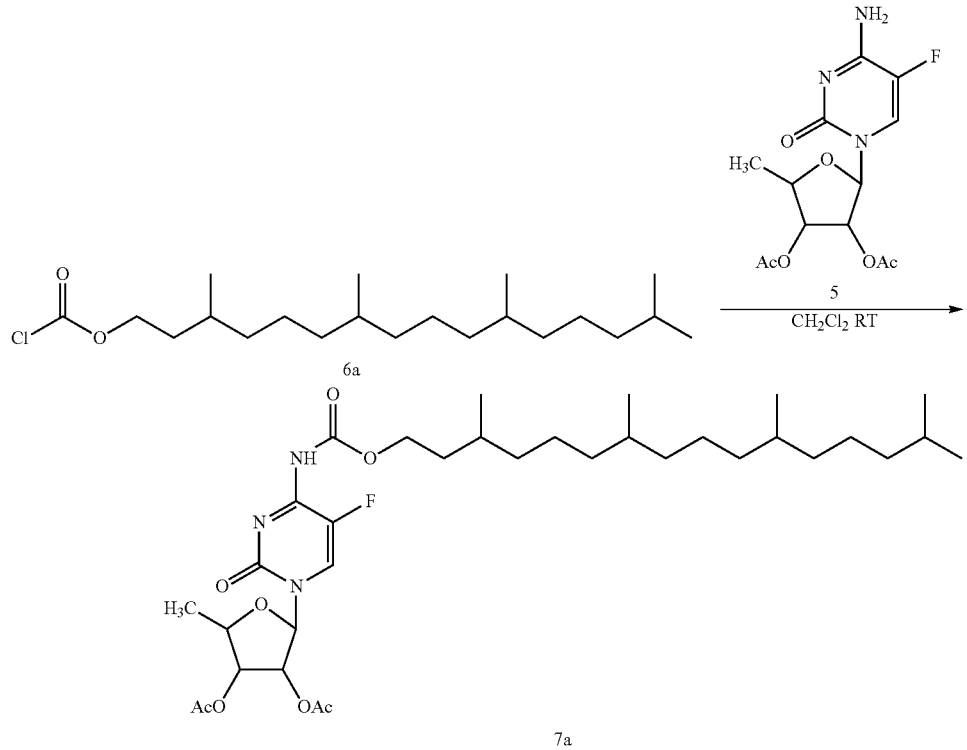

To the ice-cooled solution containing 2',3'-Di-O-acetyl-5'-deoxy-5-fluoroocytidine (5) (9.76 g, 29.64 mmol) in dry $CH_2Cl_2$ (40 ml) and anhydrous pyridine (5 ml), phytanyl chloroformate (12 g, 33 mmol) (6a) was added dropwise in order to keep the low reaction temperature. After stirring the mixture for overnight at room temperature, MeOH (1.3 ml) was added in one portion to stop the reaction. The mixture was evaporated to a syrup mass under reduced pressure. To this residue, diethyl ether (50 ml) was added and the suspension was stirred for 30 min at room temperature. The insoluble precipitate was filtered through a glass filter. The precipitate was washed with 30 ml of diethyl ether. The filtrate and the washings were collected, dried over anhydrous $Na_2SO_4$, and evaporated to dryness. The crude target compound was further purified using silica column chromatography $CH_2Cl_2$:MeOH=5:1 to give 2',3'-Di-O-acetyl-5'-deoxy-5-fluoro-N⁴-(phytanyloxycarbonyl)cytidine (16.7 g, 84.1%) (7a). ¹H NMR in $CDCl_3$: δ0.83, 0.85, 0.86, 0.88 (4s, each 3H, $CH_3$), 0.91 (d, 3H, J=6.6 Hz, $CH_3$), 0.96-1.88 (m, 24H, $CH_2$+CH), 1.47 (d, 3H, J=6.6 Hz, H-5), 2.10, 2.12 (2s, each 3H, OMe), 4.13-4.37 (m, 3H, H-4+$CH_2$OC=ONH), 5.01 (t, 1H, J=5.4 Hz, H-2), 5.29 (t, 1H, J=5.8 Hz, H-3), 5.96 (d, 1H, J=3.8 Hz, H-1), 7.39 (br s, 1H, N—CH=C—F).

5'-deoxy-5-fluoro-N⁴-(3,7,11,15-Tetramethyl-hexadecyloxycarbonyl)cytidine (8a)-5FCPhy

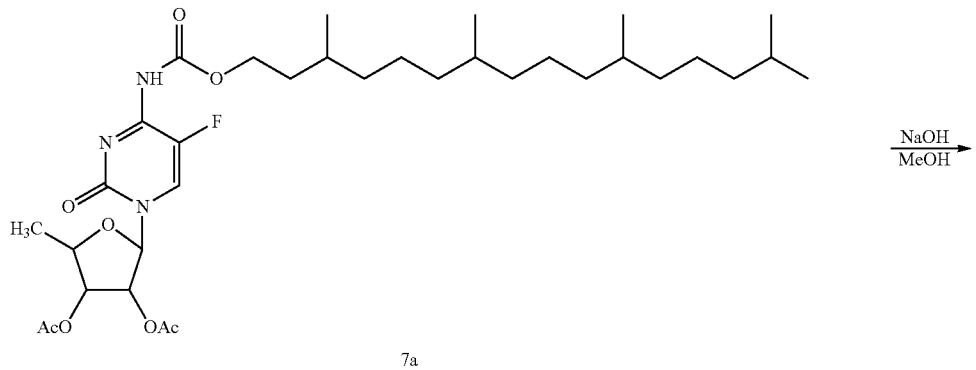

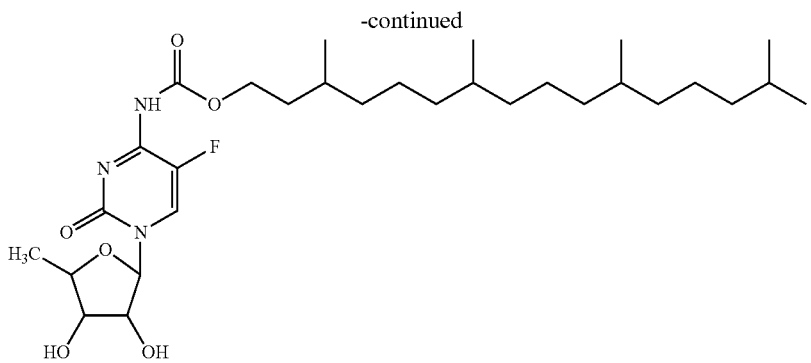

8a

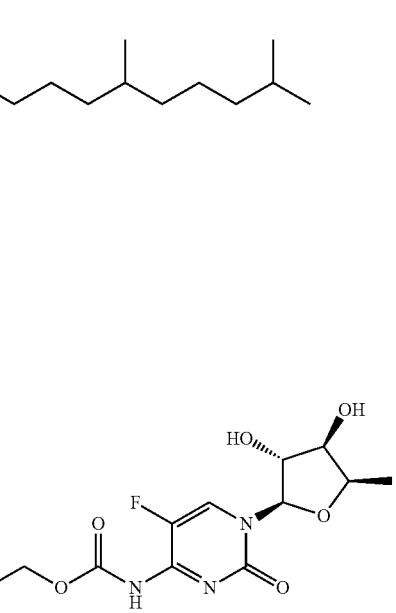

The obtained crude compound 7a (16.70 g, 24.89 mmol) was dissolved in MeOH (50 ml) and cooled down on an ice bath. NaOH (24 ml, 8M) solution was added dropwise to maintain the reaction temperature at 4° C. Then the pH of the reaction mixture was immediately adjusted to 7 by dropwise addition of HCl solution (2.3M). The organic layer was separated and washed with water, dried over anhydrous $Na_2SO_4$ and filtered. The filtrate was evaporated to dryness under reduced pressure. The residue was further purified by silica column chromatography using hexane-ethyl acetate from 60:40 to 0:100 with 10% increment as the eluent. The pure title compound (9.6 g, 67.7% yield) was obtained as a waxy solid with light yellow colour. $^1H$ NMR($CDCl_3$): δ0.83, 0.85, 0.86, 0.88 (4s, 12H, $CH_3$), 0.91 (d, 3H, J=6.1 Hz, $CH_3$), 0.95-1.84 (m, 28H, $CH_2$+CH+OH), 1.40 (d, 3H, J=6.4 Hz, H-5), 3.91 (t, 1H, H-3), 4.15-4.38 (m, 4H, $COOCH_2$+H-2+H-4), 5.69 (d, 1H, J=4.2 Hz, H-1), 7.79 (br s, 1H, N—CH=C—F). MS (APCI): MW: 570.21. $^{13}C$ NMR ($CDCl_3$, 100 MHz): δ [19.64, 19.71, 22.59, 22.68, 24.27, 24.30, 24.45, 24.77, 27.93, 29.68, 32.76, 35.45, 35.54, 37.25, 37.30, 37.38, 37.42, 37.48, 39.33]($CH_3$+$CH_2$+CH+C5), 65.33 ($OCH_2$), [74.94, 75.12 (br), 80.75](C2,C3,C4), 92.00 (br)(C1), 124.3-128.0 (br), 135.0-138.0 (br), 153.11 (NH-COO). Elemental Analysis: calculated: C, 63.24; H, 9.20; N, 7.38; F, 3.30. Found: C, 63.59; H, 9.32; N, 7.11; F, 3.29.

TGA:

5-FC-Phy decomposed in a multi-step process which started at 95° C. and continued to 500° C. The first decomposition with peak at 105° C. attributed to only 0.71% of 75.39% total weight loss up to 500° C. The second degradation step, from 123° C. to 174° C., attributed 5.9%. The major degradation happened between 174° C.-330° C. accounted for over 60% of total weight loss. The degradation continued to 500° C. with two more steps of decomposition. This result revealed that the safe operation temperature for 5-FCPhy is less than 95° C.

DSC:

DSC scans were performed on the neat 5-FCPhy at two heating rates, 10 and 2.5° C./min. Thermal properties of 5-FCPhy observed by DSC included a glass transition near minus 70 deg C. Melting points obtained from visual observation are listed in Table 1.

TABLE 1

| Melting points obtained from visual observation | | |
|---|---|---|
| Temperature scan rate | Visual Point ° C. | Melting |
| 10° C./min | 50-70 | |
| 2.5° C./min | 53-68 | |

Synthesis and Characterisation of 5'-deoxy-5-fluoro-$N^4$-(hexadecyloxycarbonyl)cytidine (8b)-5FCPal

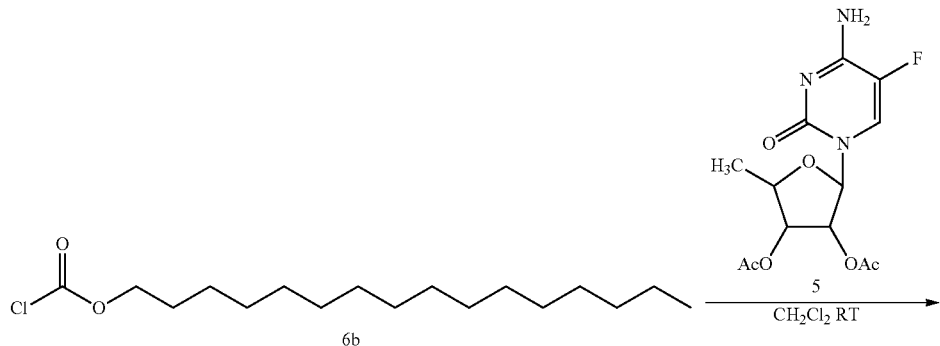

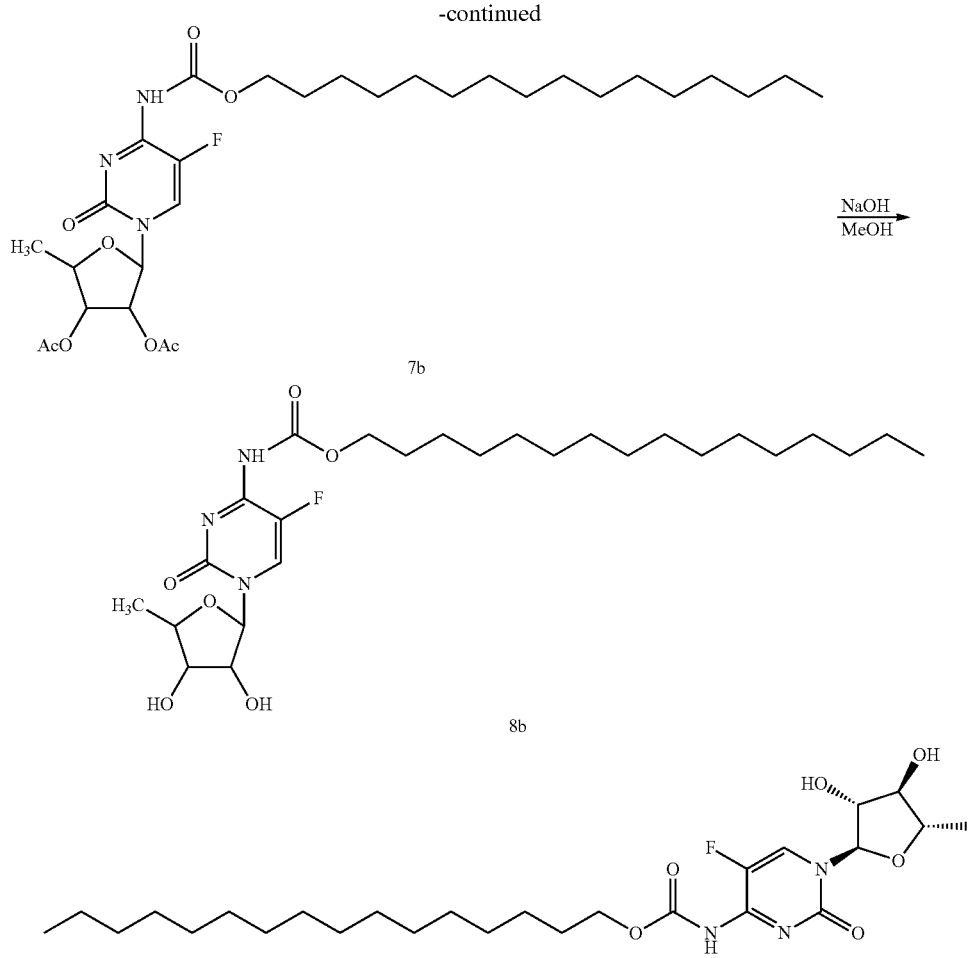

2',3'-Di-O-acetyl-5'-deoxy-5-fluorocytidine (compound 5) was synthesised by the same procedures described in example 1. Cetyl (hexadecyl) chloroformate was purchased from Sigma-Aldrich with 96% purity. Compound 5 (3.97 g, 12.06 mmol) was dissolved in a mixture of dry $CH_2Cl_2$ (20 ml) and anhydrous pyridine (2.5 ml). To the ice-cooled solution, cetyl chloroformate (4.41 g, 14.47 mmol) was added dropwise and stirred overnight at room temperature. After small portion of MeOH (600 μl) was added, the mixture was evaporated to a syrup mass under reduced pressure using rotary evaporator. To this syrup residue, diethyl ether (50 ml) was added and the suspension was stirred for 30 min at room temperature. The insoluble precipitate was filtered through a glass filter. The precipitate was washed further with diethyl ether. The filtrate and the washings were collected, dried over anhydrous $Na_2SO_4$, and evaporated to dryness to give crude compound (7b). MS (APCI): 598.38. The crude compound 7 was dissolved in 50 ml of MeOH and stirred on an ice bath. NaOH solution (20 ml, 8M) was added dropwise to maintain the reaction temperature at 4° C. After immediate neutralization of the reaction mixture with dropwise addition of HCl (2.3M) solution, the organic layer was combined and washed with water, dried over anhydrous $Na_2SO_4$ and filtered. The filtrate was evaporated to dryness under reduced pressure. The pure white crystal compound (8b) (3.5 g, 56.5%) was obtained by crystallization from acetone.

The purity of the final compound was greater than 99% confirmed by UPLC and TLC. The molecular formula is $C_{26}H_{44}FN_3O_6$ and the molecular weight is 513.64. $^1$H NMR ($CDCl_3$, 200 MHz): δ0.88 (t, 3H, J=6.1 Hz, $CH_3$), 1.26 (s, 24H, $CH_2$), 1.39 (d, 3H, J=6.9 Hz, H-5), 1.62 (s, 2H, $CH_2CH_3$), 1.63-1.80 (m, 2H, β$CH_2$), 3.89-4.01 (m, 1H, H-3), 4.11-4.42 (m, 4H, α$CH_2$+H-2+H-4), 5.65 (d, 1H, J=4.1 Hz, H-1). $^{13}$C NMR($CDCl_3$, 400 MHz): δ14.07 ($CH_3$), 18.52 (C5), [22.65, 25.76, 28.55, 29.26, 29.32, 29.51, 29.58, 29.63, 29.67, 31.89]($CH_2$), 66.80 ($OCH_2$), [74.95, 75.12 (br), 80.68] (C2,C3,C4), 92.00 (br)(C1), 124.3-128.0 (br), 135.0-138.0 (br), 153.19 (NHCOO). MS (APCI): 514.15. Elemental analysis: calculated: C, 60.80; H, 8.63; N, 8.18; F, 3.70. Found: C, 60.98; H, 8.74; N, 8.08; F, 3.70.

TGA:

The result for the 5-FCPal revealed that the decomposition process for this prodrug began at approximately 120° C. and continued to occur at higher temperatures. Thermal decomposition took place in three steps. The first step occurred between 120° C. to 180° C. with a mass loss of 7.21%. This loss is accompanied by a colour change of the sample from white crystal to yellow solid. The UPLC analysis of a 130° C. preheated sample showed two hydrophilic degradation peaks in addition to the main compound peak indicating that the first degradation occurred at two positions within the hydrophilic head group and at the drug-lipid linkage. Mass spectroscopy with an APCI probe partially confirmed this result, but no further attempts were made to determine the exact cleavage position and degradation product. The second degradation step occurred between 130° C. and 350° C. resulting in a loss of 65% of the total mass. At the highest temperature examined (500° C.), 81% of the total mass was lost due to degradation. The TGA result suggests that 5-FCPal becomes thermally unstable above 120° C., and thus the temperature should be kept below the above temperature at all times during purification or formulation in order to avoid degradation of the conjugate.

DSC:

DSC scans were performed on the neat 5-FCPal at three heating rates, 10, 2.5 and 0.2° C./min. The characteristic phase transition temperatures and their corresponding enthalpy together with melting points obtained from visual observation are listed in Table 2.

The phase transition temperatures were recorded at the maxima of the endothermic peaks. Enthalpies were obtained by integration of the transition peaks. A single endothermic peak present around 115° C. corresponding to the melting transition that was similar to those observed by visual inspection. Given that this compound starts to undergo degradation at temperatures above 120° C. as indicated in the TGA data, the broad peak that is present after the melting transition can be attributed to the degradation process. To increase resolution and separate thermal effects more clearly, a heating rate of 0.2° C./min was employed. At this heating rate, the melting temperature decreased to 108° C. with a slightly decreased enthalpy. Moreover, the temperature of the first degradation peak also decreased dramatically from over 125° C. to 113° C. Taking peak associated enthalpy information into consideration, it is clear that the shift in melting point and degradation temperature to lower temperatures is derived from the differences in the heating rate. In general, with decreased heating rate in DSC measurement, the resolution is increased, the minor effects, such as glass transition, are minimized or even hidden, thus the thermal behaviour, for example melting point, become much sharper and are able to be separated from merged peaks. Furthermore, at slower heating rate, the sample starts to absorb heat to induce the thermal behaviour at relatively lower temperatures in the slow heating process, a shift towards lower temperature of peak maxima compared to faster heating rates is usually seen. This trend can be seen in Table 2.

TABLE 2

Thermal properties of 5-FCPal determined by DSC.

| DSC scan rate | Pre transition $T_{max}$ ° C. [transition enthalpy KJ mol$^{-1}$] | Pre transition $T_{max}$ ° C. [transition enthalpy KJ mol$^{-1}$] | Pre transition $T_{max}$ ° C. [transition enthalpy KJ mol$^{-1}$] | Visual Melting Point ° C. | Melting Point TM ° C. [transition enthalpy KJ mol$^{-1}$] |
|---|---|---|---|---|---|
| 10° C./min | — | 48.16 [−0.68] | 93.49 [−1.70] | 113-119 | 118.32 [−32.86] |
| 2.5° C./min | — | 47.32 [−1.58] | 92.40 [−1.18] | 110-119 | 114.94 [−32.29] |
| 0.2° C./min | 19.88 [−1.19] | 46.27 [−0.91] | 90.54 [−0.73] | — | 108.35 [−29.34] |

Synthesis and Characterisation of 5'-deoxy-5-fluoro-N$^4$-(cis-9-Octadecenyl oxycarbonyl)cytidine-5-FCole

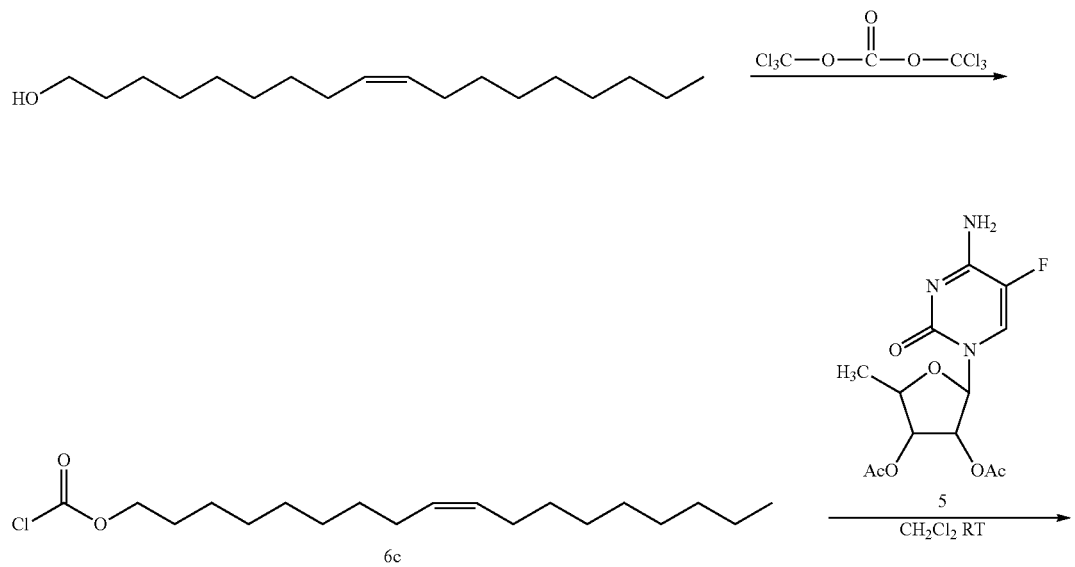

-continued

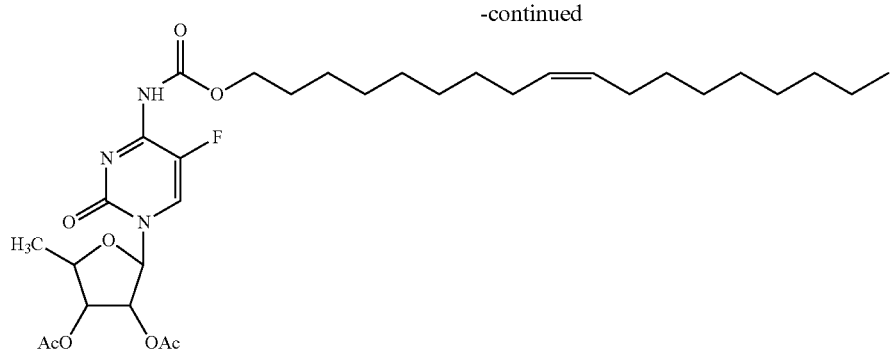

7c

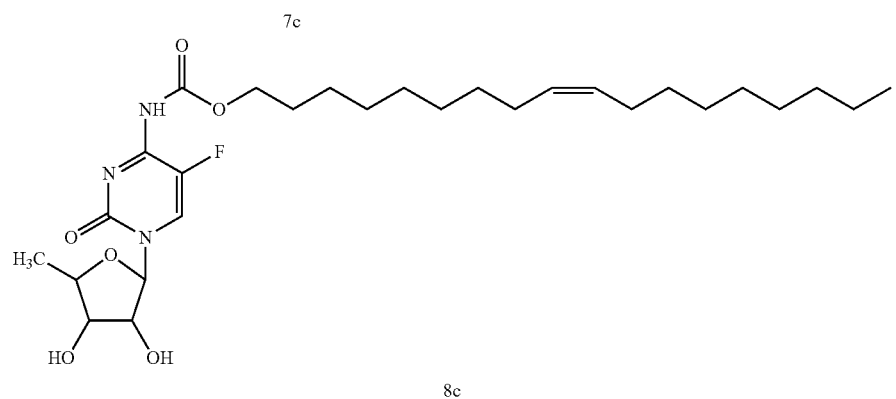

8c cis-9-Octadecenyl chloroformate (6c)

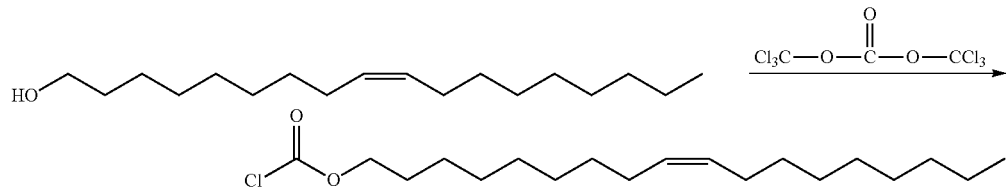

Oleyl alcohol (17.58 g, 65.40 mmol), and triphosgene (6.47 g, 21.80 mmol) were dissolved in 180 ml dichloromethane, stirred and cooled on an ice bath. Anhydrous pyridine (5.17 g of, 65.40 mmol) was added dropwise into the pre-cooled solution. The reaction mixture was stirred for an additional 2 h at room temperature, and then quickly extracted with ice water. The organic layer was combined, dried over $Na_2SO_4$ and evaporated to giving crude 18.25 g (84.3% yield) of oleyl chloroformate as liquid. $^1$H NMR in $CDCl_3$: δ0.88 (t, 3H, J=6.3 Hz, $CH_3$), 1.29 (d, 22H, J=7.7 Hz, $CH_2$), 1.73 (t, 2H, J=6.6 Hz, β$CH_2$), 2.02 (d, 4H, J=5.4 Hz, —$CH_2$—CH=CH—$CH_2$—), 4.31 (t, 2H, J=6.6 Hz, α$CH_2$), 5.35 (m, 2H, —CH=CH—).

5'-deoxy-5-fluoro-$N^4$-(cis-9-Octadecenyl-1-oxycarbonyl)cytidine (8c)-5FCOle

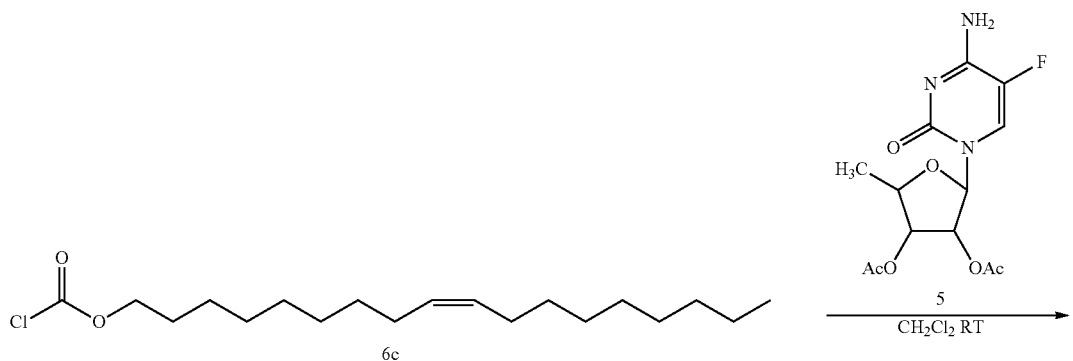

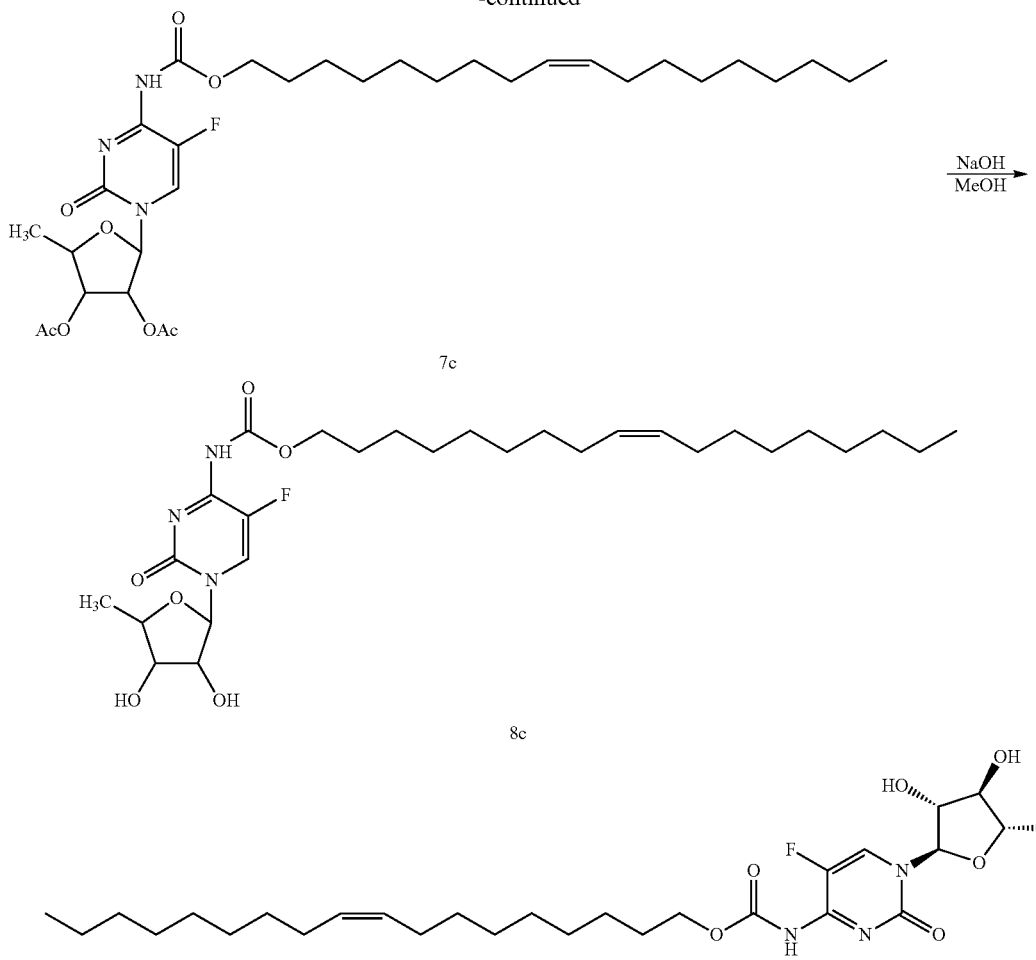

2',3'-Di-O-acetyl-5'-deoxy-5-fluorocytidine (compound 5) was synthesized following the procedures described previously. Compound 5 (3.53 g, 10.72 mmol) was dissolved in a mixture of dry $CH_2Cl_2$ (20 ml) and anhydrous pyridine (2.3 ml). To the ice-cooled solution, oleyl chloroformate (4.26 g, 12.86 mmol) was added dropwise and stirred overnight at room temperature. After small portion of MeOH (500 μl) was added, the mixture was evaporated to a syrup mass under reduced pressure using rotary evaporator. To this residue, diethyl ether (60 ml) was added and the suspension was stirred for 30 min at room temperature. The insoluble precipitate was filtered through a filter paper. The precipitate was washed further with diethyl ether. The filtrate and the washings were collected, dried over anhydrous $Na_2SO_4$, and evaporated to dryness to give crude compound (7c). MS (APCI): 624.00. This crude sample was dissolved in 50 ml of MeOH and stirred on an ice bath. NaOH solution (20 ml, 8M) was added dropwise to ensure the low temperature reaction condition maintained. After immediate neutralization of the reaction mixture with dropwise addition of HCl solution (2.3 M), the mixture was then partitioned between $CH_2Cl_2$ and water. The organic layer was combined and washed with water, dried over anhydrous $Na_2SO_4$ and filtered. The filtrate was evaporated to dryness under reduced pressure. The pure compound (8c) was obtained by flash column chromatography purification using $CHCl_2$ and MeOH eluent, starting from 100% $CH_2Cl_2$ and gradually increased the concentration to 10%. MeOH. The title compound was obtained as a yellow solid (3.46 g, 59.8% yield). $^1$H NMR($CDCl_3$): δ0.88 (t, 3H, J=6.0 Hz, $CH_3$), 1.28 (d, 22H, J=4.0 Hz, $CH_2$), 1.42 (d, 3H, J=6.5 Hz, H-5), 1.58-1.77 (m, 2H, β$CH_2$), 2.01 (d, 4H, J=5.1 Hz, —$CH_2$—CH═CH—$CH_2$—), 3.73 (br s, 1H, H-3), 3.87 (t, 1H, J=4.7 Hz, H-4), 4.18 (t, 2H, J=6.4 Hz, α$CH_2$), 4.27 (d, 1H, J=4.5 Hz, H-2), 5.35 (t, 2H, J=5.7 Hz, —CH═CH—), 5.71 (d, 1H, J=2.9 Hz, H-1), 7.79 (br s, 1H, N—CH═C—F). $^{13}$C NMR($CDCl_3$, 100 MHz): δ14.07 ($CH_3$), 18.54 (C5), [22.64, 25.76, 27.16, 27.18, 28.54, 29.21, 29.28, 29.41, 29.48, 29.72, 31.86]($CH_2$), 66.85 ($OCH_2$), [74.94, 75.12 (br), 80.70](C2,C3,C4), 92.00 (br)(C1), [129.71, 129.95](CH), 124.3-128.0 (br), 135.0-138.0 (br), 153.15 (NHCOO). MS (APCI): 540.28.

TGA:

The TGA results for the prodrug amphiphile 5-FCOle showed a three step thermal degradation process. The first step accounted for 80.3% total mass loss of the original sample up to 500° C. The degradation starting at 123° C. indicates that the temperature should be well below such temperature to retain the intact structure of 5-FCOle. A successive mass loss occurred between 123° C. to 400° C., accounting for over 70% of weight loss. A further 7% weight loss happened when temperature reached 500° C.

DSC:

DSC scans were performed on the neat 5-FCOle at three different heating rates, 10, 2.5 and 0.2° C./min. The characteristic phase transition temperatures and their corresponding enthalpies together with melting points obtained from visual observation are listed in Table 3.

TABLE 3

| | Thermal properties of 5-FCOle determined by DSC. | | | | | |
|---|---|---|---|---|---|---|
| DSC scan rate | Pre transition $T_{max}$ °C. [transition enthalpy KJ mol$^{-1}$] | Pre transition $T_{max}$ °C. [transition enthalpy KJ mol$^{-1}$] | Pre transition $T_{max}$ °C. [transition enthalpy KJ mol$^{-1}$] | Glass Transition Tg Onset °C. [Midpoint °C.] | Visual Melting Point °C. | Melting point $T_{max}$ °C. [transition enthalpy KJ mol$^{-1}$] |
| 10° C./min | −15.67 [−0.91] | −5.83 [−0.72] | — | — | 66-75 | 72.00 [−12.00] |
| 2.5° C./min | −15.84 [−0.53] | −6.71 [−0.73] | 36.37 [−0.08] | — | 65-73 | 71.41 [−12.10] |
| 0.2° C./min | −15.42 [−2.17] | −6.55 [−1.71] | — | — | 63-77 | 74.62 [−12.78] |

Synthesis and Characterisation of 5'-deoxy-5-fluoro-N$^4$-(Octadecyl-1-oxycarbonyl)cytidine-5-FCste

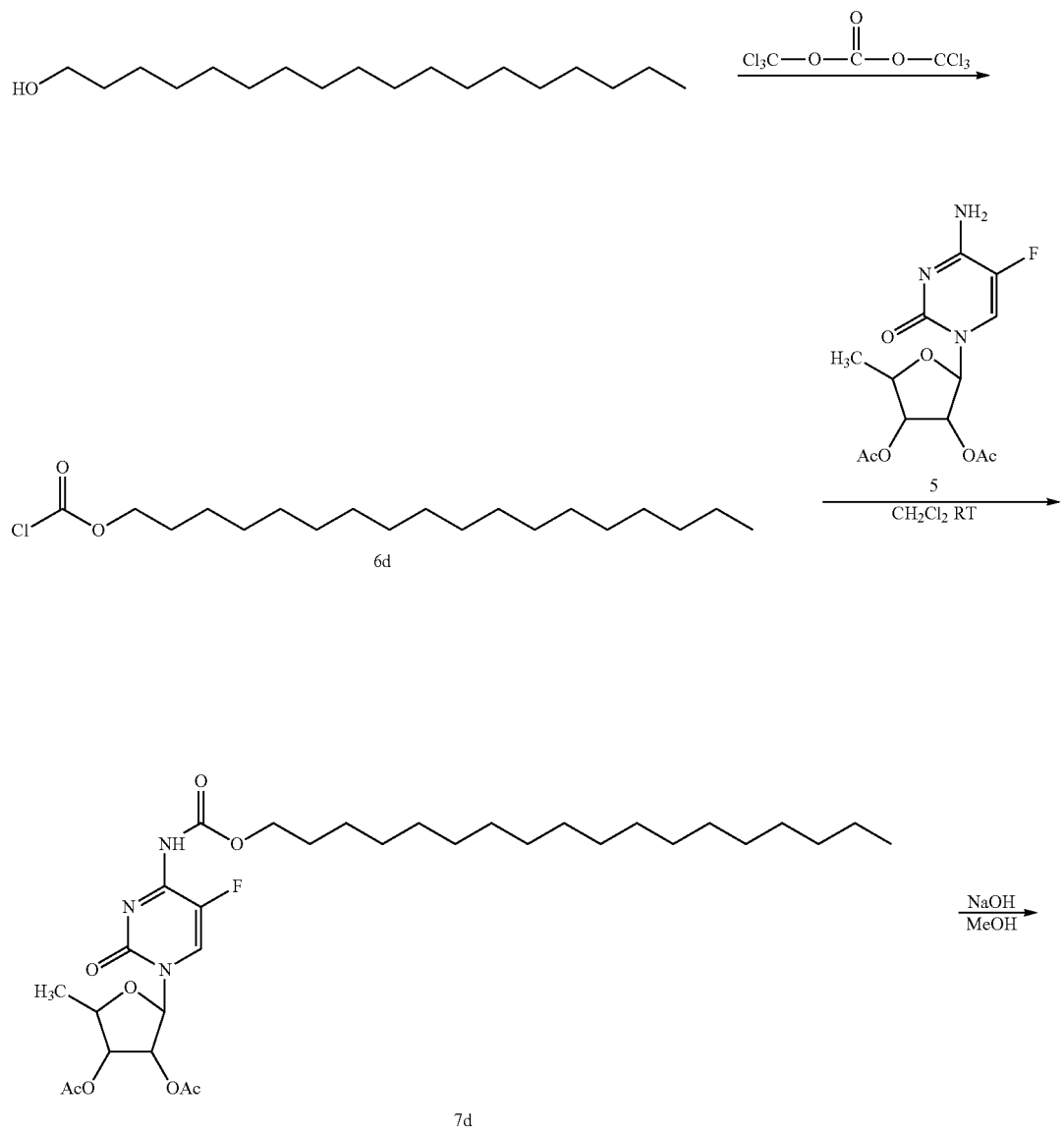

-continued

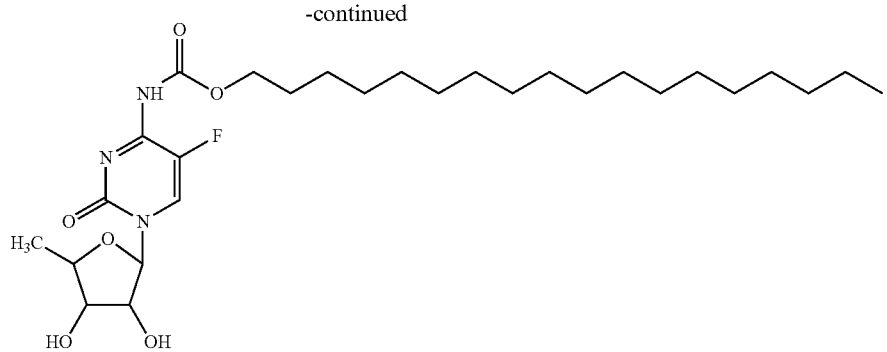

8d

Octadecyl Chloroformate (6d)

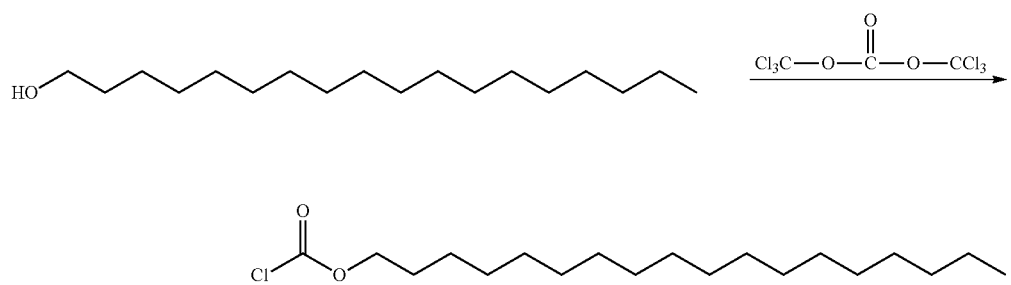

Stearyl alcohol (2.7 g, 0.01 mol), and triphosgene (0.99 g, 0.0067 mol) were dissolved in 20 ml methylene chloride, stirred and cooled to 10-15° C. Anhydrous pyridine (0.8 g of, 0.02 mol) was added dropwise into the pre-cooled solution over a 1 hr period. The reaction mixture was stirred for an additional 1 h, then heated in a water bath at 65° C. for 15 min until all the methylene chloride evaporated. The residue was washed 3 times with cold water, dried over $Na_2SO_4$ and evaporated to give stearyl chloroformate (1.88 g, 83% yield), also known as octadecyl chloroformate.

$^1$H NMR ($CDCl_3$): δ0.88 (t, 3H, J=6.4 Hz, $CH_3$), 1.26 (m, 30 $CH_2$), 1.62 (m, 2H, α-$CH_2$), 4.31 (t, 2H, J=6.7 Hz, β-CH2)

5'-deoxy-5-fluoro-$N^4$-(Octadecyl-1-oxycarbonyl)
cytidine (8d)-5FCste

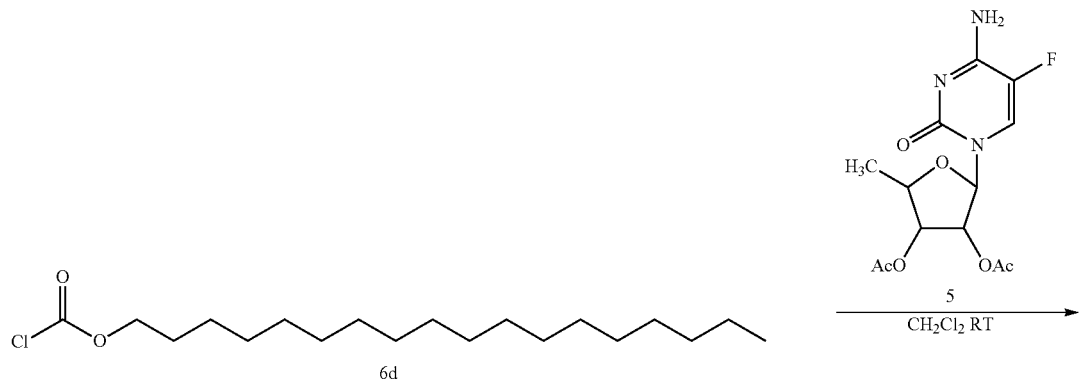

6d

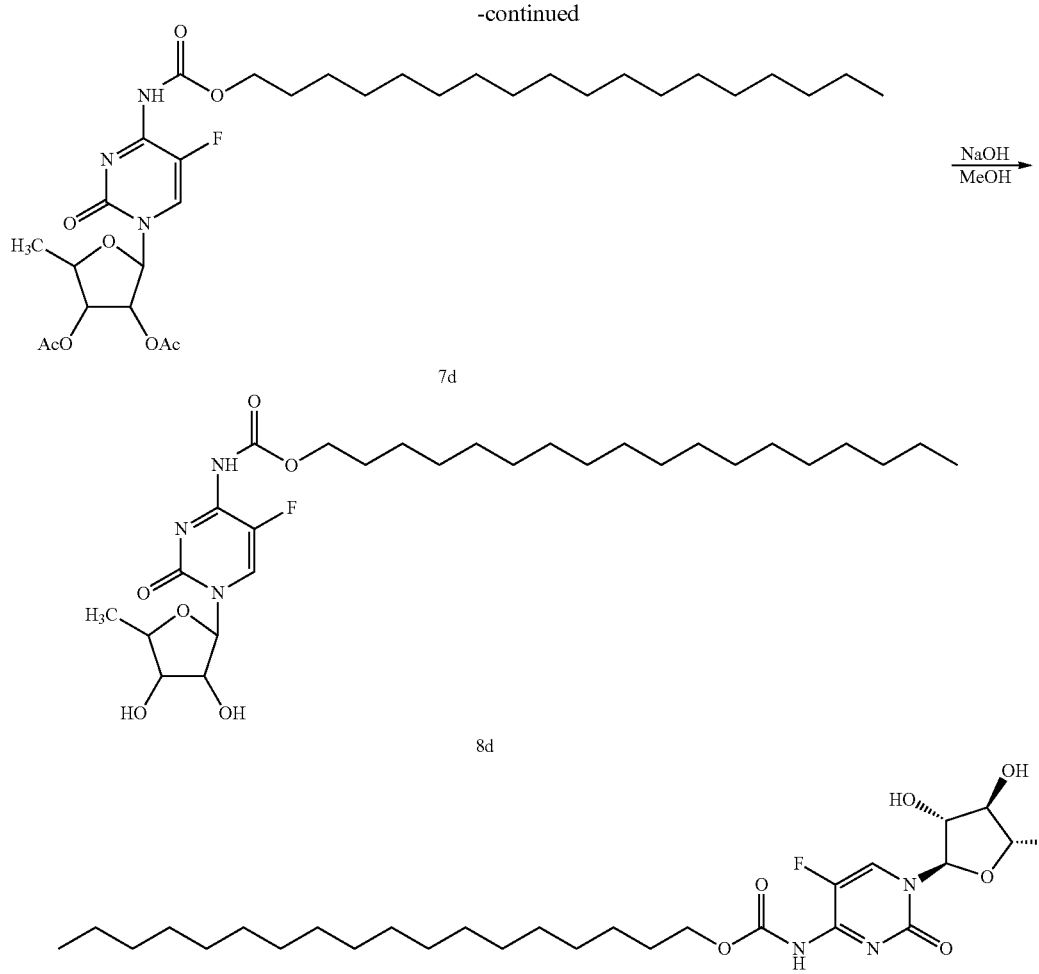

2',3'-Di-O-acetyl-5'-deoxy-5-fluorocytidine (compound 5) was synthesized following the procedures described previously. Compound 5 (1.5 g, 0.0046 mol) was dissolved in a mixture of dry $CH_2Cl_2$ (20 ml) and anhydrous pyridine (1 ml) over an ice bath. To the ice-cooled solution, compound 6d (1.82 g, 0.0055 mol, 1.2 equiv.) was added dropwise and stirred overnight at room temperature. After a small portion of MeOH (250 µl) was added, the mixture was evaporated to dryness. To this residue, diethyl ether (50 ml) was added and the suspension was stirred for 60 min at room temperature. The insoluble precipitate was filtered through a filter paper. The precipitate was washed further with diethyl ether. The filtrate and the washings were collected, dried over anhydrous $Na_2SO_4$, and evaporated to dryness to give crude compound (7d). This crude sample was dissolved in 20 ml of MeOH and stirred on an ice bath. NaOH solution (10 ml, 8M) was added dropwise to ensure the low temperature reaction condition maintained. After immediate neutralization of the reaction mixture with dropwise addition of HCl solution (4 M), the mixture was then partitioned between $CH_2Cl_2$ and water. The organic layer was combined and washed with water, dried over anhydrous $Na_2SO_4$ and filtered. The filtrate was evaporated to dryness under reduced pressure. The pure compound (8d) was obtained by flash column chromatography purification using $CHCl_2$ and MeOH eluent, starting from 100% $CH_2Cl_2$ and gradually increasing the concentration to 10% MeOH. The title compound 8d was obtained as a white solid (1.97 g, 78% yield).

$^1$H NMR($CDCl_3$): δ0.9 (t, 3H, J=6.4 Hz, —$CH_3$), 1.25 (m, 28H, $CH_2$), 1.39 (d, 3H, J=6.6 Hz, ribose-$CH_3$ (H-5)), 1.7 (t, 2H, J=7 Hz. β$CH_2$), 3.9 (dd, 1H, J=3.7, 5.1, H-4), 4.17-4.27 (m, 1H, H-2), 4.20 (s, 2H, α$CH2$), 4.29-4.40 (m, 1H, H-3), 5.64 (d, 1H, J=4 Hz, H-1), 7.8 (b.s., 1H, N—CH=C—F).

$^{13}$C NMR ($CDCl_3$): δ14.1 ($CH_3$), 15.9 (ribose-$CH_3$) [22.7, 25.8, 29.2, 29.3, 29.5, 29.6, 29.7, 29.7, 31.9] $CH_2$, 67.0 $OCH_2$) [76.4, 77.0, 77.6] (C2, C3, C4), 95.0br (C1), 120.3 (CF), 153.4 (NHCOO) 157-160br (Aromatic C)

DSC:

DSC scans were performed on the neat 5-FCste at 2.5° C./min. The characteristic phase transition temperatures and their corresponding enthalpies together with melting points obtained from visual observation are listed in Table 4.

TABLE 4

Thermal properties of 5-FCste determined by DSC.

| DSC scan rate | Peak T ° C. [transition enthalpy KJ mol$^{-1}$] | Peak T ° C. [transition enthalpy KJ mol$^{-1}$] | Peak T ° C. [transition enthalpy KJ mol$^{-1}$] | Peak T ° C. [transition enthalpy KJ mol$^{-1}$] |
|---|---|---|---|---|
| 12.5° C./min | 8.59 [38.84] | 15.29 3.26] | [−117.37 75.49] | [−135.08 [−6.41] |

Synthesis and Characterisation of 5'-deoxy-5-fluoro-N⁴-(cis-9,12-Octadecenyl oxycarbonyl)cytidine-5-FCleo
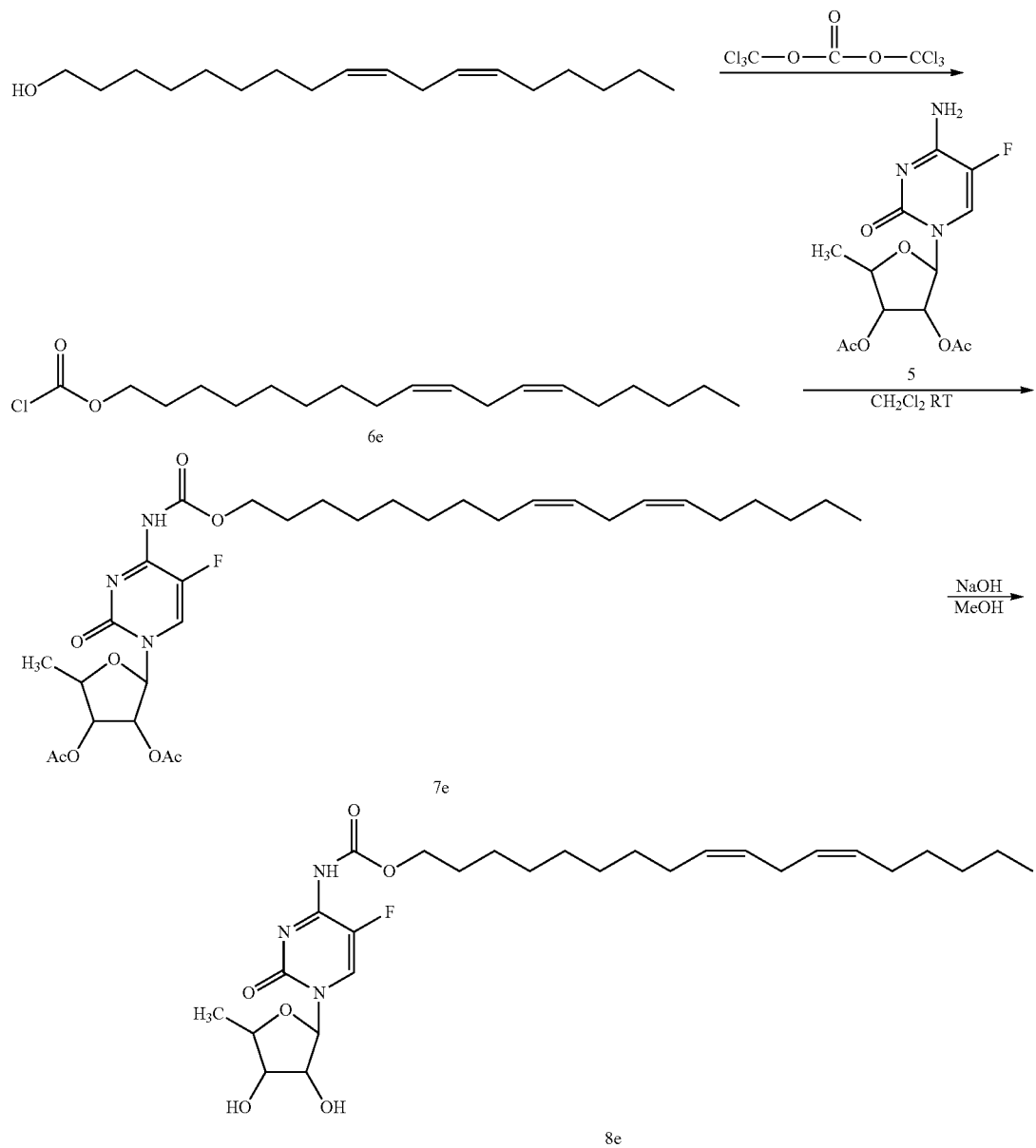
cis-9,12-Octadecenyl chloroformate (6e)
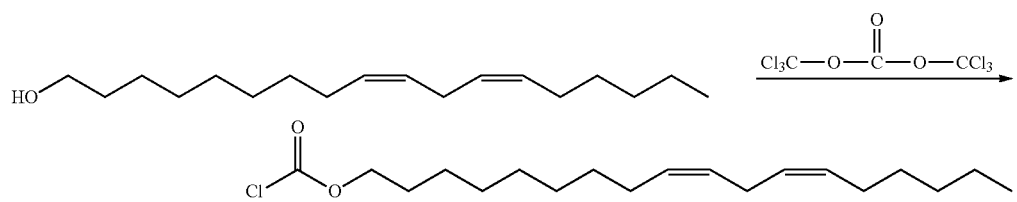

First, linoleic acid was converted to linoleoyl. 4.5 mmol LiAlH4 (0.17 g—1.25 equivalent of acid to reduce) was suspended in 20 ml dry diethyl ether. 1 g (3.57 mmol) of linoleic acid was added dropwise in 10 ml diethyl ether, and it was ensured that the addition created a gentle reflux. The reaction vessel was protected from light to prevent degradation. The reaction was continually stirred for 3 hours and left overnight to ensure completion as determined by TLC. The flask was placed in an ice water bath and 4 ml of 10% sulphuric acid was added with care. The organic layer was decanted, and aqueous suspension washed with ether (20 ml×3). The ether fractions were combined and washed with water twice and dried over Na$_2$SO$_4$, filtered and evaporated to obtain a white-yellowish wax, linoleoyl (85% yield).

Then, linoleoyl (20 g, 0.0075 mol), and triphosgene (1.3 g, 0.0044 mol) were dissolved in 20 ml methylene chloride, stirred and cooled to 10-15° C. Anhydrous pyridine (0.8 g of, 0.013 mol) was added dropwise into the pre-cooled solution over a 1 hr period. The reaction mixture was stirred for an additional 1 h, then heated in a water bath at 65° C. for 15 min until all the methylene chloride evaporated. The residue was washed 3 times with cold water, dried over Na$_2$SO$_4$ and evaporated to give linoleoyl chloroformate (2.14 g, 87% yield), also known as cis-9,12-Octadecenyl chloroformate.

$^1$H NMR(CDCl$_3$): δ0.88 (t, 3H, J=6.2 Hz, CH$_3$), 1.20-1.4 (m, 14H, CH$_2$), 1.63-1.73 (m, 2H, βCH$_2$), 2.01 (d, 4H, J=5.1 Hz, —CH$_2$—CH=), 2.77 (t, 2H, J=5.52 Hz, =CHCH$_2$CH=), 4.35 (t, 2H, J=6.4 Hz, αCH$_2$), 5.37 (m, 4H, —CH=CH—), 5.41 (m, 4H, =CH).

5'-deoxy-5-fluoro-N$^4$-(cis-9,12-Octadecenyl-1-oxycarbonyl)cytidine (8e)-5FCleo

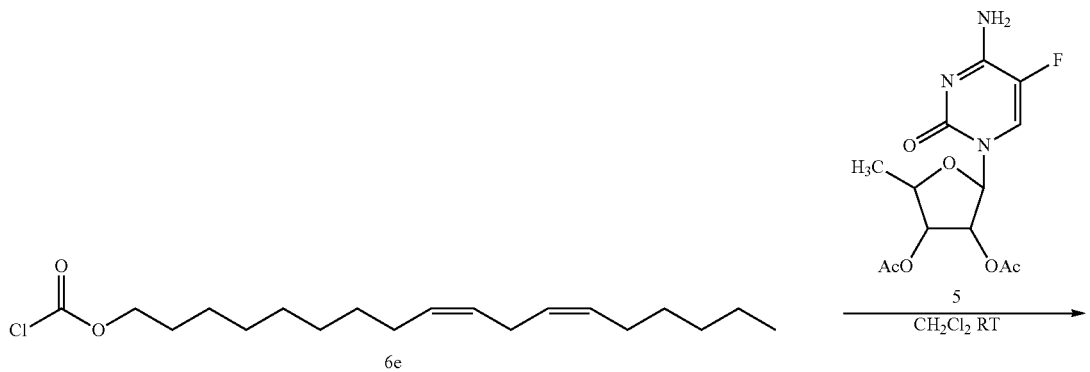

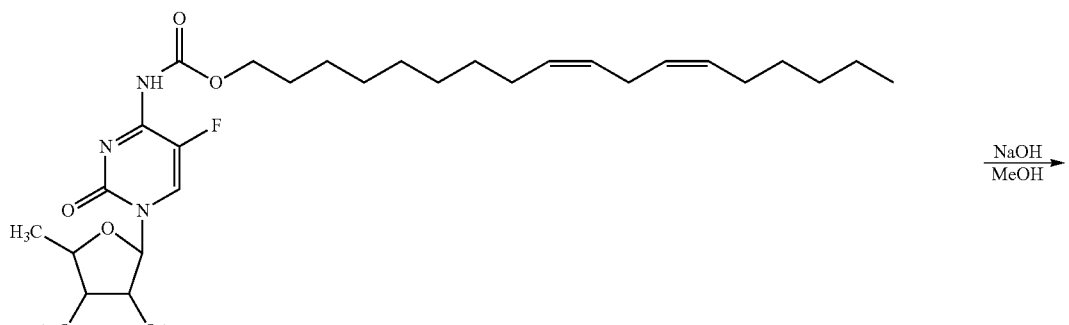

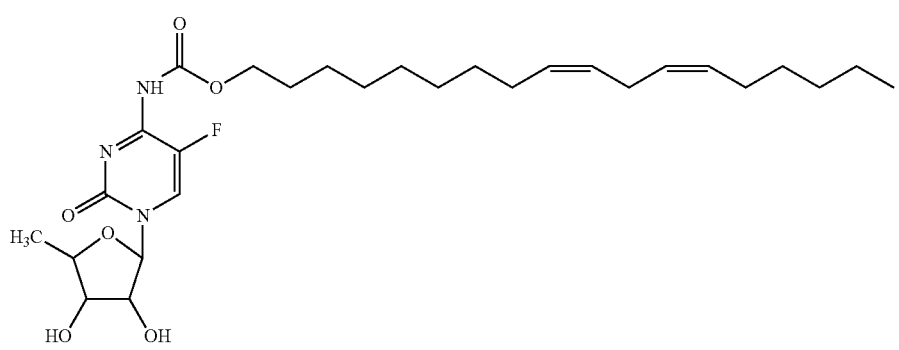

-continued

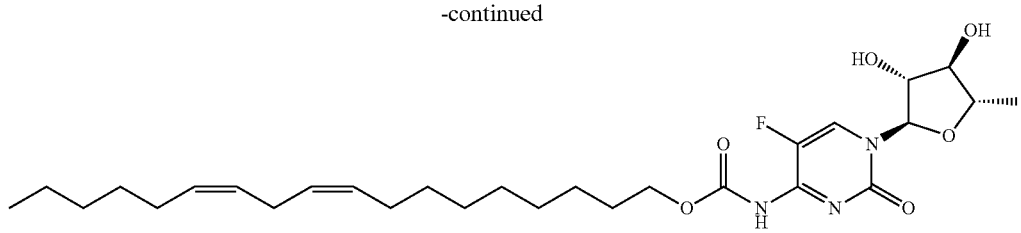

2',3'-Di-O-acetyl-5'-deoxy-5-fluorocytidine (compound 5) was synthesized following the procedures described previously. Compound 5 (2.43 g, 0.0074 mol) was dissolved in a mixture of dry CH$_2$Cl$_2$ (20 ml) and anhydrous pyridine (1 ml) over an ice bath. To the ice-cooled solution, compound 6e (2.43 g, 0.0074 mol, 1 equiv.) was added dropwise and stirred overnight at room temperature. Due to the light sensitive nature of the unsaturated chloroformate the reaction was kept insulated from ambient light. After a small portion of MeOH (250 µl) was added, the mixture was evaporated to dryness. To this residue, diethyl ether (100 ml) was added and the suspension was stirred for 10 min at room temperature. The insoluble precipitate was filtered through a filter paper. The precipitate was washed further with diethyl ether. The filtrate and the washings were collected, dried over anhydrous Na$_2$SO$_4$, and evaporated to dryness to give crude compound (7e). This crude sample was dissolved in 20 ml of MeOH and stirred on an ice bath. NaOH solution (10 ml, 8M) was added dropwise to ensure the low temperature reaction condition maintained. After immediate neutralization of the reaction mixture with dropwise addition of HCl solution (4 M), the mixture was then partitioned between CH$_2$Cl$_2$ and water. The organic layer was combined and washed with water, dried over anhydrous Na$_2$SO$_4$ and filtered. The filtrate was evaporated to dryness under reduced pressure. The pure compound (8e) was obtained by flash column chromatography purification using CHCl$_2$ and MeOH eluent, starting from 100% CH$_2$Cl$_2$ and gradually increasing the concentration to 10% MeOH. The title compound 8e was obtained as a yellowish wax (3.1 g, 75% yield).

$^1$H NMR(CDCl$_3$): δ0.88 (t, 3H, J=6.2 Hz, CH$_3$), 1.20-1.4 (m, 14H, CH$_2$), 1.39 (d, 3H, J=6.4 Hz, H-5), 1.63-1.73 (m, 2H, βCH$_2$), 2.01 (d, 4H, J=5.1 Hz, —CH$_2$—CH=), 2.77 (t, 2H, J=5.52 Hz, =CHCH$_2$CH=), 3.9 (dd, 1H, J=3.8 Hz, 5.3 Hz, H-3), 4.20 (s, 1H, H-2), 4.17-4.24 (t, 2H, α-CH$_2$), 4.33-4.38 (m, 1H, H-3), 5.34 (m, 4H, =CH), 5.63 (d, 1H, J=4 Hz, H-1) (t, 1H, J=4.7 Hz, H-4), 4.18 (t, 2H, J=6.4 Hz, αCH$_2$), 4.27 (d, 1H, J=4.5 Hz, H-2), 5.37 (m, 4H, —CH=CH—), 5.71 (d, 1H, J=2.9 Hz, H-1), 7.8 (br s, 1H, N—CH=C—F).

DSC:

DSC scans were performed on the neat 5-FCleo at 2.5° C./min. The characteristic phase transition temperatures and their corresponding enthalpies together with melting points obtained from visual observation are listed in Table 5.

TABLE 5

Thermal properties of 5-FCleo determined by DSC.

| DSC scan rate | Peak T ° C. [transition enthalpy KJ mol$^{-1}$] | Peak T ° C. [transition enthalpy KJ mol$^{-1}$] | Peak T ° C. [transition enthalpy KJ mol$^{-1}$] |
| --- | --- | --- | --- |
| 2.5° C./min | −35.24 [0.60] | 97.33 [2.41] | 146.01 [0.13] |

Synthesis and Characterisation of Hexahydrofarnesoyl Dopamine

Hexahydrofarnesol 3,7,11-Trimethyl-dodecan-1-ol (hexahydrofarnesol) was made in-house in the same manner as previously published (D. Wells, C. Fong, I. Krodkiewska, C. J. Drummond, *J. Phys. Chem. B.*, 110, 5112-5119, 2006).

H-Farnesoic Acid

Hexahydrofarnesol (12 g, 53 mmol) was diluted with 150 ml of glacial acetic acid and cooled in an ice bath. Chromium trioxide (13.13 g 131.34 mmol) was dissolved in 15 ml of water and added over 2 hours to the reaction mixture and was left overnight allowing the reaction mixture to return to room temperature. An aliquot was taken out, quenched with water and a few crystals of sodium metabisulphite, followed by extraction with petroleum spirit 40/60. The sample was analysed by NMR. If the alcohol was converted completely, the whole mixture was extracted twice with petroleum spirit 40/60. The extract was then washed with brine and a small addition of sodium metabisulphite. A greenish extract was filtered through a 1 cm pad of silica. The filtrate was evaporated to dryness under reduced pressure. The crude acid was subsequently vacuum distilled using Buchi Kugelrohr. The main fraction, collected at 145° C./1.6×10$^2$ mm Hg was a colourless oil confirmed by $^1$HNMR.

Hexahydrofarnesoyl Chloride

Hexahydrofarnesoic acid (7.785 g, 32.11 mmol) was diluted with 35 ml of dry DCM, a catalytic amount of dry DMF was added to the mixture and the solution cooled to ~0° C. The reaction flask was kept under Argon atmosphere. Oxalyl chloride 4.89 g (38.54 mmols, 1.2 eq.), dissolved in 20 ml of dry DCM, was added dropwise and the cooling bath was removed. The reaction mixture remained colourless when cold, then became strongly coloured at RT. NMR confirmed the complete conversion of the acid to its chloride. The solvent was removed under vacuum to yield 7.947 g of orange-brown oil (94% yield). The crude acid chloride was obtained by vacuum distillation; the main fraction was collected at 125° C./7.9×10$^{-3}$ mm Hg. Yield calculated for the pure product was 84.9%.

Hexahydrofarnesoyl Dopamine

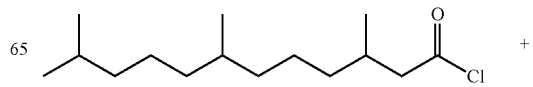

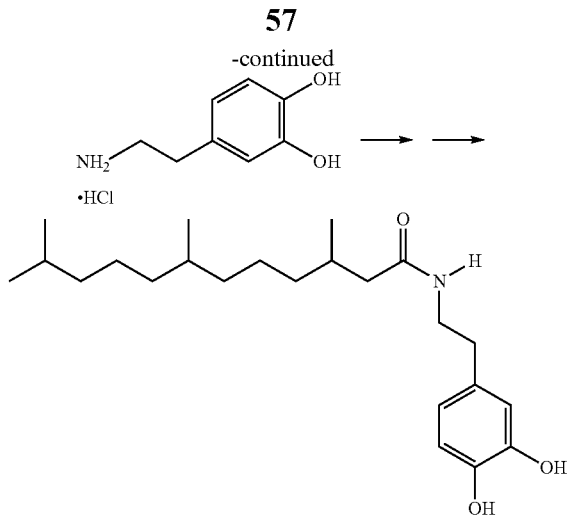

Dopamine hydrochloride (10.07 g, 53.135 mmol) was dissolved in 60 ml of dry DMF and maintained under Argon atmosphere. It formed colourless solution. Dry triethylamine (8.06 g, 79.70 mmol) was added and cooled to −20° C. Hexahydrofarnesoyl chloride (6.93 g, 26.57 mmol) was diluted with 50 ml of dry DCM and added dropwise to the reaction mixture over 2 hours, while maintaining the temperature under −20° C. The RM was heterogenous during the acid chloride addition. After 30 min, the RM was allowed to return slowly to RT and stirred for a further 2 hours. NMR of an aliquot showed no unreacted acid chloride. 100 ml of DCM and 75 ml of brine was added and the mixture was acidified with diluted hydrochloric acid to pH 3. The separated aqueous layer was back-washed with DCM and the combined DCM phase was washed twice with 75 ml of brine. DCM extract, still containing DMF was concentrated under vacuum, resulting in a brown heavy oil, 10.5 g.

This material was preadsorbed on 20 g of silica and chromatographed using chloroform as eluent.

That first purification gave the product of ~95% purity. The product was redissolved in ethanol and purified on prepHPLC using a Gemini-NX 10 micrometer $C_{18}$ 250×50 mm Phenomenex column to obtain product with purity more than 99%.

MS(APCI, positive ion): 378.17, $^1$HNMR: 6.66, d, J 8.0 Hz, 1H, Ar—H5; 6.64, d, J 2.0 Hz, 1H, Ar—H2; 6.52, dd, J 8.0, 2.0 Hz, 1H, Ar—H6; 3.33, t, J 7.2 Hz, 2H, $NCH_2$; 2.62, t, J 7.2 Hz, 2H, $CH_2Ar$; 2.15-2.09, m, 1H, $C(O)CH_2$; 1.95-1.89, m, 1H, $C(O)CH_2$; 1.59-1.45, m, 1H, $CHMe_2$; 1.44-1.01, m, 14H, 6×$CH_2$, 2×CH; 0.90-0.84, m, 12H, 4×$CH_3$.

Example 2

Demonstration of Self-Assembly Behaviour

Cross-Polarised Light Microscopy (Water Penetration Scans):

Lyotropic mesophase behaviour was studied using water penetration experiments. Neat amphiphile was placed on a glass slide, melted and cooled to facilitate sample homogenization and then covered with a glass cover slip. A few drops of Milli-Q water were then introduced to the edge of the cover slip which was drawn in by capillary action resulting in a concentration gradient from pure amphiphile in the centre to pure water around the edges of the cover slip. The generated mesophases were identified by their characteristic birefringent textures. Samples were then heated at 2° C./min from room temperature to ~99° C. using an FP90 Linkam hotstage (Linkam Scientific Instruments, England). Thermotropic phase behaviour was also examined in the similar method but in the absence of water. The phases were viewed using an Olympus GX51 inverted polarising microscope (Olympus Australia Pty. Ltd, Australia) equipped with an Olympus C-5060 digital camera for image capture. All images were taken with 100× magnification unless elsewhere stated. Visual melting point was also determined on the same system with a heating rate of 10° C./min and 2.5° C./min.

Small Angle X-Ray Scattering (SAXS):

The bulk phase of the binary amphiphile/water system was prepared by weighing the appropriate amount of sample and water in a sample vial. For those samples requiring pre-treatment, the samples were quickly melted in a pre-heated temperature controlled silicon-oil heating bath prior to addition of water. Homogenization of the amphiphile/water system was achieved through vigorous agitation using a mechanical vortex with subsequent standing at room temperature for a minimum of 7 days to equilibrate before taking measurements. The prepared samples were analysed using an Anton-Paar SAXSess (Graz, Austria) with PANalytical PW3830 stand-alone X-ray generator operating at 40 kv, 50 mA with a sealed-tube Cu anode ($\lambda_{Cu-K\alpha}$=0.154 nm). The samples were loaded into a paste cell sample holder at room temperature. All measurements were performed in the heating direction and equilibrated at each temperature for at least 10 min prior to data collection. Temperature control was via a TCU Temperature Control Unit (Anton Paar). All samples were measured using line collimation equipped with an advanced CCD detector (Anton Paar GmbH, 24×24 μm pixel size; Δq=0.0037 $nm^{-1}$). The scattering results were recorded and analysed by the accompanied Anton Paar software.

Results

The results of SAXS are summarised in Tables 6, 7 and 8 and indicate that self-assembled lyotropic liquid crystalline phases were formed for the prodrugs 5-FCPhy and 5-FCOle and a lamellar non-swelling crystalline phase was present. The results of water penetration scans are discussed below.

The textures obtained from water penetration scans along the established concentration gradient from neat amphiphile to pure water provide a quick insight into the lyotropic phase behaviour of a surfactant/water system. Melted neat amphiphile was placed on a microscopic slide and water was then introduced around the edge 5-FCPhy has the ability to form 3D inversed bicontinous cubic phase (Pn3m space group) initially and then transform to 2D hexagonal phase with elevated temperature or with prolonged equilibration time. Likewise, prodrug 5-FCOle was able to form traditional lamellar (L☐) phase at room temperature and 3D cubic (Pn3m) phase at elevated temperatures above 33° C. 5FC-Pal did not swell in the presence of aqueous solutions.

TABLE 6

The phase behaviour of equilibrated 5-FCPhy, at various temperatures.
$H_2$ = hexagonal, Pn3m = 3D inverse cubic, RT = 25° C.

| Composition | Measured Temperature | Phases at RT | Lattice parameter |
|---|---|---|---|
| 5-FCPhy without water | RT 37° C. | Amorphous | — |
| 5-FCPhy in Excess water | RT, 37° C. | $H_2$ | RT: $H_2$(5.82 nm) 37° C.: $H_2$(5.60 nm) |

TABLE 7

The phase behaviour of equilibrated 5-FCOle, at various temperatures. Lc = smectic crystalline phase. Lα = Lamellar liquid crystalline, and Pn3m (D) inverse cubic phases

| Measuring technique | Composition | Measured Temperature | Phases | Lattice parameter (nm) | Error |
|---|---|---|---|---|---|
| XRD | neat | 25° C. | Smectic crystal (Lc) | 2.977 | 0.624 |
| SAXS | neat | 25, 37° C. | Smectic crystal (Lc) | 25° C.: 2.99<br>37° C.: 3.00 | 25° C.: 0.673<br>37° C.: 0.845 |
| | In excess water | RT, 37° C. | RT: Lα<br>37° C. Pn3m | 25° C. Lα: 6.01<br>37° C. Pn3m: 10.40 | 25° C.: 0.650<br>37° C.: 0.432 |
| | In excess water with 2.3% F127 and 4.87% Ethanol | 37° C. | Pn3m | 37° C. Pn3m: 9.10 | 37° C.: 0.005 |

TABLE 8

The phase behaviour of 5-FCPal measured with SAXS and confirmed with XRD

| Composition | Equilibration Time | Measured Temperature | Phases | d-spacing |
|---|---|---|---|---|
| without water | — | RT, 37, 50, 70, 90° C. | Lamellar (crystal) | RT: Lc (2.87 nm) |
| In excess water | @ RT 7Days | RT, 37, 50° C. | Lamellar (crystal) | RT: Lc (2.86 nm) |

The 5-FCSte amphiphile was shown to form lamellar phases in excess water at physiological temperatures, similar to those observed by the 5-FCPal compound. The aliphatic chain of 5-FCSte has no unsaturation and therefore is not likely to induce sufficient curvature to form inverse lyotropic liquid crystalline phases. The 5-FCLeo derivative was shown to form inverse phases at limited hydration and physiological temperatures including the inverse hexagonal phase, and a fluid isotropic phase has been observed under excess water conditions.

Figure 17:
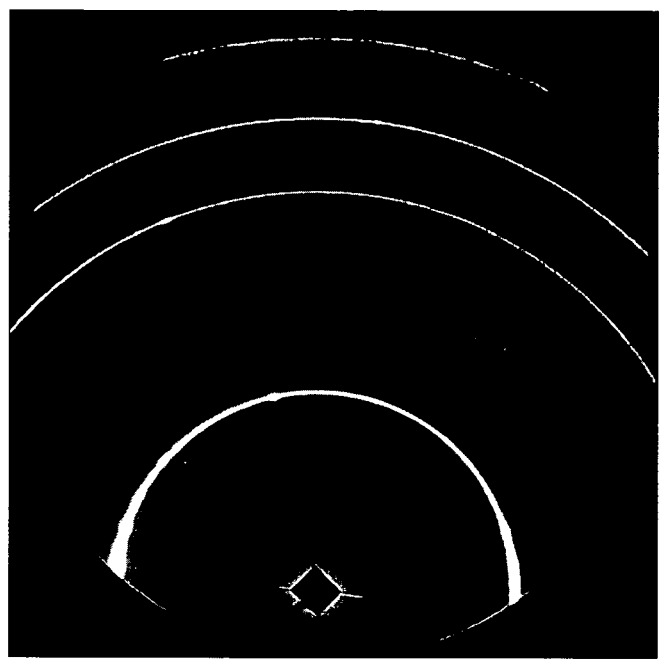
FIG. 17: SAXS of Neat Farnesoyl Dopamine at 25° C.

For the dopamine prodrug amphiphile, SAXS at 25° C. of the neat and excess water amphiphile shows the following results: Lamellar $1^{st}$ and $2^{nd}$ order peaks at d=23.37 A with error=0.06 A. Two additional peaks of an unidentified phase in the ratio 6:7 to each other are also present at d=59.09 A with error=0.17 A. FIG. 17 shows a SAXS pattern of the neat material at room temperature.

Example 3

Preparation of Colloidal Particles or Dispersions

The preferred prodrugs according to the current invention can be dispersed into aqueous solution and form colloidal particles with very fine internal nanostructures and in the size range of 100-1500 nm, by using the following procedure.

Colloidosome Dispersions:

Typical colloidosome dispersions were prepared for 5-FCPhy and 5-FCOle according to the following method: an appropriate amount of 5-FCPhy or 5-FCOle, Poloxamer 407 ($PEO_{98}PPO_{67}PEO_{98}$ with average formula weight of 12,500; BASF) equivalent to 10% (w/w) of neat amphiphile and absolute ethanol were weighed in a sample vial. The dissolved mixture was added dropwise into milli-Q water under vigorous vortexing. The final composition for 5-FCPhy particle dispersion was: 4.74% 5-FCPhy, 0.45% F127, 9% ethanol, 85.7% water while for 5-FCOle the composition was: 2.3% of 5-FCOle, 0.2% F127, 4.87% ethanol and 92.6% of water. These crude dispersions were then passed through a series of PC membranes from the size range from 1 um to 100 nm to obtain a more uniform size distribution for the particles. The equipment used for size control is a mini-extruder (Avanti Polar Lipids, USA). Polycarbonate filters of the sizes 1 ☐m, 800 nm, 400 nm, 200 nm and 100 nm were used consecutively to reduce the size of the particles to 100-200 nm. The final concentration of colloidosomes were determined by ultra performance liquid chromatography (UPLC) and then diluted to 1 mg/mL for use in the enzyme hydrolysis study The particle size distribution and morphology of the above suspensions were determined using the method as described herein by using zetasizer and cryo-TEM characterisation methods.

Solid Lipid Particles:

Solid lipid particles of prodrug 5-FCPal were prepared using mechanical methods. Approximately 700 mg of 5-FCPal crystal with 10% (w/w) of poloxamer F127 were weighed in a vial and heated to just above the melting point (120° C.). The melted prodrug and poloxamer mixture was then transferred to 40 mL of pre-warmed water upon vigorous vortexing. The mixture was then sheared with a rough homogenizer (Ultra Turrax®, T18 Basic, IKA® Werke GmbH & Co. KG, Germany) at 14,000 rpm for 10 min. The resultant dispersion was further transferred to the ultrasonic benchtop cleaner for a few hours of ultra sonication. High pressure homogenization (EmulsiFlex-C3 Homogenizer, Avestin Inc., Canada) at 50 psi with elevated temperature at approximately 50° C. was applied to homogenize the dispersions for 20 min and reduce the particle size.

The final concentration of solid lipid particles was determined by ultra performance liquid chromatography (UPLC) and then diluted to 1 mg/mL for the enzymatic hydrolysis study. The particle size distribution and morphology of above solution were determined using methods as described herein.

Cryo-TEM

Cryo-TEM images of lyotropric liquid crystalline particles and solid lipid particles were obtained using a laboratory-built vitrification system allowing humidity to be kept close to 90% during sample plunging and vitrification. 4-5 μl of sample solution was applied to a 300 mesh copper TEM grid coated with a lacey carbon film (ProSciTech, Thuringowa Qld 4817Australia) and allowed to settle for 30 s. The grid was manually blotted for 10-15 s, and the resulting thin film was then vitrified by plunging into liquid ethane. Grids were stored in liquid nitrogen before transferring into a Gatan 626-DH Cryo-holder. Imaging was carried out using an FEI Tecnai 12 TEM, operating at 120 kV, equipped with a Mega-View III CCD camera and AnalySis imaging software (Olympus Soft Imaging Solutions). The sample was kept at a temperature of −180° C. and standard low-dose procedures were used to minimize radiation damage.

Dispersions Characterization: Particle Size Distribution:

Determination of the particle size distribution of the colloidosome and solid lipid particle dispersions were carried out using a Zetasizer (nano zs, Malvern, England) equipped with a He—Ne Laser (4 mw, 633 nm) and an avalanche photodiode detector. Dynamic light scattering (DLS) analysis was performed on the dispersion in a disposable sizing cuvette with the scattering angle of θ=90° at 25° C. Each measurement was repeated at least two times and the measurement time for every individual run was 60 s. The viscosity and RI value of 0.8872 cp and 1.330 were used respectively in the data calculation. The size distribution was recorded by intensity.

Figure 2:
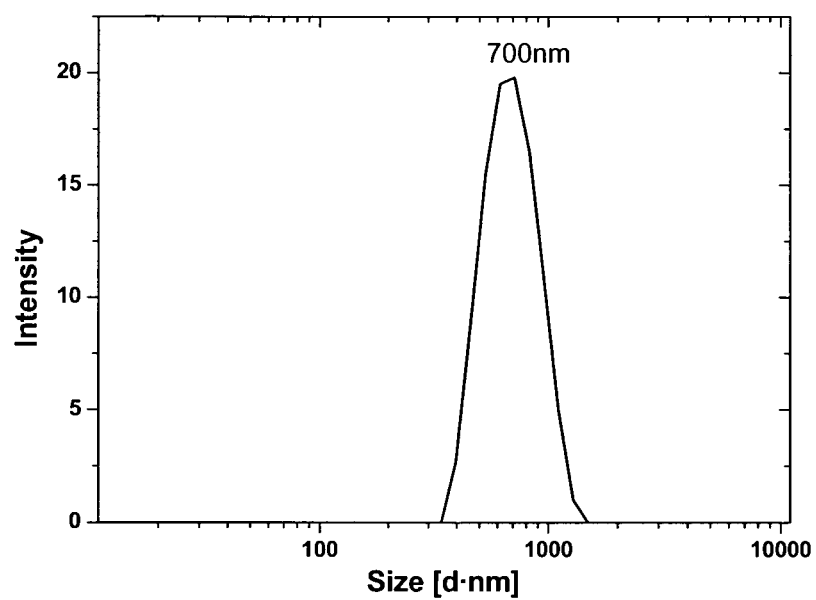
FIG. 2: Particle size distribution (diameter in nm) as determined by DLS of solid lipid particles of 5-FCPal at 25° C. The average size distribution taken from 3 separate measurements is shown.
Figure 4:
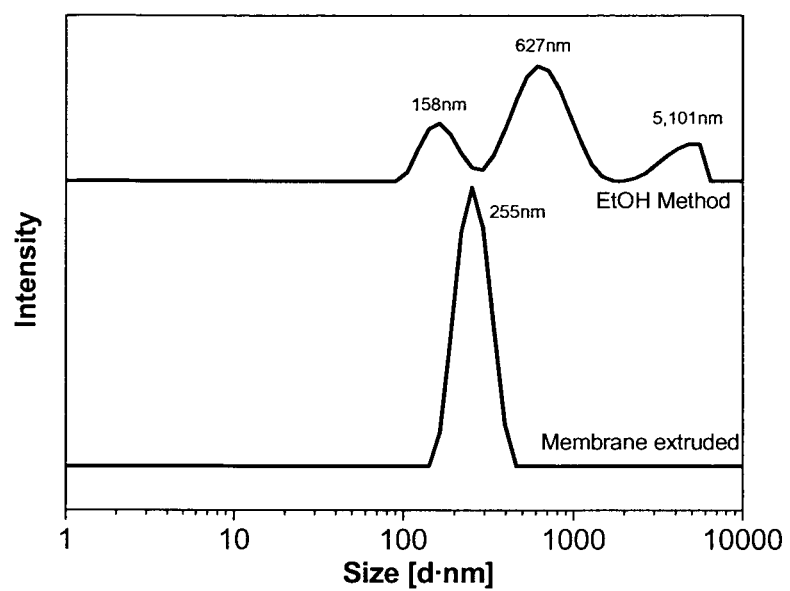
FIG. 4: Particle size distribution (diameter in nm) as determined by DLS of dispersions formed from 5-FCOle/F127/ethanol water solution. Top curve represents the coarse dispersions formed directly using ethanol method. Bottom curve is the size distribution after size controlled membrane extrusion.

The results of the particle dispersions manufactured from the three different prodrugs are shown in FIGS. 2-4.

The 5-FCPhy and 5-FCOle, which demonstrated inverse hexagonal and cubic phases at bulk phases, at physiological temperature, dispersed into smaller particles (mean of 164 and 255 nm respectively) with a relatively narrow size distribution (100-300 nm and 150-500 nm respectively). The 5-FCPal had a crystalline structure and formed solid lipid particles with somewhat larger particles (mean 700 nm), compared to other two prodrug amphiphiles 5-FCPhy and 5-FCOle.

Figure 5:
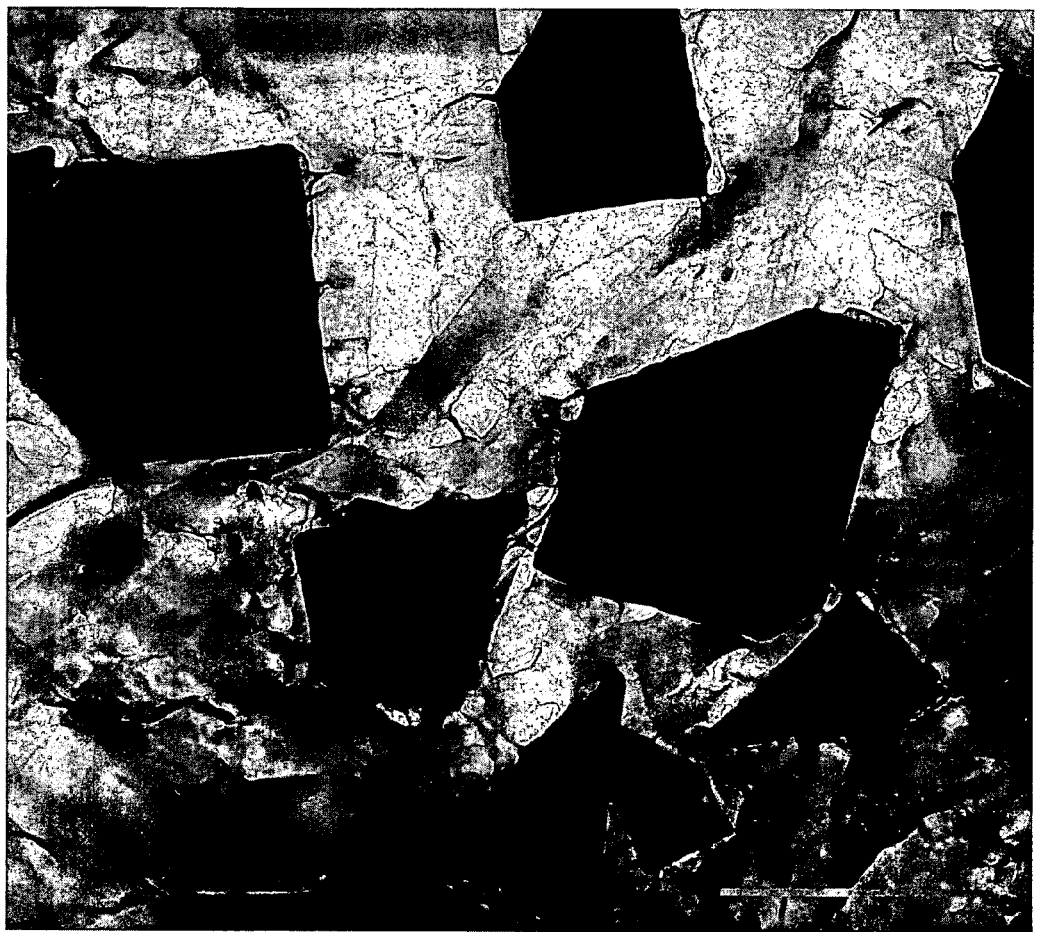
FIG. 5: Cryo-TEM image of 5-FCPal solid lipid particles. Scale bar is 2 microns.
Figure 6:
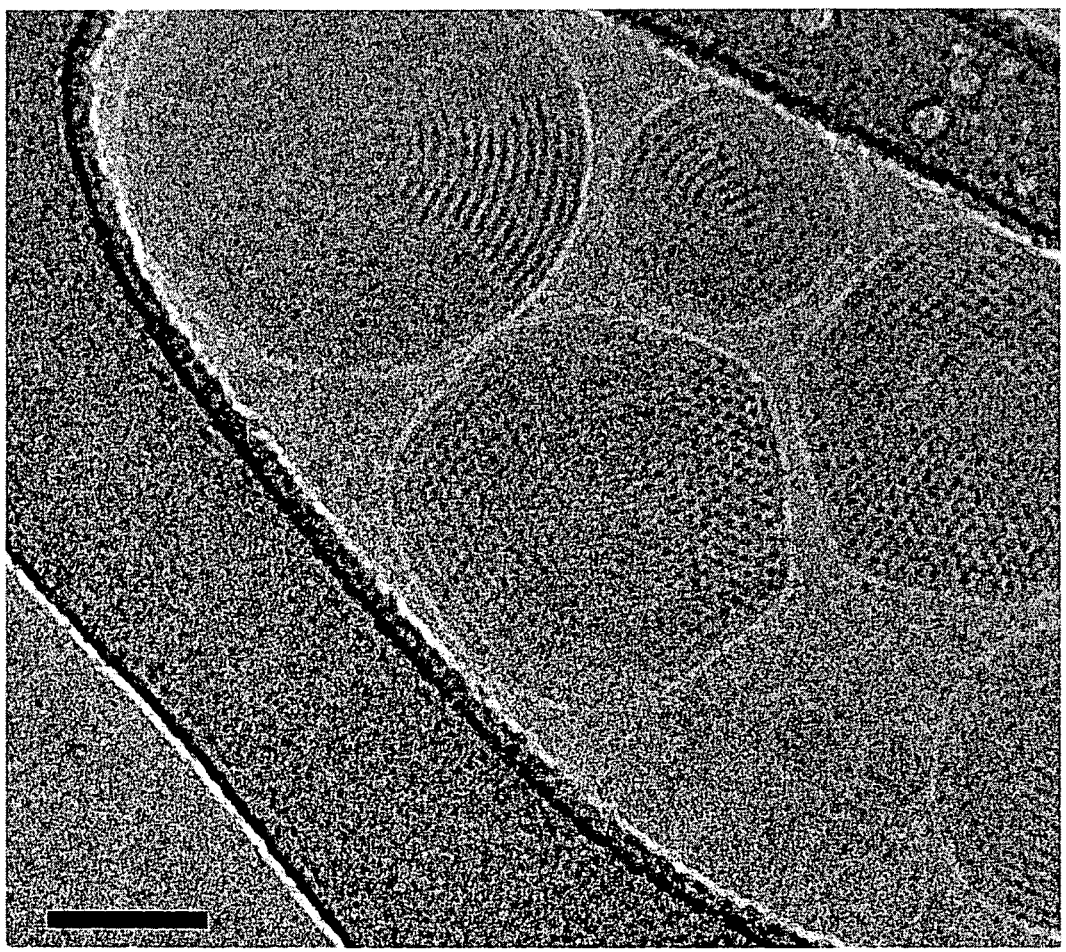
FIG. 6: Cryo-TEM images of 5-FCPhy hexosome particles (dispersion consisting 4.74% of 5-FCPhy, 0.45% F127, 9% ethanol and 85.7% of water). Scale bar is 50 nm.
Figure 7:
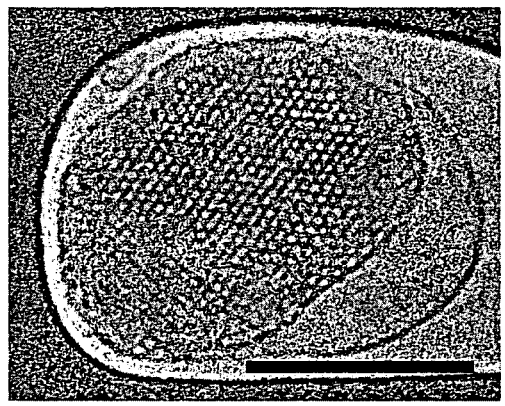
FIG. 7: Cryo-TEM images of dispersions containing 2.3% 5-FCOle, 0.2% F127, 4.87% ethanol and 92.6% water. Top image shows a cubosome which form at physiological temperature. Bottom image shows unilamellar liposomes present at 25° C. Scale bar in both images in 200 nm.
Figure 7:
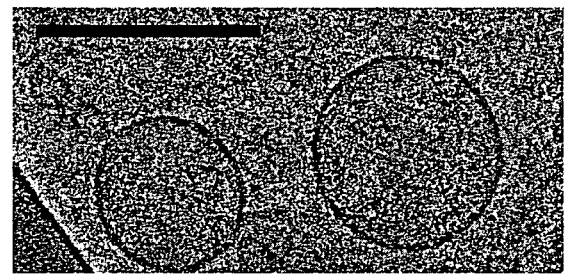
Figure 8:
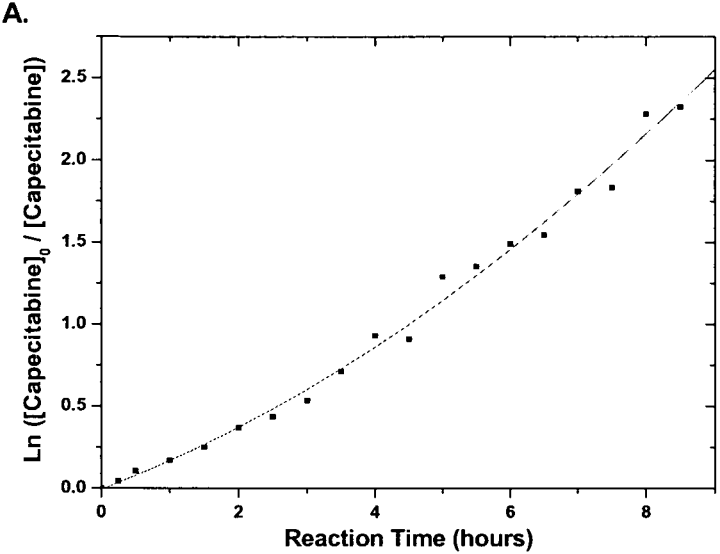
FIG. 8: Plot of the hydrolysis of Capecitabine by porcine liver carboxylesterase (CES) as a function of reaction time. The enzyme concentration for Capecitabine is 0.005 mg/ml.
Figure 9:
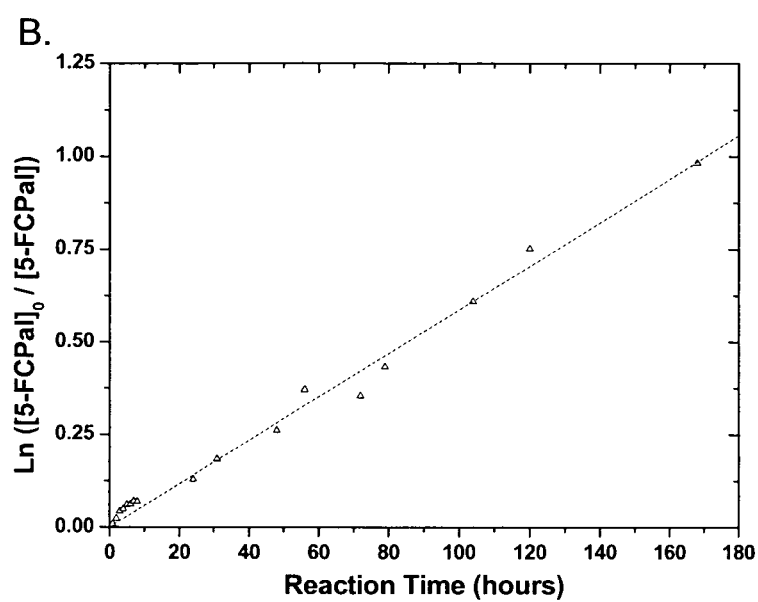
FIG. 9: Plot of the hydrolysis of 5-FCPal by porcine liver CES as a function of reaction time. The enzyme concentration for 5-FCPal is 0.5 mg/ml.
Figure 10:
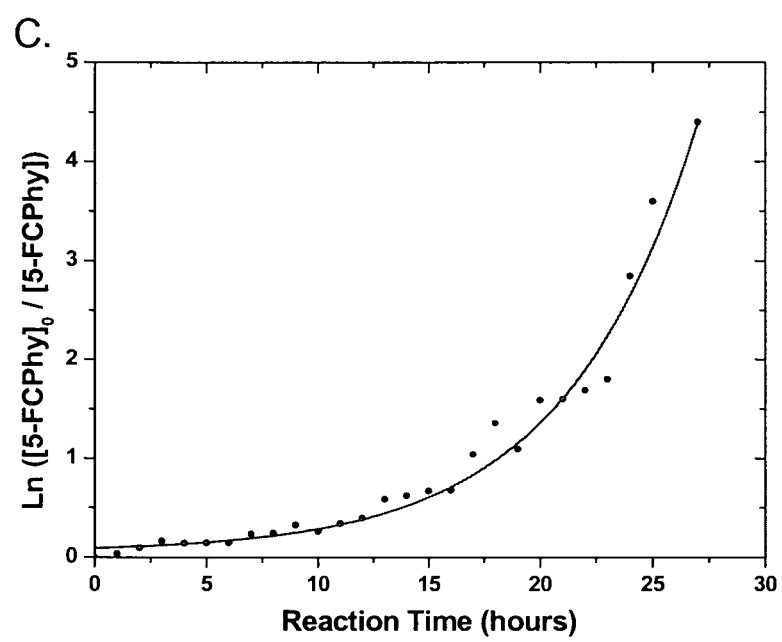
FIG. 10: Plot of the hydrolysis of 5-FCPhy by porcine liver CES as a function of reaction time. The enzyme concentration for 5-FCPhy is 0.5 mg/ml.
Figure 11:
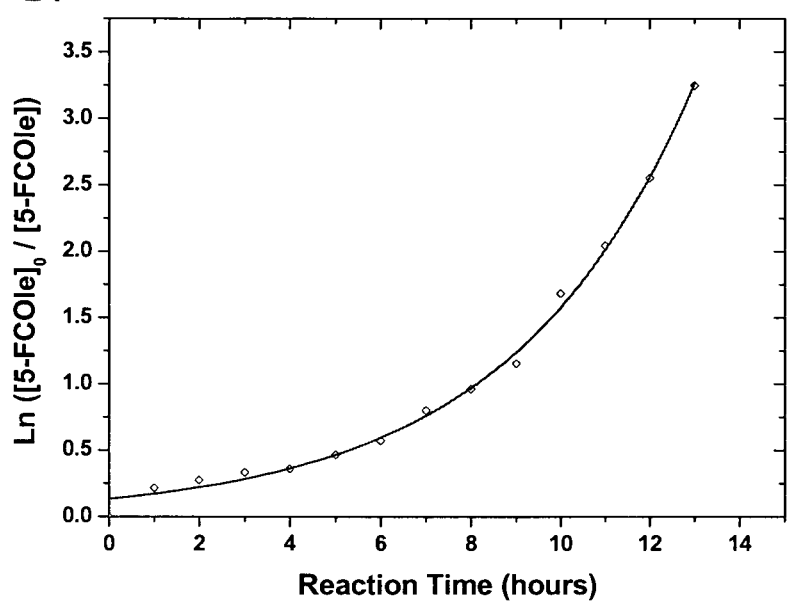
FIG. 11: Plot of the hydrolysis of 5-FCOle by porcine liver CES as a function of reaction time. The enzyme concentration for 5-FCOle is 0.5 mg/ml.
Figure 12:
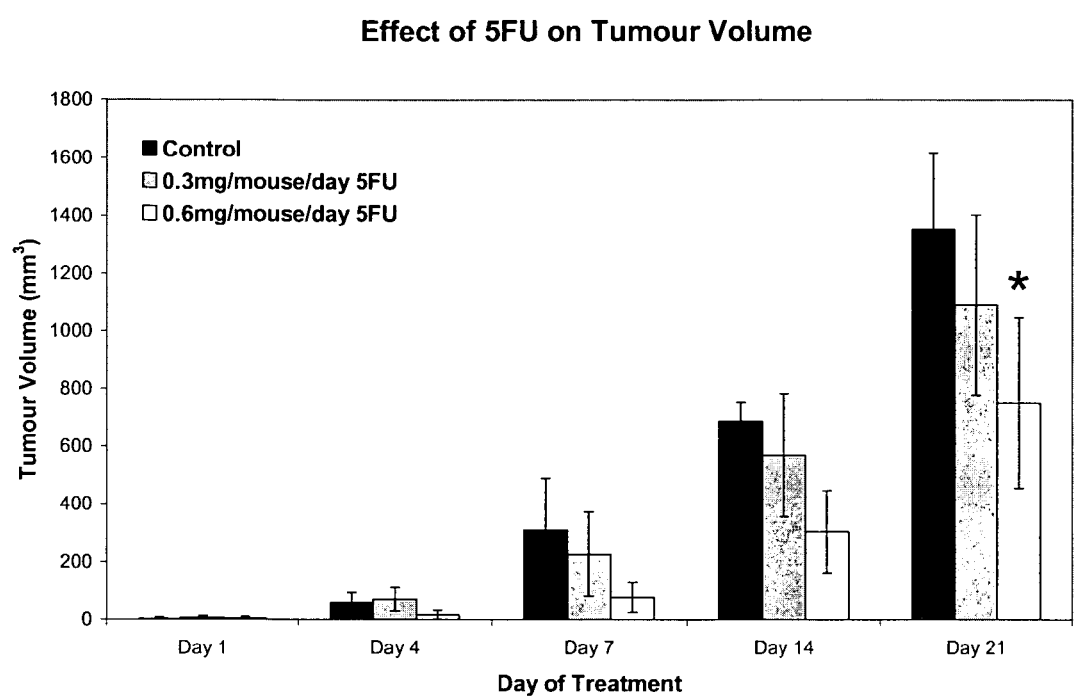
FIG. 12: Effect of administration of 5-FU on mouse breast tumour volume versus time. Volume (length×breadth) of tumour was measured and recorded on day 1, 4, 7, 14, and 21 of the drug/pro-drug administration
Figure 13:
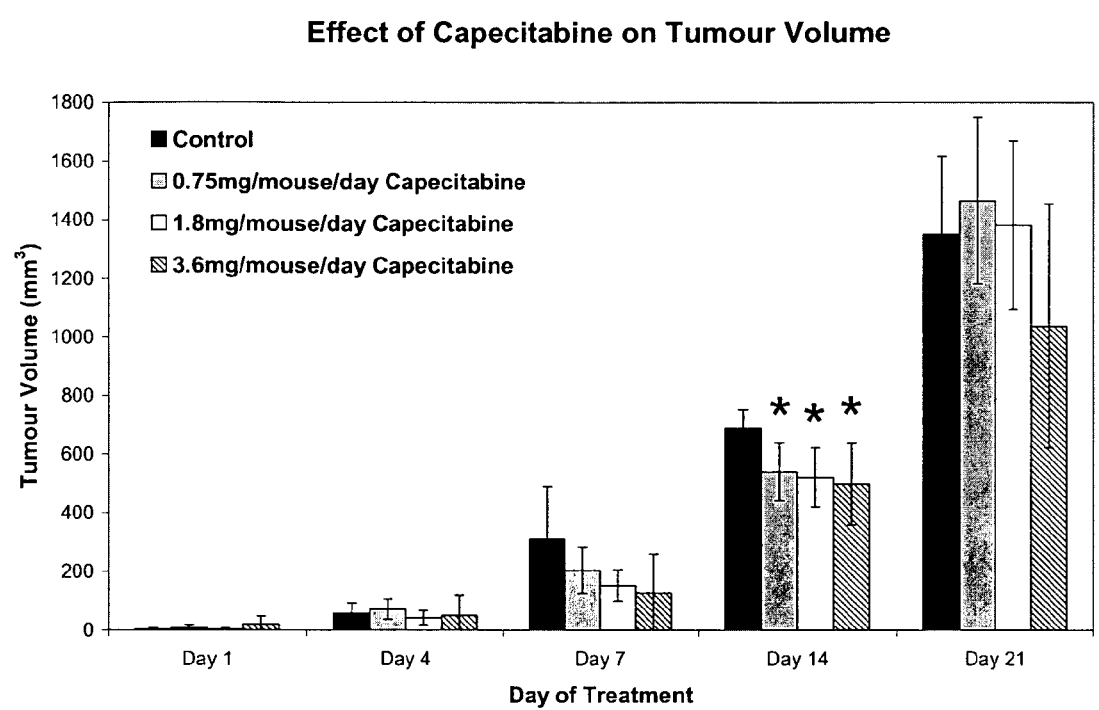
FIG. 13: Effect of administration of capecitabine on mouse breast tumour volume versus time. Volume (length×breadth) of tumour was measured and recorded on day 1, 4, 7, 14, and 21 of the drug/pro-drug administration.
Figure 14:
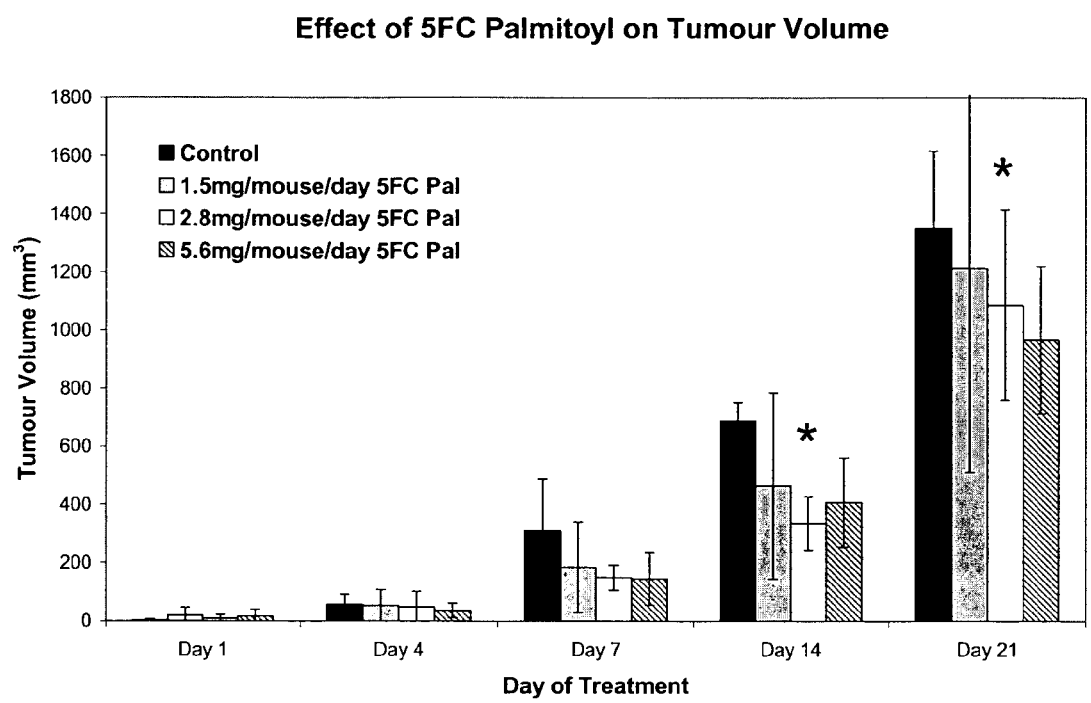
FIG. 14: Effect of administration of 5-FCPal on mouse breast tumour volume versus time. Volume (length×breadth) of tumour was measured and recorded on day 1, 4, 7, 14, and 21 of the drug/pro-drug administration.
Figure 15:
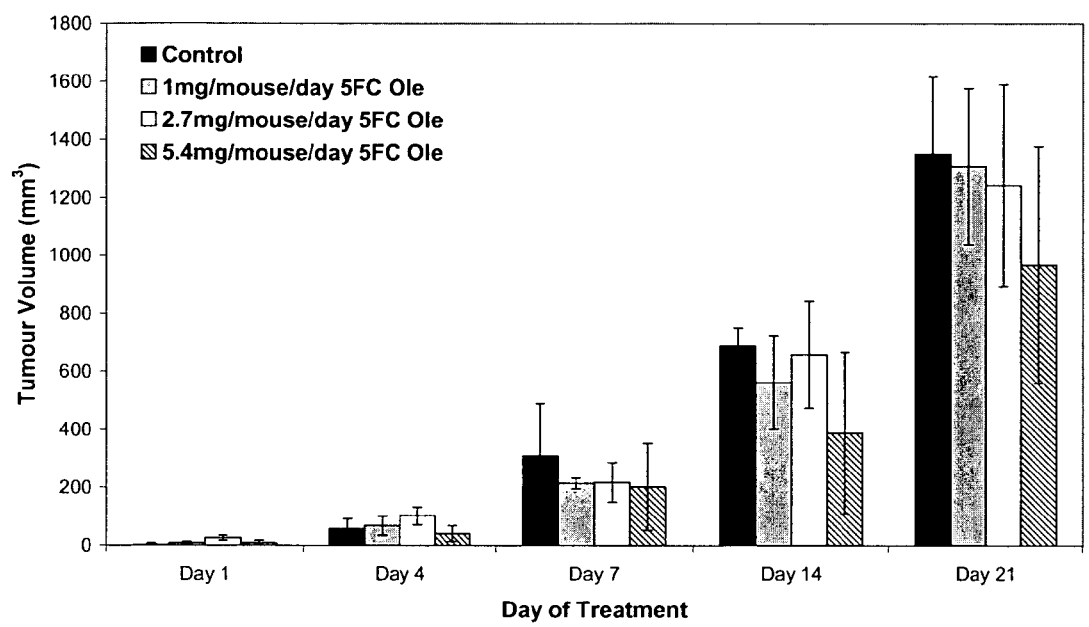
FIG. 15: Effect of administration of 5-FCOle on mouse breast tumour volume versus time. Volume (length×breadth) of tumour was measured and recorded on day 1, 4, 7, 14, and 21 of the drug/pro-drug administration.
Figure 16:
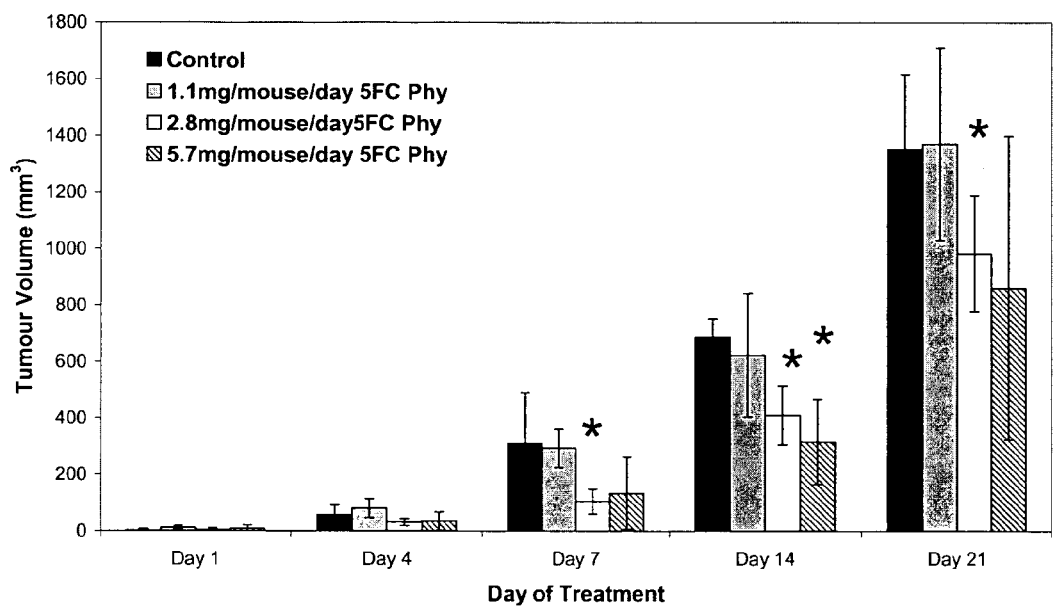
FIG. 16: Effect of administration of 5-FCPhy on mouse breast tumour volume versus time. Volume (length×breadth) of tumour was measured and recorded on day 1, 4, 7, 14, and 21 of the drug/pro-drug administration.

Typical cryo-TEM micrographs of the three different particle dispersions are shown in FIGS. 5-7.

Example 4

In Vitro Results—Enzyme Assay

Materials.

High purity Capecitabine (as solid crystals) was purchased from Xingcheng Chemphar Co., Ltd, P.R.China. Surfactant drug conjugates, 5-FCPal, 5-FCPhy and 5-FCOle were synthesized according to the methods in Example 1. Carboxylesterase from porcine liver with 131 Units/mg (pH 8.0, 25° C.) was purchased from Sigma-Aldrich. Millipore water was used to prepare the prodrugs solutions with appropriate concentrations, while phosphate buffered saline (pH 7.4, PBS) was used in the preparation of different concentrations of enzyme. 1 mg/ml for prodrugs 5-FCPal, 5-FCOle and 5-FCPhy, 0.01 mg/ml for Capecitabine Prodrugs Solution Preparation and Characterization.

Stock solution of Capecitabine was prepared by dissolving pure white Capecitabine into warm water. 1 mg/mL of Capecitabine solution was then further obtained by diluting the stock solution with milli-Q water. Colloidosome dispersions were prepared for 5-FCPhy and 5-FCOle according to the method described by Examples 2-3. The ready solution for hydrolysis study was prepared via mixing the same volume of prodrug 1 mg/ml solution with enzyme solution, the final concentration of Capecitabine, 5-FCPhy, 5-FCPal and 5-FCOle for the hydrolysis study were 1.39 mM, 0.878 mM, 0.973 mM and 0.926 mM respectively. Prior to the experiments, prodrug particles were incubated at 37° C. for at least two weeks to achieve the equilibrium state of certain phases.

Enzyme Solution Preparation.

Stock solution of 10 mg/mL carboxylesterase solution was prepared by weighting 10 mg of powder enzyme in 1 mL of PBS buffer and shaking gently by hand. The concentration of the enzyme solution was adjusted to 1 mg/mL and 0.01 mg/mL by dilution of the stock solution. These solutions were used for the enzymatic hydrolysis of the prodrugs and Capecitabine respectively. The final enzyme concentration for this study was 0.5 mg/mL for the three prodrugs and 0.005 mg/ml for Capecitabine.

Hydrolysis Conditions.

To measure the rate of the enzymatic reaction precisely, the starting substrate and the enzyme solution were mixed for a defined time by rapidly mixing together the two stock solutions and shaking. The time at which enzyme solution was added was taken as time zero for the hydrolysis reaction. The mixture was maintained at 37° C. throughout the experiment. The concentration of the hydrolysis product was then measured at various times using LC/MS (Finnigan LCQ Series, Thermo Scientific, USA). The time at which the sample was injected into the LC column was taken to be the reaction time for such sample. The hydrolysis progress curve showing the decrease in the concentration of original substrate was subsequently plotted.

LC/MS Conditions.

The concentrations of prodrugs were determined using Thermo Finnigan LC/MS equipped with an atmospheric pressure chemical ionization (APCI) probe in positive ion mode. 10 μL of sample withdrawn from the reaction solution was injected directly into a Platinum EPS C18 100 Å 5u LC column with the length of 150 mm and internal diameter of 4.6 mm (Alltech, Australia). A mixture of 30% LCMS grade water and 70% Methanol was employed as mobile phase with the flow rate of 1 ml/min. The sample after the column separation was eluted to APCI source (MS full positive scan) to determine the molecular weight of the substrates. The vaporizer temperature of the APCI probe was set at 450° C. and the capillary temperature was operated at 200° C. The sample temperature was well maintained at 37° C. during the entire measurement by incubating the sample in the temperature controlled auto-sampler. Data were acquired and processed with Xcalibur Quan chromatography software.

Prodrug Hydrolysis.

The decreased concentration of substrate and the increased hydrolysis product 5'-dFCyd were detected based on the different retention time on chromatogram and m/z value in the MS positive scan. The more hydrophilic compound at the retention time around 1.8 min with m/z of 246.3 was accountable for the hydrolysed 5'-dFCyd, the retention time of 2.14 min with m/z of 360.0 was assigned as prodrug Capecitabine. The synthesized prodrugs had a retention time of 7.50 min, 7.02 min, 7.07 min with m/z of 570.3, 514.2, 540.2 corresponding to 5-FCPhy, 5-FCPal and 5-FCOle respectively. The decreased/increased ratio of reactant/5'dFCyd was determined by comparing the integration areas of the corresponding peaks.

The reactions curves of the four prodrugs with the CES hydrolysis are plotted and presented in FIGS. 8-11. The enzyme hydrolysis reaction was plotted as the logarithm of the ratio of original prodrug concentration to the decreased concentration of prodrug at a certain incubation time as a function of reaction time (Ln $[S]_0/[S]$ vs T).

In order to compare the enzymatic activity for each individual substrate to CES, we calculate a global reaction rate expressed as a specific activity (SA) (μmol/min/mg enzyme):

$$SA = \Delta[S]/(\Delta t \cdot [C_{CES}])$$

Here, as is common when discussing the SA, $[C_{CES}]$ is the enzyme concentration in mg/ml, $\Delta[S]$ is the substrate concentration change in μmol/ml during $\Delta t$ time. Specific activity values, SA, at various times, t, for each prodrug upon CES hydrolysis are presented in Table 9 (below).

TABLE 9

The physicochemical properties and hydrolysis profile of each prodrug at physiological temperature.

| Prodrug | Lyotropic phase behaviour | Average Particle size (nm) | Specific Activity (SA) (μmol/ml) at time t (h) | | | | | |
|---|---|---|---|---|---|---|---|---|
| | | | t = 0.5 | t = 1 | t = 2 | t = 6 | t = 12 | t = 24 |
| Capecitabine | Dissolved in water | — | 933 | 733 | 717 | 598 | — | — |
| 5-FCPhy | Hexosome (H$_2$) | 219 | — | 1.03 | 1.30 | 0.67 | 0.89 | 1.15 |
| 5-FCPal | Solid lipid particle | 661 | — | 0.30 | 0.38 | 0.33 | — | 0.27 |
| 5-FCOle | Cubosome (Pn3m) | 261 | — | 4.97 | 3.70 | 2.24 | 2.37 | — |

It was found from the experiment that Capecitabine was extremely susceptible to this enzyme. With 5 mg/ml and 0.5 mg/ml enzyme concentration, Capecitabine hydrolyses to 5-FC within 30 min, so the enzyme concentration was adjusted to 100 times less than that for prodrugs (50 μg/ml vs 0.5 mg/ml) in order to obtain sufficient data points for comparison. The enzyme activities for Capecitabine obtained from three enzymatic concentrations were of similar value at around ~600-900 μmol/min/mg enzyme. In the following, the enzyme activity of 50 μg/ml concentration was chosen for comparing with other prodrugs. 5-FCPal, having an SA value of 0.30, is least sensitive to CES hydrolysis. Prodrugs 5-FCPhy and 5-FCOle were about 4 and 10 times higher than 5-FCPal, respectively.

The results obtained here clearly indicate that there is considerable variation in hydrolysis rate between the prodrugs with different colloidosome nanostructure, and that of Capecitabine. In general, self-assembled amphiphiles according to the current invention underwent a much more sluggish hydrolysis than that of the Capecitabine. Amphiphile prodrugs 5-FCPhy and 5-FCOle showed a sustained hydrolysis profile, and fully converted to 5'-dFCyd within 24 hours. 5-FCPal hydrolysed with a very slow rate which continued towards full conversion for more than 7 days.

As the four types of prodrugs experience different microenvironments in water, it is deduced that the hydrolysis profiles have been influenced by the particle structure Liver CES plays an important role in drug and lipid metabolism. It is noteworthy that different nanostructured particles of prodrugs showed considerable different enzyme catalytic properties. Unlike Capecitabine, the present prodrug particles showed a prolonged and sustained hydrolysis rate upon CES addition, lasting for days or a week. The main reason for such sustained hydrolysis is due to the unique physicochemical properties of the prodrugs. The particle size and surface areas may also contribute, at least in part, to such different prodrug hydrolysis properties.

Example 5

In Vivo Toxicity Assessment of Prodrugs in Healthy Mice

Capecitabine solution and prodrug particle solutions were administered direct to the stomach of female BALB/c mice (6 weeks of age) daily. The vehicle containing the stabiliser Poloxamer 407 in water was employed as negative control group. The highest dose, 0.5 mmol/prodrug/mouse/day was used to test if this dosage is toxic to the healthy mice. Except 5-FCOle which was incubated at 37° C. and injected with pre-warmed syringes throughout the experiment, the other prodrugs were administered at room temperature. All test groups contained 6 mice. After 20 days, mice were sacrificed, and the organs were weighed and prepared for histological evaluation. No mice died during the study period and there were no obvious adverse effects on the mice from the administration of the pro-drugs.

Example 6

In Vivo Experiments with 5-FU and Pro-Drugs 90 female BALB/c were injected with 5×10$^4$ 4T1 cells (mouse breast cancer cells) in the second mammary fat pad on the right hand side. The tumour was allowed to form for 6 days prior to drug administration. On day 6, tumours were palpable in most of the mice. Approximately 5% of animals did not form tumours throughout the course of the experiment. Mice were placed into groups of 6, and 15 different treatments were administered orally on a daily basis for 21 days. Dosages administered are displayed in the Table 10 below.

TABLE 10

Dosage of each animal group (6 mice per group)

| | High dose | Medium dose | Low dose |
|---|---|---|---|
| Control | 360 microL (1.5 mg/mL) | — | — |
| 5-FU | 200 microL (3 mg/mL) | 100 microL (3 mg/mL) | — |
| Capecitabine | 240 microL (15 mg/mL) | 120 microL (15 mg/mL) | 50 microL (15 mg/mL) |
| 5-FCPal | 450 microL(225 × 2) (12.6 mg/mL) | 225 microL (12.6 mg/mL) | 90 microL (12.6 mg/mL) |
| 5-FCOle | 500 microL(250 × 2) (10.75 mg/mL) | 250 microL (10.75 mg/mL) | 100 microL (10.75 mg/mL) |
| 5-FCPhy | 590 microL(295 × 2) (9.6 mg/mL) | 295 microL (9.6 mg/mL) | 118 microL (9.6 mg/mL) |

The length and breadth of the tumours were measured and recorded on day 1, 4, 7, 14, and 21 of the drug administration. On Day 22, mice were euthanized. Blood was collected via cardiac puncture, followed by removal of the tumour, liver, spleen and kidney for histological analysis. Lungs were injected with indium ink prior to removal to allow for quantification of the number of lung metastasis in each animal.

The average tumour volume for each treatment group was calculated and plotted over time and can be seen in the graphs displayed in FIGS. 12-16. Only data for mice that developed tumours are included in FIGS. 12-16. No real difference in tumour size was seen at the early time points, however, by day 14, a dose dependant trend was visible for all drugs tested. By day 21, the animals receiving the highest doses of each drug displayed the smallest overall tumour volume. While the 5FU showed the largest effect, the toxicity of this drug was apparent in the behaviour of the mice receiving this drug. Mice were lethargic and appeared generally ill with significant weight loss, while mice receiving the other treatments were still moving around quite well despite the large size of the developing tumours. The 5FC phytanoyl pro-drug showed the second smallest overall tumour volume at day 21, and animals appeared active and healthy. Measurements significantly less than the control are marked by * on the graphs. No significant difference was seen between different pro-drug treatment groups, however trends indicate that the highest dose of each drug was the most effective.

Example 7

In Vivo Experiments with 5-FCPhy and 5-FCOle

Figure 18:
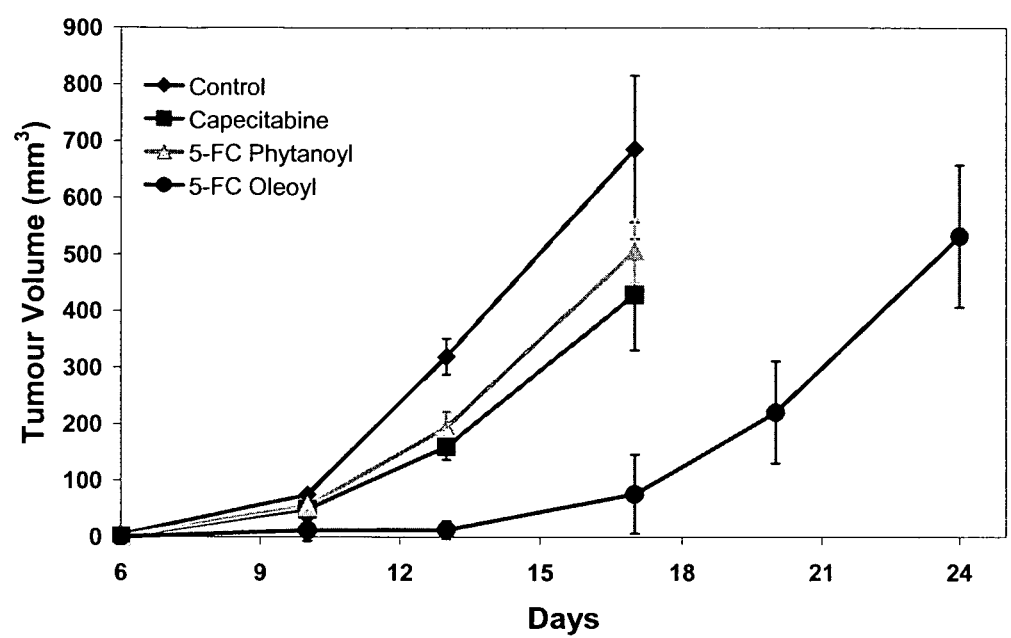
FIG. 18: The average 4T1 tumour volume for the four different treatment groups (control, capecitabine, 5-FCPhy, and 5-FCOle administered daily for 17 days).

Results of a second in vivo study conducted as in Example 6 are shown in the above graph. In this experiment, only 5-FCPhy and 5-FCOle were administered as these had demonstrated the best results from the initial study of Example 6. Also, the dosage of both compounds was increased to 1.5 mmol for each treatment. The graph in FIG. 18 shows the average 4T1 tumour volume for the four different treatment groups (control, capecitabine, 5-FCPhy, and 5-FCOle) over the course of the experiment. By day 17, the control group had the largest tumour, while the 5-FCOle group showed significantly smaller tumour volumes by day 17. On day 17, animals from the control group, capecitabine group, 5-FCPhy, and half of the 5-FCOle group were sacrificed due to tumour size, and treatment was stopped on the 5-FCOle treatment group. It took a full week for the 5-FCOle tumours to grow and reach a similar size as the other treatment groups.

Figure 19:
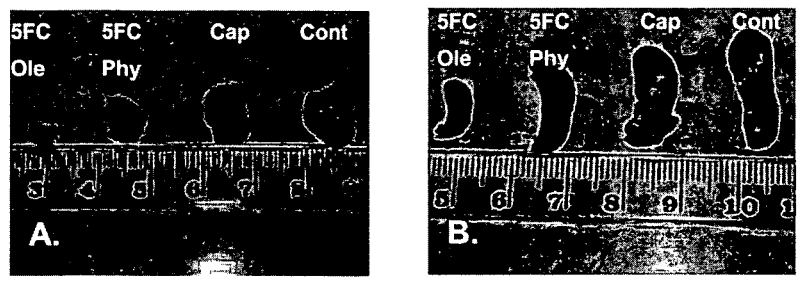
FIG. 19: Images of the tumours and spleens from animals sacrificed at 17 days for the four treatment groups of Example 7 (shown from left to right are 5-FCOle, 5-FCPhy, capecitabine and control).

Images of the tumours and spleens from animals sacrificed at 17 days for the four treatment groups are presented in FIG. 19. The 5-FCOle and 5-FCPhy groups, particularly the 5-Fcole group, shows significantly smaller tumours and normal spleens. Tumours increase in size with the average control tumour being larger than the other treatment groups. In addition, spleens are enlarged 2-3 times in all other groups.

REFERENCE LIST

Yang, S. C.; Lu, L. F.; Cai, Y.; Zhu, J. B.; Liang, B. W.; Yang, C. Z., Body distribution in mice of intravenously injected camptothecin solid lipid nanoparticles and targeting effect on brain. Journal of Controlled Release 1999, 59, (3), 299-307.

Jin; Y; et al. Self-assembled drug delivery systems. 1. Properties and in vitro/in vivo behaviour of acylovir self-assembled nanoparticles (SAN). International Journal of Pharmaceutics, 2006, 309, 199-207

Zhang, J. X.; Qiu, L. Y.; Wu, X. L.; Jin, Y.; Zu, K. J., Temperature-triggered nanosphere formation through self-assembly of amphiphilic polyphosphazene. Macromolecular Chemistry and Physics 2006, 207, (14) 1289-1296.

Shimma, N.; Umeda, I.; Arasaki, M.; Murasaki, C.; Masubuchi, K.; Kohchi, Y.; Miwa, M.; Ura, M.; Sawada, N.; Tahara, H.; Kuruma, I.; Horii, I.; Ishitsuka, H., The design and synthesis of a new tumor-selective fluoropyrimidine carbamate, capecitabine. Bioorganic & Medicinal Chemistry 2000, 8, (7), 1697-1706.

Wuts, P. G. M. Greene, T. W. Protective Groups in Organic Synthesis. John Wiley & Sons, Inc. Hoboken, N.J.: 2007.

Fieser, M; Fieser, L. F.; Smith, J. G; Reagents for Organic Synthesis, Vols 1-17, John Wiley and Sons, New York, N.Y., 1991

Smith, M. B.; March J.; March's Advanced Organic Chemistry, 5th Ed.; John Wiley and Sons, New York, N.Y., 2001

Larock, R. C; Comprehensive Organic Transformations, 2nd Ed.; John Wiley and Sons, New York, N.Y., 1999

Drummond, C. J.; Fong, C., Surfactant self-assembly objects as novel drug delivery vehicles. Current Opinion in Colloid and Interface Science 2000, 4, (6), 449-456.

Laughlin, R. G.; Lynch, M. L.; Marcott, C.; Munyon, R. L.; Marrer, A. M.; Kochvar, K. A., Phase studies by Diffusive Interfacial Transport using near-infrared analysis for water (DIT-NIR). Journal of Physical Chemistry B 2000, 104, (31), 7354-7362.

Laughlin, R. G.; The Aqeuous Phase Behaviour of Surfactants, Academic Press, San Diego, Calif., 1996.

Small, D., Handbook of Lipid Research. ed. D. J. Hanahan ed.; Plenum Press, New York: 1986; Vol. 4.

Cherezov, V.; Fersi, H.; Caffrey, M., Crystallization Screens: Compatibility with the Lipidic Cubic Phase for in Meso Crystallization of Membrane Proteins. Biophys J, 2001; 81, 225-242.

Spicer, P. T.; Hayden, K. L.; Lynch, M. L.; Ofori-Boateng, A.; Burns, J. L., Novel Process for Producing Cubic Liquid Crystalline Nanoparticles (Cubosomes). Langmuir, 2001; 17(19), 5748-5756.

Brannon-Peppas L.; Blanchette, J. O; Nanoparticle and targeted systems for cancer therapy, Advanced Drug Delivery Reviews, 2004, 56(11), 1649-1659

Remington: The Science and Practice of Pharmacy, 21st Ed, University of the Sciences in Philadelphia (eds), Lippincott Williams & Wilkins, Philadelphia, Pa., 2005

Mehnert, W.; Mader, K., Solid lipid nanoparticles—Production, characterization and applications. Advanced Drug Delivery Reviews 2001, 47, (2-3), 165-196.

D. Wells, C. Fong, I. Krodkiewska, C. J. Drummond, J. Phys. Chem. B., 110, 5112-5119, 2006

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. A prodrug of a general formula (II)

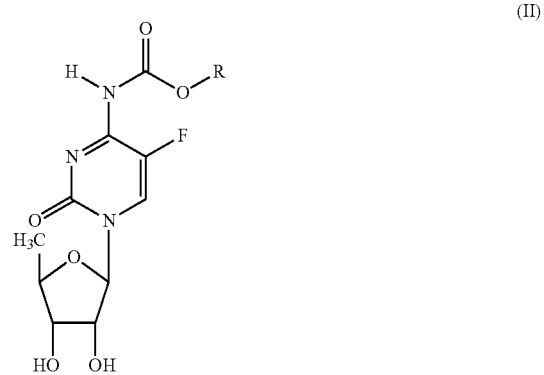

wherein the R group has a chain length equivalent to 14 to 24 carbon atoms and is selected from the group consisting of alkyl, alkenyl, alkynyl, branched alkyl, branched alkenyl, branched alkynyl, substituted alkyl, substituted alkenyl and substituted alkynyl groups, and is capable of conferring self-assembly properties to the prodrug under physiological conditions into a lamellar, inverse hexagonal phase or inverse cubic phase.

2. The prodrug according to claim 1, wherein R is a phytanoyl, oleoyl or palmitoyl.

3. A self-assembled structure formed from a prodrug of formula (II):

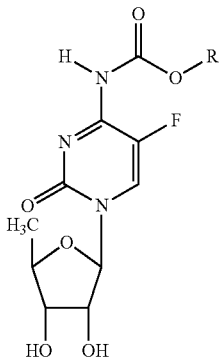

(II)

wherein R is phytanoyl or oleoyl and the structure is a colloidosome; or wherein R is palmitoyl and the structure is a solid lipid particle.

4. A self-assembled structure of claim 3, wherein R is palmitoyl and the structure is a solid lipid particle.

5. A method of modulating the bioavailability of a biologically active agent or an agent capable of being metabolised to a biologically active agent, A, the method including covalently linking A to a tail component, X, to form an amphiphile, capable of self-assembling into a self-assembled structure stable under physiological conditions;

wherein the amphiphile is cleavable in vivo to release A in a biologically active form; and wherein A-X is a compound according to formula (II)

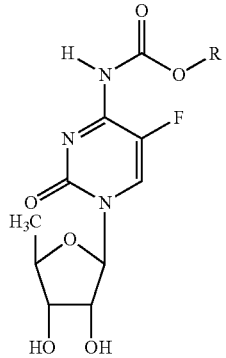

(II)

wherein the R group has a chain length equivalent to 14 to 24 carbon atoms and is selected from the group consisting of alkyl, alkenyl, alkynyl, branched alkyl, branched alkenyl, branched alkynyl, substituted alkyl, substituted alkenyl and substituted alkynyl groups, and is selected so that the amphiphile self-assembles under physiological conditions into a lamellar, inverse hexagonal phase or inverse cubic phase.

6. The method of claim 5, wherein R is phytanoyl or oleoyl and the structure is a colloidosome.

7. The method of claim 5, wherein R is palmitoyl and the structure is a solid lipid particle.

8. The prodrug of claim 1, selected from the group consisting of 5% deoxy-5-fluoro-$N^4$-(3,7,11,15-tetramethyl-hexadecyl-1-oxycarbonyl)cytidine, 5'-deoxy-5-fluoro-$N^4$-(hexadecyl-1-oxycarbonyl)cytidine, 5'-deoxy-5-fluoro-$N^4$-(cis-9-octadecenyl-1-oxycarbonyl)cytidine, 5'-deoxy-5-fluoro-$N^4$-(octadecyl-1-oxycarbonyl)cytidine, 5'-deoxy-5-fluoro-$N^4$-(cis-9, cis-12-octadecadien-1-oxycarbonyl)cytidine, 5'-deoxy-5-fluoro-$N^4$-(cis-6, cis-9, cis-12-octadecatrien-1-oxycarbonyl)cytidine, and 5'-deoxy-5-fluoro-$N^4$-(cis-9, cis-12-octadecenyl-1-oxycarbonyl)cytidine.

9. The prodrug of claim 1, selected from the group consisting of 5'-deoxy-5-fluoro-$N^4$-(3,7,11,15-tetramethyl-hexadecyloxycarbonyl)cytidine, 5'-deoxy-5-fluoro-$N^4$-(hexadecyloxycarbonyl)cytidine, 5'-deoxy-5-fluoro-$N^4$-(cis-9-octadecenyloxycarbonyl)cytidine, 5'-deoxy-5-fluoro-$N^4$-(octadecyl-1-oxycarbonyl)cytidine, and 5'-deoxy-5-fluoro-$N^4$-(cis-9,cis-12-octadecenyl-1-oxycarbonyl)cytidine.

10. The prodrug of claim 1, selected from the group consisting of 5'-deoxy-5-fluoro-$N^4$-(3,7,11,15-tetramethyl-hexadecyl-1-oxycarbonyl) cytidine, 5'-deoxy-5-fluoro-$N^4$-(cis-9-octadecenyl-1-oxycarbonyl)cytidine, 5'-deoxy-5-fluoro-$N^4$-(cis-9, cis-12-octadecadien-1-oxycarbonyl) cytidine, 5'-deoxy-5-fluoro-$N^4$-(cis-6, cis-9, cis-12-octadecatrien-1-oxycarbonyl)cytidine, and 5'-deoxy-5-fluoro-$N^4$-(cis-9,cis-12-octadecenyl-1-oxycarbonyl) cytidine.

* * * * *